United States Patent
Schnell et al.

(10) Patent No.: US 11,015,200 B2
(45) Date of Patent: May 25, 2021

(54) ANTISENSE-INDUCED EXON EXCLUSION IN MYOSTATIN

(71) Applicant: Sarepta Therapeutics, Inc., Cambridge, MA (US)

(72) Inventors: Frederick Joseph Schnell, Corvallis, OR (US); Richard Keith Bestwick, Bend, OR (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/559,257

(22) PCT Filed: Mar. 18, 2016

(86) PCT No.: PCT/US2016/023239
§ 371 (c)(1),
(2) Date: Sep. 18, 2017

(87) PCT Pub. No.: WO2016/149659
PCT Pub. Date: Sep. 22, 2016

(65) Prior Publication Data
US 2018/0355358 A1    Dec. 13, 2018

Related U.S. Application Data

(60) Provisional application No. 62/135,048, filed on Mar. 18, 2015, provisional application No. 62/162,571, filed on May 15, 2015.

(51) Int. Cl.
| | | |
|---|---|---|
| *C07H 21/02* | (2006.01) |
| *C07H 21/04* | (2006.01) |
| *C12N 15/113* | (2010.01) |
| *C07H 21/00* | (2006.01) |
| *A61P 21/00* | (2006.01) |
| *A61K 31/7105* | (2006.01) |
| *C07D 241/02* | (2006.01) |
| *C07D 265/28* | (2006.01) |

(52) U.S. Cl.
CPC ...... *C12N 15/1136* (2013.01); *A61K 31/7105* (2013.01); *A61P 21/00* (2018.01); *C07H 21/00* (2013.01); *C07D 241/02* (2013.01); *C07D 265/28* (2013.01); *C12N 2310/11* (2013.01); *C12N 2310/3145* (2013.01); *C12N 2310/3233* (2013.01); *C12N 2310/346* (2013.01); *C12N 2310/3513* (2013.01); *C12N 2320/33* (2013.01)

(58) Field of Classification Search
CPC ... C12N 15/115; C12N 15/111; C12N 15/113; C12N 2310/11
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 5,013,556 A | 5/1991 | Woodle et al. |
| 5,034,506 A | 7/1991 | Summerton et al. |
| 5,108,921 A | 4/1992 | Low et al. |
| 5,142,047 A | 8/1992 | Summerton et al. |
| 5,166,315 A | 11/1992 | Summerton et al. |
| 5,185,444 A | 2/1993 | Summerton |
| 5,213,804 A | 5/1993 | Martin et al. |
| 5,217,866 A | 6/1993 | Summerton et al. |
| 5,227,170 A | 7/1993 | Sullivan |
| 5,264,221 A | 11/1993 | Tagawa et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,506,337 A | 4/1996 | Summerton et al. |
| 5,512,295 A | 4/1996 | Komberg et al. |
| 5,521,063 A | 5/1996 | Summerton et al. |
| 5,521,291 A | 5/1996 | Curiel et al. |
| 5,527,528 A | 6/1996 | Allen et al. |
| 5,534,259 A | 7/1996 | Zalipsky et al. |
| 5,539,082 A | 7/1996 | Nielsen et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |

(Continued)

FOREIGN PATENT DOCUMENTS

| | | |
|---|---|---|
| AU | 2015203791 | 10/2017 |
| CN | 108699555 | 10/2018 |

(Continued)

OTHER PUBLICATIONS

USPTO; Notice of Allowance dated Jun. 13, 2018 in U.S. Appl. No. 15/078,029.
Written Opinion of the International Searching Authority for Application No. PCT/US2006/004797 dated Oct. 31, 2006.
AU; Notice of Acceptance for Patent Application dated Jun. 15, 2017 in AU Application No. 2015203791.
International Preliminary Report on Patentability for Application No. PCT/US2006/004797 dated Feb. 9, 2006.
USPTO; Restriction Requirement in U.S. Appl. No. 11/433,724 dated Mar. 17, 2008.
USPTO; Non-Final Office Action in U.S. Appl. No. 11/433,724 dated Sep. 17, 2008.

(Continued)

*Primary Examiner* — Amy H Bowman
(74) *Attorney, Agent, or Firm* — Snell & Wilmer LLP

(57) ABSTRACT

The present disclosure relates to antisense oligomers and related compositions and methods for decreasing the expression of functional human myostatin and methods for treating muscular dystrophy and related disorders and more specifically relates to inducing exclusion of myostatin exon 2 and thereby reducing the levels of myostatin protein.

14 Claims, 10 Drawing Sheets

Specification includes a Sequence Listing.

(56) References Cited

U.S. PATENT DOCUMENTS

| | | |
|---|---|---|
| 5,580,575 A | 12/1996 | Unger et al. |
| 5,583,020 A | 12/1996 | Sullivan |
| 5,591,721 A | 1/1997 | Agrawal et al. |
| 5,595,756 A | 1/1997 | Bally et al. |
| 5,627,274 A | 5/1997 | Kole et al. |
| 5,665,593 A | 9/1997 | Kole et al. |
| 5,698,685 A | 12/1997 | Summerton et al. |
| 5,707,618 A | 1/1998 | Armentano et al. |
| 5,714,331 A | 2/1998 | Buchardt et al. |
| 5,719,262 A | 2/1998 | Buchardt et al. |
| 5,770,713 A | 6/1998 | Imbach et al. |
| 5,916,808 A | 6/1999 | Kole et al. |
| 5,976,879 A | 11/1999 | Kole et al. |
| 6,005,079 A | 12/1999 | Casterman et al. |
| 6,060,456 A | 5/2000 | Arnold et al. |
| 6,096,506 A | 8/2000 | Lee et al. |
| 6,103,466 A | 8/2000 | Grobet et al. |
| 6,133,246 A | 10/2000 | McKay et al. |
| 6,172,216 B1 | 1/2001 | Bennett et al. |
| 6,210,892 B1 | 4/2001 | Bennnett et al. |
| 6,214,986 B1 | 4/2001 | Bennnett et al. |
| 6,228,579 B1 | 5/2001 | Zyskind et al. |
| 6,239,265 B1 | 5/2001 | Cook |
| 6,245,747 B1 | 6/2001 | Porter et al. |
| 6,284,882 B1 | 9/2001 | Wu Wong et al. |
| 6,287,860 B1 | 9/2001 | Monia et al. |
| 6,365,351 B1 | 4/2002 | Iversen |
| 6,399,312 B2 | 6/2002 | Wu-Wong et al. |
| 6,468,535 B1 | 10/2002 | Lee et al. |
| 6,495,663 B1 | 12/2002 | Rothbard et al. |
| 6,617,440 B1 | 9/2003 | Findly |
| 6,653,467 B1 | 11/2003 | Matsuo et al. |
| 6,669,951 B2 | 12/2003 | Rothbard et al. |
| 6,670,461 B1 | 12/2003 | Wengel et al. |
| 6,677,153 B2 | 1/2004 | Iversen |
| 6,784,291 B2 | 8/2004 | Iversen et al. |
| 6,794,499 B2 | 9/2004 | Wengel et al. |
| 6,828,105 B2 | 12/2004 | Stein et al. |
| 6,841,542 B2 | 1/2005 | Bartelmez |
| 6,965,025 B2 | 11/2005 | Gaarde et al. |
| 6,969,400 B2 | 11/2005 | Rhee et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,049,431 B2 | 5/2006 | Iversen et al. |
| 7,053,207 B2 | 5/2006 | Wengel |
| 7,060,809 B2 | 6/2006 | Wengel et al. |
| 7,084,125 B2 | 8/2006 | Wengel |
| 7,094,765 B1 | 8/2006 | Iversen et al. |
| 7,125,994 B2 | 10/2006 | Kim et al. |
| 7,145,006 B2 | 12/2006 | Kim et al. |
| 7,148,204 B2 | 12/2006 | Bennnett et al. |
| 7,179,896 B2 | 2/2007 | Kim et al. |
| 7,211,668 B2 | 5/2007 | Kim et al. |
| 7,468,418 B2 | 12/2008 | Iversen et al. |
| 7,534,879 B2 | 5/2009 | van Deutekom |
| 7,569,575 B2 | 8/2009 | Sorensen et al. |
| 7,572,582 B2 | 8/2009 | Wengel et al. |
| 7,618,814 B2 | 11/2009 | Bentwich |
| 7,807,159 B2 | 10/2010 | Chin et al. |
| 7,807,816 B2 | 10/2010 | Wilton et al. |
| 7,887,793 B2 | 2/2011 | Tremblay |
| 7,888,012 B2 | 2/2011 | Iversen et al. |
| 7,935,816 B2 | 5/2011 | Li |
| 7,943,762 B2 | 5/2011 | Weller et al. |
| 7,977,472 B2 | 7/2011 | Beigelman et al. |
| 8,066,996 B2 | 11/2011 | Calleja et al. |
| 8,076,476 B2 | 12/2011 | Reeves et al. |
| 8,779,128 B2 | 7/2014 | Hanson et al. |
| 8,785,410 B2 | 7/2014 | Iversen et al. |
| 9,322,019 B2 | 4/2016 | Dickson |
| 10,006,031 B2 | 6/2018 | Iversen et al. |
| 10,106,795 B2 | 10/2018 | Dickson et al. |
| 10,662,431 B2 | 5/2020 | Dickson et al. |
| 2003/0074680 A1 | 4/2003 | Lee et al. |
| 2003/0123191 A1 | 7/2003 | Kasamatsu et al. |
| 2003/0129171 A1 | 7/2003 | Grobet et al. |
| 2003/0235845 A1 | 12/2003 | Ommen et al. |
| 2004/0242528 A1 | 12/2004 | Hagstrom et al. |
| 2004/0265879 A1 | 12/2004 | Iversen et al. |
| 2004/0266720 A1 | 12/2004 | Iversen et al. |
| 2005/0124566 A1 | 6/2005 | Robin et al. |
| 2006/0030522 A1 | 2/2006 | Knopf et al. |
| 2006/0276425 A1 | 12/2006 | Mourich et al. |
| 2006/0287268 A1 | 12/2006 | Iversen et al. |
| 2007/0105807 A1 | 5/2007 | Sazani et al. |
| 2007/0122821 A1 | 5/2007 | Iversen et al. |
| 2007/0249538 A1 | 10/2007 | Sazani et al. |
| 2008/0119426 A1 | 5/2008 | Dale |
| 2009/0005308 A1 | 1/2009 | Knopf et al. |
| 2009/0082547 A1 | 3/2009 | Iversen et al. |
| 2009/0088562 A1 | 4/2009 | Weller et al. |
| 2009/0099066 A1 | 4/2009 | Moulton et al. |
| 2009/0105139 A1 | 4/2009 | Kole et al. |
| 2009/0110689 A1 | 4/2009 | Mourich et al. |
| 2009/0246221 A1 | 10/2009 | Mourich et al. |
| 2009/0264353 A1 | 10/2009 | Orum et al. |
| 2009/0269755 A1 | 10/2009 | Aartsma-Rus et al. |
| 2009/0312532 A1 | 12/2009 | Deutekom et al. |
| 2010/0003218 A1 | 1/2010 | Duan et al. |
| 2010/0016215 A1 | 1/2010 | Moulton et al. |
| 2010/0130591 A1 | 5/2010 | Sazani et al. |
| 2010/0184670 A1 | 7/2010 | Mourich et al. |
| 2010/0272734 A1 | 10/2010 | Berger et al. |
| 2011/0269820 A1 | 11/2011 | Singh et al. |
| 2011/0294753 A1 | 12/2011 | De Kimpe et al. |
| 2011/0312086 A1 | 12/2011 | Deutekom |
| 2012/0059042 A1 | 3/2012 | Platenburg et al. |
| 2012/0202752 A1 | 8/2012 | Lu |
| 2013/0085139 A1 | 4/2013 | Dickson et al. |
| 2013/0211062 A1 | 8/2013 | Watanabe et al. |
| 2014/0045916 A1 | 2/2014 | Iversen et al. |
| 2014/0057964 A1 | 2/2014 | Popplewell et al. |
| 2014/0113955 A1 | 4/2014 | De Kimpe et al. |
| 2014/0315862 A1 | 10/2014 | Kaye |
| 2014/0323544 A1 | 10/2014 | Bestwick et al. |
| 2014/0323956 A1 | 10/2014 | Mendell et al. |
| 2014/0343266 A1 | 11/2014 | Watanabe et al. |
| 2015/0045413 A1 | 2/2015 | De Visser et al. |
| 2015/0073140 A1 | 3/2015 | Hanson et al. |
| 2015/0166996 A1 | 6/2015 | Deutekom |
| 2015/0203849 A1 | 7/2015 | Deutekom |
| 2016/0281092 A1 | 9/2016 | Iversen et al. |
| 2017/0022502 A1 | 1/2017 | Dickson |
| 2018/0327749 A1 | 11/2018 | Iversen |
| 2019/0048350 A1 | 2/2019 | Dickson |
| 2020/0017859 A1 | 1/2020 | Dickson |
| 2020/0263182 A1 | 8/2020 | Dickson |

FOREIGN PATENT DOCUMENTS

| | | |
|---|---|---|
| EP | 3359668 | 8/2018 |
| JP | 2010-532168 | 10/2010 |
| JP | 2015-522275 | 8/2015 |
| JP | 2018-518148 | 7/2018 |
| JP | 2018-530560 | 10/2018 |
| WO | 1993001286 | 1/1993 |
| WO | 1993024510 | 12/1993 |
| WO | 1994004678 | 3/1994 |
| WO | 199426887 | 11/1994 |
| WO | 1994025591 | 11/1994 |
| WO | 1994026764 | 11/1994 |
| WO | 19973461 | 9/1997 |
| WO | 199740854 | 11/1997 |
| WO | 199902667 | 1/1999 |
| WO | 200020432 | 4/2000 |
| WO | 200172765 | 10/2001 |
| WO | 200183740 | 11/2001 |
| WO | 2004043977 | 5/2004 |
| WO | 2004097017 | 11/2004 |
| WO | 2005107447 | 11/2005 |
| WO | 2006000057 | 1/2006 |
| WO | 2006083183 | 8/2006 |
| WO | 2006086667 | 8/2006 |

(56) References Cited

FOREIGN PATENT DOCUMENTS

| WO | 2006116269 | | 11/2006 | |
|---|---|---|---|---|
| WO | 2007002390 | | 1/2007 | |
| WO | 2007058894 | | 5/2007 | |
| WO | 2008005019 | | 1/2008 | |
| WO | 2008036127 | | 3/2008 | |
| WO | 2008051306 | | 5/2008 | |
| WO | 2008131807 | | 11/2008 | |
| WO | 2008153933 | | 12/2008 | |
| WO | 2009005793 | | 1/2009 | |
| WO | 2009008725 | | 1/2009 | |
| WO | WO 2009/005793 | A2 * | 1/2009 | ........... C12N 15/111 |
| WO | 2009064471 | | 5/2009 | |
| WO | 2009086469 | | 7/2009 | |
| WO | 2009088895 | | 7/2009 | |
| WO | 2010019261 | | 2/2010 | |
| WO | 2010048586 | | 4/2010 | |
| WO | 2010080554 | | 7/2010 | |
| WO | 2010115993 | | 10/2010 | |
| WO | 2010120820 | | 10/2010 | |
| WO | 2010129406 | | 11/2010 | |
| WO | 2010148249 | | 12/2010 | |
| WO | 2011057350 | | 5/2011 | |
| WO | 2011150408 | | 12/2011 | |
| WO | 2012043730 | | 4/2012 | |
| WO | 2012150960 | | 11/2012 | |
| WO | 2013053928 | | 4/2013 | |
| WO | 2013074834 | | 5/2013 | |
| WO | 2013112053 | | 8/2013 | |
| WO | 2125006 | | 10/2013 | |
| WO | 2014100714 | | 6/2014 | |
| WO | 2014153220 | | 9/2014 | |
| WO | 2014172448 | | 10/2014 | |
| WO | 2015035231 | | 3/2015 | |
| WO | 2016149659 | | 9/2016 | |
| WO | 2017062835 | | 4/2017 | |

OTHER PUBLICATIONS

USPTO; Non-Final Office Action in U.S. Appl. No. 11/433,724 dated Jun. 11, 2009.
USPTO; Notice of Allowance in U.S. Appl. No. 11/433,724 dated Sep. 29, 2010.
USPTO; Restriction Requirement in U.S. Appl. No. 12/983,798 dated Jun. 19, 2012.
USPTO; Non-Final Office Action in U.S. Appl. No. 12/983,798 dated Sep. 6, 2013.
USPTO; Non-Final Office Action in U.S. Appl. No. 12/983,798 dated Jan. 24, 2013.
USPTO; Notice of Allowance in U.S. Appl. No. 12/983,798 dated Mar. 13, 2014.
USPTO; Restriction Requirement in U.S. Appl. No. 13/644,363 dated Jun. 13, 2013.
USPTO; Non-Final Office Action in U.S. Appl. No. 13/644,363 dated Jul. 24, 2013.
USPTO; Non-Final Office Action in U.S. Appl. No. 13/644,363 dated Jan. 16, 2014.
USPTO; Non-Final Office Action in U.S. Appl. No. 13/644,363 dated Jun. 2, 2014.
USPTO; Restriction Requirement in U.S. Appl. No. 14/323,349 dated Aug. 5, 2015.
USPTO; Non-Final Office Action in U.S. Appl. No. 14/323,349 dated Dec. 10, 2015.
USPTO; Restriction Requirement in U.S. Appl. No. 14/504,453 dated Jan. 14, 2015.
USPTO; Non-Final Office Action in U.S. Appl. No. 14/504,453 dated May 27, 2015.
USPTO; Notice of Allowance in U.S. Appl. No. 14/504,453 dated Sep. 10, 2015.
USPTO; Notice of Allowance in U.S. Appl. No. 14/504,453 dated Dec. 29, 2015.
USPTO; Requirement for Restriction in U.S. Appl. No. 15/078,029 dated Nov. 17, 2016.
USPTO; Non-Final Office Action in U.S. Appl. No. 15/078,029 dated Jun. 15, 2017.
USPTO; Non-Final Office Action in U.S. Appl. No. 15/177,244 dated Aug. 1, 2017.
International Search Report for Application No. PCT/AU2005/000943 dated Oct. 20, 2005.
International Search Report for Application No. PCT/EP2007/061211 dated Dec. 18, 2008.
International Search Report for Application No. PCT/US1994/005181 dated Oct. 7, 1994.
International Search Report for Application No. PCT/US1999/022448 dated Dec. 23, 1999.
International Search Report for Application No. PCT/US2000/008174 dated Jul. 25, 2000.
International Search Report for Application No. PCT/US2001/014410 dated Mar. 6, 2002.
International Search Report for Application No. PCT/US2006/043651 dated Jun. 27, 2007.
International Search Report for Application No. PCT/US2007/010556 dated Mar. 13, 2008.
International Search Report for Application No. PCT/US2008/088339 dated Jun. 4, 2009.
International Search Report for Application No. PCT/US2009/061960 dated Apr. 6, 2010.
International Search Report for Application No. PCT/US2009/068599 dated May 21, 2010.
International Search Report & Written Opinion for Application No. PCT/US2016/023239 dated Sep. 9, 2016.
CIPO; Office Action dated Apr. 5, 2016 in Canadian Application No. 2,596,506.
Invitation to Pay Additional Fees and where applicable, Protest fee for Application No. PCT/US2016/23239 dated Jun. 22, 2016.
Written Opinion of the International Searching Authority for Application No. PCT/US2009/068599 dated May 21, 2010.
Written Opinion of the International Searching Authority for Application No. PCT/US2009/061960 dated Apr. 6, 2010.
Written Opinion of the International Searching Authority for Application No. PCT/US2008/088339 dated Jun. 4, 2009.
Written Opinion of the International Searching Authority for Application No. PCT/US2007/010556 dated Mar. 13, 2008.
Written Opinion of the International Searching Authority for Application No. PCT/US2006/043651 dated Jun. 27, 2007.
Written Opinion of the International Searching Authority for Application No. PCT/EP2007/0061211 dated Dec. 18, 2008.
Written Opinion of the International Searching Authority for Application No. PCT/AU2005/000943 dated Oct. 20, 2005.
International Search Report & Written Opinion for Application No. PCT/US2016/056093 dated Apr. 28, 2017.
EP; Office Action dated Sep. 24, 2010 in EP Application No. 2006734779.
AU; Office Action dated Jun. 7, 2011 in AU Application No. 2006213686.
EP; Office Action dated Sep. 25, 2013 in EP Application No. 2006734779.
AU; Office Action dated Jan. 17, 2014 in AU Application No. 2003201250.
EP; Office Action dated Aug. 14, 2014 in EP Application No. 2006734779.
AU; Notice of Allowance dated Apr. 20, 2015 in AU Application No. 2003201250.
AU; Office Action dated Oct. 7, 2016 in AU Application No. 2015203791.
AU; Office Action dated Jan. 6, 2017 in AU Application No. 2015203791.
Aartsma-Rus et al. "Antisense-mediated exon skipping: a versatile tool with therapeutic and research applications," RNA, vol. 13, pp. 1609-1624, (2007).
Aartsma-Rus et al., "Theoretic Applicability of Antisense Mediated Exon Skipping for Duchenne Muscular Dystrophy Mutations," Human Mutation, vol. 30, No. 3, pp. 293-299 (2009).

(56) References Cited

OTHER PUBLICATIONS

Agrawal et al., "Site-Specific excision from RNA by Rnase H and mixed-phosphate-backbone oligodeoxynucleotides," Proc Natl Acad Sci USA, vol. 87(4), pp. 1401-1405, (1990).
Amali et al., "Up-Regulation of muscle-specific transcription factors during embryonic somitogenesis of zebrafish (*Danio rerio*) by knock-down of Myostatin-1," Developmental Dynamics, vol. 229, pp. 847-856, (2004).
Bailey, C.P., J.M. Dagle et al., "Cationic oligonucleotides can mediate specific inhibition of gene expression in Xenopus oocytes," Nucleic Acids Res, vol. 26(21), pp. 4860-4867, (1998).
Barawkar, D.A. and T.C. Bruice, "Synthesis, biophysical properties, and nuclease resistance properties of mixed backbone oligodeoxynucleotides containing cationic internucleoside guanidinium linkages: deoxynucleic guanidine/ DNA chimeras," Proc Natl Acad Sci USA, vol. 95(19), pp. 11047-11052, (1998).
Bennett, M.R. and Schwartz, "Antisense Therapy for Angioplasty Restenosis," Circulation, vol. 92(7), pp. 1981-1993, (1995).
Bestas Burcu et al., "Design and Application of Biospecific Splice-Switching Oligonucleotides," Nucleic Acid Therapeutics, vol. 24, No. 1, (2014).
Blommers et al., "An approach to the structure determination of nucleic acid analogues hybridized to RNA. NMR studies of a duplex between 2'-0Me RNA and an oligonucleotide containing a single amide backbone modification," Nucleic Acids Research, vol. 22 (20), pp. 4187-4194, (1994).
Bogdanovich et al., "Functional improvement of dystrophic muscle by myostatin blockade," Nature, vol. 420, pp. 418-421, (2002). Abstract only.
Bonham et al., "An assessment of the antisense properties of Rnase H-competent and steric-blocking oligomers," Nucleic Acids Res, vol. 23(7), pp. 1197-1203, (1995). Abstract only.
Boudvillain et al.,"Transplation-modified oligo (2'-O-methyl ribonucleotide) s: a new tool for selective modulation of gene expression," Biochemistry, vol. 36 (10), pp. 2925-2931, (1997). Abstract only.
Branch et al., "A Good Antisense Molecule is hard to find," Trends in Biochemical, Science, vol. 23, pp. 45-50, (1998).
Chirila et al., "The use of synthetic polymers for delivery of therapeutic antisense oligodeoxynucleotides," Biomaterials, vol. 23, pp. 321-342, (2002). Abstract only.
Cross et al., "Solution structure of an RNA × DNA hybrid duplex containing a 3'-thioformacetal linker and an RNA A-tract," Biochemistry, vol. 36 (14), pp. 4096-4107, (1997). Abstract only.
Dagle et al., "Targeted elimination of zygotic messages in Xenopus laevis embryos by modified oligonucleotides possessing terminal cationic linkages," Nucleic Acids Res, vol. 28 (10), pp. 2153-2157, (2000).
Ding, D. et al., "An oligodeoxyribonucleotide N34 P54 phosphoramidate duplex forms an A-type helix in solution," Nucleic Acids Res, vol. 24(2), pp. 354-360, (1996).
Egholm et al., "PNA hybridizes to complementary oligonucleotides obeying the Watson-Crick hydrogen-bonding rules," Nature, vol. 365 (6446), pp. 566-568, (1993). Abstract only.
EMBL Accession No. DQ927047, "*Homo sapiens* isolate AFRAM_ A02 myostatin (GDF8)," pp. 1-2, (Downloaded by an Examiner on Apr. 4, 2017). (Applicant makes no representation as to the date or the content of the downloaded material including, but not limited to, any sequence information, that was downloaded by the Examiner.).
Felgner et al., "Lipofection: a highly efficient, lipid-mediated DNA-transfection procedure," PNAS, vol. 84(21), pp. 7413-7417, (1987).
Gee, J.E., et al., "Assessment of high-affinity hybridization, RNase H cleavage, and covalent linkage in translation arrest by antisense oligonucleotides," Antisense Nucleic Acid Drug Dev., vol. 8(2), pp. 103-111, (1998). Abstract only.
Gonzalez-Cadavid et al., "Organization of the human myostatin gene and expression in healthy men and HIV-infected men with muscle wasting," PNAS, vol. 95(25), pp. 14938-14943, (1998).

Hudziak et al. "Antiproliferative effects of steric blocking phosphorodiamidate morpholino antisense agents directed against c-myc," Antisense & Nucleic Acid Drug Dev., vol. 10(3), pp. 163-176, (2000). Abstract only.
Hudziak et al. "Resistance of morpholino phosphorodiamidate oligomers to enzymatic degradation," Antisense & Nucleic Acid Drug Dev., vol. 6, pp. 267-272, (1996). Abstract only.
Jagjeet K. Kang et al., "Antisense-induced Myostatin Exon Skipping Leads to Muscle Hypertrophy in Mice Following Octa-guanidine Morpholino Oligomer Treatment," Molecular Therapy, vol. 19 (1), pp. 159-164, (2011).
Jen et al., "Suppression of gene expression by targeted disruption of messenger RNA: available options and current strategies," Stem Cells, vol. 18, pp. 307-319, (2000).
Joulia et al., "Mechanisms involved in the inhibition of myoblast proliferation and differentiation by myostatin," Experimental Cell Research, vol. 286, pp. 263-275, (2003). Abstract only.
Kirk et al., "Myostatin regulation during skeletal muscle regeneration," J. Cell Physiology, vol. 184(3), pp. 356-363, (2000). Abstract only.
Lappalainen et al., "Cationic liposomes improve stability and intracellular delivery of antisense oligonucleotides into CaSki cells," Biochim Biophys Acta, vol. 1196(2), pp. 201-208, (1994). Abstract only.
Lesnikowski et al., "Octa (thymidine methanephosphonates) of partially defined stereochemistry: synthesis and effect of chirality at phosphorus on binding to pentadecadecadeoxyriboadenylic acid," Nucleic Acids Res., vol. 18(8), pp. 2109-2115, (1990).
Levin et al., "Position-dependent effects of locked nucleic acid (LNA) on DNA sequencing and PCR primers," Nucleic Acids Research, vol. 34(142), pp. 1-11, (2006).
Linkletter, B.A. and Bruice, T.C., "Solid-phase synthesis of positively charged deoxynucleic guanidine (DNG) modified oligonucleotides containing neutral urea linkages: Effect of charge deletions on binding and fidelity," Bioorg. Med. Chem., vol. 8(11), pp. 1893-1901, (2000). Abstract only.
Lou et al., "Synthetic hydrogels as carriers in antisense therapy: preliminary evaluation of an oligodeoxynucleotide covalent conjugate with a copolymer of 1-vinyl-2-pyrrolidinone and 2-hydroxyethyl methacrylate," J. Biomaterials Appl., vol. 15(4), pp. 307-320, (2001). Abstract only.
McPherron et al., "Regulation of skeletal muscle mass in mice by a new TGF-beta superfamily member," Nature, vol. 387(6628), pp. 83-90, (1997). Abstract only.
McPherron et al., "Double muscling in cattle due to mutations in the myostatin gene," PNAS, vol. 94(23), pp. 12457-12461, (1997).
Micklefield, J., "Backbone modification of nucleic acids: synthesis, structure and therapeutic applications," Curr Med Chem, vol. 8(10), pp. 1157-1179, (2001). Abstract only.
Moulton, H. M. and J. D. Moulton, "Peptide-assisted delivery of steric-blocking antisense oligomers," Curr Opin Mol Ther., vol. 5(2), pp. 123-132, (2003). Abstract only.
Moulton, H.M. et al., "HIV Tat peptide enhances cellular delivery of antisense morpholino oligomers," Antisense Nucleic Acid Drug Dev., vol. 13(1), pp. 31-43, (2003). Abstract only.
Moulton, H.M., M.H. Nelson, et al., "Cellular uptake of antisense morpholino oligomers conjugated to arginine-rich peptides," Bioconjug Chem., vol. 15(2), pp. 290-299, (2004). Abstract only.
Palu et al., "In pursuit of new developments for gene therapy of human diseases," J. Biotech., vol. 68, pp. 1-13, (1999). Abstract only.
Pari, G.S., et al. "Potent antiviral activity of an antisense oligo-nucleotide complementary to the intron-exon boundary of human cytomegalovirus genes UL36 and UL37," Antimicrob Agents. Chemother., vol. 39(5), pp. 1157-1161, (1995).
Schulte et al., "Effects of resistance training on the rate of muscle protein synthesis in frail elderly people," Int. J. Sport Nutrition Exercise Metab., vol. 11, pp. 111-118, (2001). Abstract only.
Stein, D. et al., "A specificity comparison of four antisense types: morpholino, 2'-O-methyl RNA, DNA, and phosphorothioate DNA," Antisense Nucleic Acid Drug Dev., vol. 7(3), pp. 151-157, (1997). Abstract only.

(56) References Cited

OTHER PUBLICATIONS

Summerton et al., "Morpholino and phosphorothioate antisense oligomers compared in cell-free and in-cell systems," Antisense & Nucleic Acid Drug Development, vol. 7, pp. 63-70, (1997). Abstract only.
Summerton et al., "Morpholino antisense oligomers: the case for an RNase H-independent structural type," Biochim et. Biophys. Acta, vol. 1489, pp. 141-158, (1999). Abstract only.
Summerton, J.J., D. Weller, "Morpholino antisense oligomers: design, preparation, and properties," Antisense Nucleic Acid Drug Dev., vol. 7(3), pp. 187-195, (1997). Abstract only.
Toulme, J.J., R.L. Tinevez, et al., "Targeting RNA structures by antisense oligonucleotides," Biochimie, vol. 78(7), pp. 663-673, (1996). Abstract only.
Wallace et al., "Epidemiology of weight loss in humans with special reference to wasting in the elderly," Int. J. Cardiol, vol. 85(1), pp. 15-21, (2002). Abstract only.
Williams et al., "A single intra-articular injection of liposomally conjugated methotrexate suppresses joint inflammation in rat antigen-induced arthritis," Br. J. Rheumatology, vol. 35(8), pp. 719-724, (1996).
Yarasheski et al., "Serum myostatin-immunoreactive protein is increased in 60-92 year old women and men with muscle wasting," J. Nutrition, Health, Aging, vol. 6(5), pp. 343-348, (2002). Abstract only.
Zhu et al., "Evidence for human immunodeficiency virus type 1 replication in vivo in CD14(+) monocytes and its potential role as a source of virus in patients on highly active antiretroviral therapy," J. Virology, vol. 76(2), pp. 707-716, (2002).
Zimmers et al., "Induction of cachexia in mice by systemically administered myostatin," Science, vol. 296(5572), pp. 1486-1488, (2002). Abstract only.
Zollinger et al., "Meningococcal vaccines—present and future," Transactions of Royal Soc of Tropical Medicine and Hygiene, vol. 85 (Supp. 1), pp. 37-43, (1991). Abstract only.
USPTO; Final Office Action dated Feb. 8, 2018 in U.S. Appl. No. 15/078,029.
USPTO; Notice of Allowance dated Feb. 20, 2018 in U.S. Appl. No. 15/177,244.
Aartsma-Rus et al., "Antisense-Mediated Exon Skipping for Duchenne Muscular Dystrophy," Human Gene Therapy, vol. 20, pp. 660-661, (2009).
Arora et al., "Neutrally Charged Phosphorodiamidate Morpholino Antisense Oligomers: Uptake, Efficacy and Pharmacokinetics," Current Pharmaceutical Biotechnology, vol. 5, pp. 431-439, (2004).
Cory et al., "Use of an Aqueous Soluble Tetrazolium/Formazan Assay for Cell Growth Assays in Culture," Cancer Communications, vol. 3(7), pp. 207-212, (1991).
Gait et al., "Synthetic Analogues of Polynucleotides XII. Synthesis of Thymidine Derivatives Containing an Oxyacetamido- or an Oxyformamido-Linkage Instead of a Phosphodiester Group," Journal of the Chemical Society, vol. 14, pp. 1684-1686, (1974).
Iversen, "Phosphorodiamidate Morpholino Oligomers: Favorable Properties for Sequence-Specific Gene Inactivation," Current Opinion in Molecular Therapeutics, vol. 3(3), pp. 235-238, (2001).
Martin et al., "Ein Neuer Zugang Zu 2'-O-Alkylribonucleosiden Und Eigenschaften Deren Oligonucleotide," Helvetica Chimica Acta, vol. 78, pp. 486-504, (1995).
McDonald et al., "The 6-Minute Walk Test in Duchenne/Becker Muscular Dystrophy: Longitudinal Observations," Muscle & Nerve, vol. 42(6), pp. 966-974, (2010).
Nuttall et al., "Immunoglobulin $V_H$ Domains and Beyond: Design and Selection of Single-Domain Binding and Targeting Reagents," Current Pharmaceutical Biotechnology, vol. 1(3), pp. 253-263, (2000).
Revankar et al., "DNA with Altered Bases," Comprehensive Natural Products Chemistry, vol. 7(9), p. 313-339, (1999).
Rodino-Klapac et al., "AAV-Mediated Gene Therapy to the Isolated Limb in Rhesus Macaques," Methods in Molecular Biology, vol. 709(19), pp. 287-298, (2011).

Suwanmanee et al., "Restoration of Human β-Globin Gene Expression in Murine and Human. IVS2-654 Thalassemic Erythroid Cells by Free Uptake of Antisense Oligonucleotides," Molecular Pharmacology, vol. 62(3), pp. 545-553, (2002).
Van Deutekom et al., "Antisense-Mediated Exon Skipping as a Gene Correction Therapy for Duchenne Muscular Dystrophy," Journal of the Neurological Sciences, vol. 199, pp. S75-S76, (2002).
USPTO; Non-Final Office Action dated Dec. 14, 2018 in U.S. Appl. No. 16/129,680.
Aartsma-Rus et al., "Theoretic Applicability of Antisense-Mediated Exon Skipping for Duchenne Muscular Dystrophy Mutations," Human Mutation, vol. 30(3), pp. 293-299, (2009).
Abbs et al., "Best Practice Guidelines on Molecular Diagnostics in Duchenne/Becker Muscular Dystrophies," Neuromuscular Disorders, vol. 20(6), pp. 422-427, (2010).
Agrawal, "Importance of Nucleotide Sequence and Chemical Modifications of Antisense Oligonucleotides," Biochimica et Biophysica Acta, vol. 1489, pp. 53-68, (1999).
Alter et al., Systemic Delivery of Morpholino Oligonucleotide Restores Dystrophin Expression Bodywide and Improves Dystrophic Pathology, Nat Med, vol. 12, pp. 175-177, (2006).
Altschul et al., "Gapped BLAST and PSI-BLAST: A New Generation of Protein Database Search Programs," Nucleic Acids Research, vol. 25(17), p. 3389-3402, (1997).
Amantana et al., "Pharmacokinetics and Biodistribution of Phosphorodiamidate Morpholino Antisense Oligomers," Current Opinion in Pharmacology, vol. 5, pp. 550-555, (2005).
Benner et al., "Synthetic Biology," Nature Reviews Genetics, vol. 6(7), pp. 553-543, (2005).
Berridge et al., "Characterization of the Cellular Reduction of 3-(4,5-Dimethylthiazol-2-yl)-2,5-Diphenyltetrazolium Bromide (MTT): Subcellular Localization, Substrate Dependence, and Involvement of Mitochondrial Electron Transport in MTT Reduction," Archive Biochemistry Biophysics, vol. 303, pp. 747-482, (1993).
Bogdanovich et al., "Myostatin Propeptide-Mediated Amelioration of Dystrophic Pathophysiology," FASEB J, vol. 19, pp. 543-549.
Bowles et al., "Phase 1 Gene Therapy for Duchenne Muscular Dystrophy Using a Translational Optimized AAV Vector," Molecular Therapy, vol. 20(2), pp. 443-455, (2012).
Brown et al., "Dystrophic Phenotype Induced In Vitro by Antibody Blockade of Muscle Alpha-Dystroglycan-Laminin Interaction," Journal of Cell Science, vol. 112(2), pp. 209-216, (1999).
Fairbrother et al., "RESCUE-ESE Identifies Candidate Exonic Splicing Enhancers in Vertebrate Exons," Nucleic Acids Research, vol. 32, pp. W187-W190, (2004).
Carnac et al., "Myostatin: Biology and Clinical Relevance," Mini Reviews in Medicinal Chemistry, vol. 6, pp. 765-770, (2006).
Cartegni et al., "Listening to Silence and Understanding Nonsense: Exonic Mutations that Affect Splicing," Nat Rev Genet, vol. 3, pp. 285-298, (2002).
Cartegni et al., "ESEfinder: A Web Resource to Identify Exonic Splicing Enhancers," Nucleic Acids Res, vol. 31, pp. 3568-3571, (2003).
Chasin et al., "Computational Definition of Sequence Motifs Governing Constitutive Exon Splicing," Genes & Development, vol. 18, pp. 1241-1250, (2004).
Chiu et al., "siRNA Function in RNAi: A Chemical Modification Analysis," RNA, vol. 9, pp. 1034-1048, (2003).
Collins & Morgan, "Duchenne's Muscular Dystrophy: Animal Models used to Investigate Pathogenesis and Develop Therapeutic Strategies," International Journal of Experimental Pathology, vol. 84(4), pp. 165-172, (2003).
Dennler et al., "Direct Binding of Smad3 and Smad4 to Critical TGF Beta-Inducible Elements in the Promoter of Human Plasminogen Activator Inhibitor-Type 1 Gene," EMBO J, vol. 17, pp. 3091-3100, (1998).
Deveraux et al., "A Comprehensive Set of Sequence Analysis Programs for the VAX," Nucleic Acids Research, vol. 12, pp. 387-395, (1984).
Dokka et al., "Novel Non-Endocytic Delivery of Antisense Oligonucleotides," Advanced Drug Delivery Reviews, vol. 44(1), pp. 35-49, (2000).

(56) References Cited

OTHER PUBLICATIONS

Dominski et al., "Restoration of Correct Splicing in Thalassemic PremRNA by Antisense Oligonucleotides," Proceedings of the National Academy of Sciences USA, vol. 90, pp. 8673-8677, (1993).
Dumonceaux et al., "Combination of Myostatin Pathway Interference and Dystrophin Rescue Enhances Tetanic and Specific Force in Dystrophic MDX Mice," Molecular Therapy, vol. 18, pp. 881-887, (2010).
Dunckley et al., "Modification of Splicing in the Dystrophin Gene in Cultured MDX Muscle Cells by Antisense Oligoribonucleotides," Human Molecular Genetics, vol. 7, pp. 1083-1090, (1998).
Fairbrother et al., "Predictive Identification of Exonic Splicing Enhancers in Human Genes," Science, vol. 297, pp. 1007-1013, (2002).
Fakhfakh et al., "Blocking the Myostatin Signal with a Dominant Negative Receptor Improves the Success of Human Myoblast Transplantation in Dystrophic Mice," Molecular Therapy, vol. 19, pp. 204-210, (2011).
Foster, "Eye Evolution: Two Eyes can be Better than One," Current Biology, vol. 19, pp. R208-R210, (2009).
Foster et al., "Adeno-Associated Virus-8-Mediated Intravenous Transfer of Myostatin Propeptide Leads to Systemic Functional Improvements of Slow but Not Fast Muscle," Rejuvenation Research, vol. 12, pp. 85-94, (2009).
Friedman et al., "Correction of Aberrant Splicing of the Cystic Fibrosis Transmembrane Conductance Regulator (CFTR) Gene by Antisense Oligonucleotides," Journal of Biological Chemistry, vol. 274, pp. 36193-36199, (1999).
Gebski et al., "Terminal Antisense Oligonucleotide Modifications Can Enhance Induced Exon Skipping," Neuromuscular Disorders, vol. 15, pp. 622-629, (2005).
Gebski et al., "Morpholino Antisense Oligonucleotide Induced Dystrophin Exon 23 Skipping in Mdx Mouse Muscle," Human Molecular Genetics, vol. 12, pp. 1801-1811, (2003).
Ghahramani et al., "RNAi-Mediated Knockdown of Dystrophin Expression in Adult Mice does not Lead to Overt Muscular Dystrophy Pathology," Hum Mol Genet, vol. 17, pp. 2622-2632, (2008).
Graham et al., "Towards a Therapeutic Inhibition of Dystrophin Exon 23 Splicing in MDX Mouse Muscle Induced by Antisense Oligoribonucleotides (Splicomers): Target Sequence Optimisation using Oligonucleotide Arrays," Journal of Gene Medicine, vol. 6, pp. 1149-1158, (2004).
Grobet et al., "A Deletion in the Bovine Myostatin Gene Causes the Double-Muscled Phenotype in Cattle," Nature Genetics, vol. 17, pp. 71-74, (1997).
Haidet et al., Long-Term Enhancement of Skeletal Muscle Mass and Strength by Single Gene Administration of Myostatin Inhibitors, Proceedings of the National Academy of Sciences USA, vol. 105, pp. 4318-4322, (2008).
Hausen et al., "Ribonuclease H. An Enzyme Degrading the RNA Moiety of DNA-RNA Hybrids," European Journal of Biochemistry, vol. 14, pp. 278-283, (1970).
Hirao, "Unnatural Base Pair Systems for DNA/RNA-Based Biotechnology," Current Opinion in Chemical Biology, vol. 10(6), pp. 622-627, (2006).
Hudson et al., "High Avidity scFv Multimers; Diabodies and Triabodies," Journal of Immunological Methods, vol. 231(1), pp. 177-189, (1999).
Iyer et al., "The Automated Synthesis of Sulfur-Containing Oligodeoxyribonucleotides Using 3H-1,2-Benzodithiol-3-One 1,1-Dioxide as a Sulfur-Transfer Reagent," Journal of Organic Chemistry, vol. 55, pp. 4693-4699, (1990).
Jearawiriyapaisarn et al., "Long-Term Improvement in MDX Cardiomyopathy After Therapy with Peptide-Conjugated Morpholino Oligomers," Cardiovascular Research, vol. 85, pp. 444-453, (2010).
Kang et al., "Antisense-Induced Myostatin Exon Skipping Leads to Muscle Hypertrophy in Mice Following Octa-guanidine Morpholino Oligomer Treatment," Molecular Therapy, vol. 19(1), pp. 159-164, (2011).

Kinali et al., "Local Restoration of Dystrophin Expression with the Morpholino Oligomer AVI-4658 in Duchenne Muscular Dystrophy: A Single-Blind, Placebo-Controlled, Dose-Escalation, Proof-of-Concept Study," Lancet Neurol, vol. 8, pp. 918-928, (2009).
Kool, "Replacing the Nucleobases in DNA with Designer Molecules," Accounts of Chemical Research, vol. 35(11), pp. 936-943, (2002).
Koppanati et al., "Improvement of the MDX Mouse Dystrophic Phenotype by Systemic in Utero AAV8 Delivery of a Minidystrophin Gene," Gene Therapy, vol. 17(11), pp. 1355-1362, (2010).
Krainer et al., "Disruption if an SF2/ASF-Dependent Exonic Splicing Enhancer in SMN2 Causes Spinal Muscular Atrophy in the Absence of SMN1," Nature Genetics, vol. 30, pp. 377-384, (2002).
Kruegar et al., "Synthesis and Properties of Size-Expanded DNAs: Toward Designed, Functional Genetic Systems," Accounts of Chemical Research, vol. 40(2), pp. 141-150, (2007).
Langley et al., "Myostatin Inhibits Myoblast Differentiation by Down-Regulating MyoD Expression," J Biol Chem, vol. 277, pp. 49831-49840, (2002).
Lappalainen et al., "Cationic Liposomes Mediated Delivery of Antisense Oligonucleotides Targeted to HPV 16 E7 mRNA in CaSki Cells," Antiviral Research, vol. 23, p. 119-130, (1994).
Limbach et al., "Summary: The Modified Nucleosides of RNA," Nucleic Acids Research, vol. 22(12), pp. 2183-2196, (1994).
Martin et al., "Overexpression of Galgt2 in Skeletal Muscle Prevents Injury Resulting from Eccentric Contractions in Both MDX and Wild-Type Mice," American Journal of Physiology-Cell Physiology, vol. 296, pp. 476-488, (2009).
McDonald et al., "The 6-Minute Walk Test as a New Outcome Measure in Duchenne Muscular Dystrophy," Muscle & Nerve, vol. 41(4), pp. 500-510, (2010).
McGreevy et al., "Animal Models of Duchenne Muscular Dystrophy: From Basic Mechanisms to Gene Therapy," Disease Models & Mechanisms, vol. 8(3), pp. 195-213, (2015).
Mertes et al., "Synthesis of Carbonate Analogs of Dinucleosides. 3-Thymidinyl 5-Thymidinyl Carbonate, 3-Thymidinyl 5-(5-Fluoro-2-Deoxyuridinyl) Carbonate, and 3-(5-Fluoro-2-Deoxyuridinyl) 5-Thymidinyl Carbonate," J Med Chem, vol. 12(1), pp. 154-157, (1969).
Miyada et al., "Oligomer Hybridization Techniques," Methods in Enzymology, vol. 154, pp. 94-107, (1987).
Morcos et al., "Vivo-Morpholinos: A Non-Peptide Transporter Delivers Morpholinos into a Wide Array of Mouse Tissues," Biotechniques, vol. 45 pp. 613-614, 616, 618 passim, (2008).
Mourich et al., "Antisense Targeting of cFLIP Sensitizes Activated T Cells to Undergo Apoptosis and Desensitizes Responses to Contact Dermatitis," Journal of Investigative Dermatology, vol. 129(8), pp. 1945-1953, (2009).
Muyldermans et al., "Recognition of Antigens by Single-Domain Antibody Fragments: The Superfluous Luxury of Paired Domains," Trends in Biochemical Sciences, vol. 26(4), pp. 230-235, (2001).
Nielsen et al., "Sequence-selective recognition of DNA by strand displacement with a thymine-substituted polyamide," Science, vol. 254(5037), pp. 1497-1500, (1991).
Obika et al., "Synthesis of 2'-O,4'-C-Methyleneuridine and -Cytidine. Novel Bicyclic Nucleosides having a Fixed C3, -Endo Sugar Puckering," Tetrahedron Letters, vol. 38(50), p. 8735, (1997).
Obika et al., "Stability and Structural Features of the Duplexes Containing Nucleoside analogues with a fixed N-Type Conformation, 2'-O,4'-C-Mehtyleneribonucleosides," Tetrahedron Letters, vol. 39(30), p. 5401-5404, (1998).
Obika et al., "Synthesis and Properties of 3'-Amino-2',4'-BNA, A Bridged Nucleic Acid with a N3'-→P5' Phosphoramidate Linkage," Bioorganic & Medicinal Chemistry, vol. 16(20), p. 9230, (2008).
Odom et al., "Gene Therapy of MDX Mice with Large Truncated Dystrophins Generated by Recombination Using rAAV6," Molecular Therapy, vol. 19(1), pp. 36-45, (2011).
Okada et al., "Current Challenges and Future Directions in Recombinant AAV-Mediated Gene Therapy of Duchenne Muscular Dystrophy," Pharmaceuticals, vol. 6(7), pp. 813-836, (2013).

(56) References Cited

OTHER PUBLICATIONS

Paola Rimessi et al., "Cationic PMMA Nanoparticles Bind and Deliver Antisense Oligoribonucleotides Allowing Restoration of Dystrophin expression in the MDX Mouse," Molecular Therapy, vol. 17(5), pp. 820-827, (2009).
Patel et al., "The Function of Myostatin and Strategies of Myostatin Blockade-New Hope for Therapies Aimed at Promoting Growth of Skeletal Muscle," Neuromuscular Disorders, vol. 15, pp. 117-126, (2005).
Poljak, "Production and Structure of Diabodies," Structure, vol. 2(12), pp. 1121-1123, (1994).
Popplewell et al., "Design of Phosphorodiamidate Morpholino Oligomers (PMOs) for the Induction of Exon Skipping of the Human DMD Gene," Molecular Therapy, vol. 17, pp. 554-561, (2009).
Popplewell et al., "Comparative Analysis of Antisense Oligonucleotide Sequences Targeting Exon 53 of the Human DMD Gene: Implications for Future Clinical Trials," Neuromuscular Disorder, vol. 20, pp. 102-110, (2010).
Qiao et al., "Myostatin Propeptide Gene Delivery by Adeno-Associated Virus Serotype 8 Vectors Enhances Muscle Growth and Ameliorates Dystrophic Phenotypes in MDX Mice," Human Gene Therapy, vol. 19, pp. 241-254, (2008).
Reichmann et al., "Single Domain Antibodies: Comparison of Camel VH and Camelised Human VH Domains," Journal of Immunological Methods, vol. 231, pp. 25-38, (1999).
Rodino-Klapac et al., "Persistent Expression of FLAG-Tagged Micro-Dystrophin in Nonhuman Primates Following Intramuscular and Vascular Delivery," Molecular Therapy, vol. 18(1), pp. 109-117, (2010).
Romesberg et al., "Beyond A, C, G and T: Augmenting Nature's Alphabet," Current Opinion in Chemical Biology, vol. 7(6), pp. 727-733, (2003).
Rondon et al., "Intracellular Antibodies (Intrabodies) for Gene Therapy of Infectious Diseases," Annual Review of Microbiology, vol. 51, pp. 257-283, (1997).
Sazani et al., "Short-Term and Long-Term Modulation of Gene Expression by Antisense Therapeutics," Current Opinion in Biotechnology, vol. 13, pp. 468-472, (2002).
Sazani et al., "Nuclear Antisense Effects of Neutral, Anionic and Cationic Oligonucleotide Analogs," Nucleic Acids Research, vol. 29, pp. 3965-3974, (2001).
Schuelke et al., "Myostatin Mutation Associated with Gross Muscle Hypertrophy in a Child," N. England Journal of Medicine, vol. 350, pp. 2682-2688, (2004).
Shin et al., "Microdystrophin Ameliorates Muscular Dystrophy in the Canine Model of Duchenne Muscular Dystrophy," Molecular Therapy, vol. 21(4), pp. 750-757, (2013).
Sierakowska et al., "Repair of Thalassemic Human β-Globin mRNA in Mammalian Cells by Antisense Oligonucleotides," Proceedings in the National Academy of Sciences USA, vol. 93, pp. 12840-12844, (1996).
Smith et al., "An Increased Specificity Score Matrix for the Prediction of SF2/ASF-Specific Exonic Splicing Enhancers," Hum Mol Genet, vol. 15, pp. 2490-2508, (2006).
Spitali et al., "Accurate Quantification of Dystrophin mRNA and Exon Skipping Levels in Duchenne Muscular Dystrophy," Lab Invest, vol. 90, pp. 1396-1402, (2010).
Stojdl et al., "SR Protein Kinases. The Splice of Life," Biochemistry and Cell Biology—Biochimie Et Biologie Cellulaire, vol. 77, pp. 293-298, (1999).
Szabo et al., "A Deletion in the Myostatin Gene Cause the Compact (Cmpt) Hypermuscular Mutation in Mice," Mammalian Genome, vol. 9, pp. 671-672, (1998).
Tries et al., "GDF-8 Propeptide Binds to GDF-8 and Antagonizes Biological Activity by Inhibiting GDF-8 Receptor Binding," Growth Factors, vol. 18, pp. 251-259, (2001).
Thomas et al., "Myostatin, A Negative Regulator of Muscle Growth, Functions by Inhibiting Myoblast Proliferation," J Biol Chem, vol. 275, pp. 40235-40243, (2000).
Todorovska et al., "Design and Application of Diabodies, Triabodies and Tetrabodies for Cancer Targeting," Journal of Immunological Methods, vol. 248(1), pp. 47-66, (2001).
Uhlmann et al., "Antisense Oligomers: A New Therapeutics Principle," Chemical Reviews, vol. 90(4), pp. 544-584, (1990).
Van Deutekom et al., "Local Dystrophin Restoration with Antisense Oligonucleotide PRO051," N England Journal of Medicine, vol. 357, pp. 2677-2686, (2007).
Van Duetekom et al., "Advances in Duchenne Muscular Dystrophy Gene Therapy," Nat Rev Genet, vol. 4, pp. 774-783, (2003).
Verhaart et al., "Gene Therapy for Duchenne Muscular Dystrophy," Current Opinion in Neurology, vol. 25(5), pp. 588-596, (2012).
Vincent et al., "Long-Term Correction of Mouse Dystrophic Degeneration by Adenovirus-Mediated Transfer of a Minidystrophin Gene," Nature Genetics, vol. 5, pp. 130-134, (1993).
Wagner et al., "A Phase I/Iitrial of MYO-029 in Adult Subjects with Muscular Dystrophy," Ann Neurol, vol. 63, pp. 561-571, (2008).
Weinstein et al., "RNAi Nanomedicines: Challenges and Opportunities within the Immune System," Nanotechnology, vol. 21, p. 232001, (2010).
Wengel et al., "LNA (Locked Nucleic Acids): Synthesis and High-Affinity Nucleic Acid Recognition," Chemical Communications, Issue 4, pp. 455-456, (1998).
Wengel et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, vol. 54(14), p. 3607-3630, (1998).
Wengel et al., "Synthesis of 3'-C- and 4'-C-Branched Oligodeoxynucleotides and the Development of Locked Nucleic Acid (LNA)," Accounts of Chemical Research, vol. 32(4), p. 301, (1999).
Whittemore et al "Inhibition of Myostatin in Adult Mice Increases Skeletal Muscle Mass and Strength," Biochemical and Biophysical Research Communications, vol. 300, pp. 965-971, (2003).
Williams, S.A. "Cationic Lipids Reduce Time and Dose of C-Myc Antisense Oligodeoxynucleotides Required to Specifically Inhibit Burkitt's Lymphoma Cell Growth," Leukemia, vol. 10(12), pp. 1980-1989, (1996).
Wilton et al., "Antisense Oligonucleotides in the Treatment of Duchenne Muscular Dystrophy: Where are we now?" Disorders, vol. 15, pp. 399-402, (2005).
Wilton et al., "Improved Antisense Oligonucleotide Induced Exon Skipping in the MDX Mouse Model of Muscular Dystrophy," Journal of Gene Medicine, vol. 4, pp. 644-654, (2002).
Wilton et al., "Antisense Oligonucleotide-Induced Exon Skipping Restores Dystrophin Expression In Vitro in a Canine Model of DMD," Gene Therapy, vol. 13, pp. 1373-1381, (2006).
Wu et al., "Receptor-Mediated In Vitro Gene Transformation by a Soluble DNA Carrier System," Journal of Biological Chemistry, vol. 262, pp. 4429-4432, (1987).
Wu et al., "Octa-Guanidine Morpholino Restores Dystrophin Expression in Cardiac and Skeletal Muscles and Ameliorates Pathology in Dystrophic MDX Mice," Molecular Therapy, vol. 17, pp. 864-871, (2009).
Xu et al., "Postnatal Overexpression of the CT GalNAc Transferase Inhibits Muscular Dystrophy in MDX Mice Without Altering Muscle Growth or Neuromuscular Development: Evidence for a Utrophin-Independent Mechanism," Neuromuscular Disorders, vol. 17, pp. 209-220, (2007).
Yamada et al., "Synthesis of 2'-O-[2-(Methylcarbamoyl)Ethyl]Ribonucleosides Using Oxa—Michael Reaction and Chemical and Biological Properties if Oligonucleotide Derivatives Incorporating These Modified Ribonucleosides," Journal of Organic Chemistry, vol. 76(9), pp. 3042-3053, (2011).
Yang et al., "A Retrovirus-Based System to Stably Silence GDF-8 Expression and Enhance Myogenic Differentiation in Human Rhabdomyosarcoma Cells," Journal of Gene Medicine, vol. 10, pp. 852-833, (2008).
Yoo et al., "2'-O-Methyl-Modified Phosphorothioate Antisense Oligonucleotides have Reduced Non-Specific Effects In Vitro," Nucleic Acids Research, vol. 32(6), pp. 2008-2016, (2004).

(56) References Cited

OTHER PUBLICATIONS

Zamecnik et al., "Inhibition of Rous Sarcoma Virus Replication and Cell Transformation by a Specific Oligodeoxynucleotide," Proceedings of the National Academy of Sciences USA, vol. 75, pp. 280-284, (1978).
Zhang et al., "Computational Definition of Sequence Motifs Governing Constitutive Exon Splicing," Genes & Development, vol. 18, pp. 1241-1250, (2004).
Zhang et al., "Computational Searches for Splicing Signals," Methods, vol. 37, pp. 292-305, (2005).
Zhu et al., "Dominant Negative Myostatin Produces Hypertrophy without Hyperplasia in Muscle," FEBS Letters, vol. 474, pp. 71-75, (2000).
EPO; Extended Search Report dated Nov. 20, 2018 in EP Application No. 16765858.2.
Malerba et al., "Dual Myostatin and Dystrophin Exon Skipping by Morpholino Nucleic Acid Oligomers Conjugated to a Cell-Penetrating Peptide is a Promising Therapeutic Strategy for the Treatment of Duchenne Muscular Dystrophy," Molecular Therapy—Nucleic Acids, vol. 1, p. e62, (Dec. 2012).
CA; Office Action dated Mar. 5, 2018 in CA Application No. 2596506.
EPO; Extended Search Report dated May 3, 2019 in EP Application No. 16854468.2.
IL; Office Action dated Jul. 8, 2019 in the IL Application No. 258069.
Kernaladewi et al., "Dual Exon Skipping in Myostatin and Dystrophin for Duchenne Muscular Dystrophy," BMC Medical Genomics, vol. 4, p. 36-45, (2011).
Lu-Nguyen et al., "Combination Antisense Treatment for Destructive Exon Skipping of Myostatin and Open Reading Frame Rescue of Dystrophin in Neonatal mdx Mice," Molecular Therapy, vol. 23(8), pp. 1341-1348, (Aug. 2015).
Lu-Nguyen, "Mouse Open-Field Behavioral Activity," Supplementary Materials and Methods, 2 Pages (2015).
USPTO; Requirement for Restriction dated May 3, 2019 in U.S. Appl. No. 15/765,466.
USPTO; Notice of Allowance dated May 13, 2019 in U.S. Appl. No. 16/129,680.
PCT; International Search Report for Application No. PCT/US2006/004797 dated Feb. 22, 2007.
CA; Notice of Allowance dated Apr. 4, 2019 in CA Application No. 2596506.
USPTO; Notice of Allowance dated Dec. 26, 2019 in the U.S. Appl. No. 15/986,746.
USPTO; Notice of Allowance dated Jan. 21, 2020 in the U.S. Appl. No. 16/539,732.
USPTO; Final Office Action dated May 19, 2020 in the U.S. Appl. No. 15/765,466.
JP; Office Action dated Feb. 19, 2020 in the JP Application No. 2017548452.
USPTO; Non-Final Office Action dated Jul. 23, 2020 in the U.S. Appl. No. 16/852,933.
USPTO; Restriction Requirement dated May 27, 2020 in the U.S. Appl. No. 16/852,933.
USPTO; Notice of Allowance dated Nov. 16, 2020 in the U.S. Appl. No. 16/852,933.
JP; Japanese Office Action dated Oct. 29, 2020 in the JP Application No. 2017-548452.
EP; Examination Report dated Sep. 23, 2020 in the EP Application No. 16765858.2.
JP; Japanese Office Action dated Aug. 28, 2020 in the JP Application No. 2018-517603.

\* cited by examiner

ANTISENSE-INDUCED EXON EXCLUSION IN MYOSTATIN

CROSS-REFERENCE TO RELATED APPLICATIONS

This application claims priority to U.S. Provisional Patent Application Ser. No. 62/135,048 filed Mar. 18, 2015, and U.S. Provisional Patent Application Ser. No. 62/162,571 filed May 15, 2015, which are incorporated herein by reference in their entireties.

STATEMENT REGARDING SEQUENCE LISTING

The Sequence Listing associated with this application is provided in text format, and is hereby incorporated by reference into the specification. The name of the text file containing the Sequence Listing is 6746300100_SL.txt.

BACKGROUND OF THE INVENTION

Field of the Disclosure

Antisense oligomers and related compositions and methods are disclosed, including methods for decreasing expression levels of functional human myostatin mRNA, methods for treating muscular dystrophy and related disorders related to the expression of myostatin, and methods for decreasing expression levels of exon 2 in myostatin pre-mRNA transcript, thereby reducing the levels of functional myostatin protein encoded by the myostatin gene.

Description of the Related Art

Muscular dystrophy is an inherited disorder that involves progressive muscle weakness and loss of muscle mass. Myostatin, also referred to as growth differentiation factor 8 (GDF-8), belongs to the transforming growth factor-beta (TGF-β) superfamily. Myostatin is a protein encoded by the MSTN gene, which is largely expressed in human skeletal muscle and acts as a negative regulator of muscle growth. For example, in mice engineered to lack the myostatin gene demonstrate the development of twice the muscle mass of normal mice (McPherron et al., (1997), Nature 387:83-90).

Myostatin blockage has been targeted as a potential therapeutic target for the treatment of muscular dystrophy disorders. Previous studies have focused on blocking myostatin protein production either at the gene level or using antibodies directed to the myostatin protein. Antisense technology has been utilized to target the myostatin gene to prevent its expression at the cellular level. Myostatin-inhibiting genes such as growth and differentiation factor-associated serum protein-1 (GASP-1), follistatin-related gene (FLRG) and myostatin propeptide have been investigated as potential therapeutics and have shown an increase in muscle mass in treated animals (Kang J. et al., (2011) Mol. Ther. 19(1): 159-64). However, this approach may have safety concerns over possible genotoxicity.

Antisense technology, used mostly for RNA down regulation, recently has been adapted to alter the splicing process of a precursor messenger RNA (pre-mRNA). Pre-mRNA is an immature single strand of messenger RNA synthesized from a DNA transcript through a process known as transcription. The pre-mRNA transcript comprises two different segment types, introns and exons. Introns are removed in a process called splicing, which is generally performed by a spliceosome complex. The remaining exons are joined together and become part of the final, mature mRNA molecule.

The precise process of intron/exon splicing involves various structural elements within the intron region. These include an intron splice donor site, located at the 5' end of the intron, a branch site, located near the 3' end of the intron, and a splice acceptor site, located at the 3' end of the intron. The splice donor site generally includes a conserved GU sequence at the 5' end of the exon/intron junction. The splice acceptor site generally includes an AG sequence at the 3' end of the intron/exon junction.

Variations in the splicing process can create variations in the resultant mRNA by varying the exon composition within the mRNA, a process often referred to as alternative splicing. Alternative splicing can occur in many ways. Exons may be extended or skipped. Portions of introns may be retained. Alternative splicing increases the coding potential of the human genome by producing multiple proteins from a single gene. Inappropriate alternative splicing is also associated with a growing number of human diseases.

Antisense oligonucleotides can be utilized to modulate pre-mRNA splicing by masking certain regulatory sites called exonic splicing enhancer (ESE) motifs. Masking these sequences with appropriate antisense oligonucleotides can result in an exon being spliced out together with neighboring introns. This exon skipping has been used clinically to partly correct the mutation in the dystrophin gene associated with Duchenne muscular dystrophy (DMD) and convert DMD to the milder form Becker muscular dystrophy (Cartegni, L. et al., (2002), Nat Rev Genet 3:285-298).

Accordingly, novel antisense oligonucleotides and methods of modulating the expression of myostatin pre-mRNA and functional myostatin protein as described herein are believed to be advantageous.

SUMMARY OF THE INVENTION

In various embodiments, compositions and methods for decreasing the expression of functional myostatin protein are provided. In various embodiments, variously described antisense oligomers for decreasing expression levels exons of a human myostatin coding mRNA are further provided.

Various aspects include an antisense oligomer of 12 to 40 subunits, optionally comprising at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an intron/exon splice junction of human myostatin pre mRNA. In various embodiments, the contiguous nucleotides include the splice intron/exon junction. In further embodiments, the splice junctions may be selected from the splice junction at intron 1/exon 2 (e.g., SEQ ID NO: 6) or exon 2/intron 2 (e.g., SEQ ID NO: 7, or SEQ ID NO: 8).

Additional aspects include antisense oligomers of 12 to 40 subunits that specifically hybridize to a target region spanning an intron/exon splice junction of human myostatin pre-mRNA. The splice junctions are optionally selected from splice junctions at the intersection of intron 1/exon 2 and exon 2/intron 2. In embodiments, the splice junction of intron 1/exon 2 is selected from the splice junction within SEQ ID NO: 6; the splice junction of exon 2/intron 2 is selected from the splice junction within SEQ ID NO: 7, or SEQ ID NO: 8.

Additional aspects include antisense oligomers having a nucleotide analog subunit comprising a modified sugar moiety. In various embodiments, at least one modified sugar moiety includes a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

Additional aspects include antisense oligomers having a nucleotide analog subunit comprising a modified internucleoside linkage. In various embodiments, the modified internucleoside linkage is selected from a phosphorothioate internucleoside linkage, a phosphoramidate internucleoside linkage, and a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

Additional aspects include antisense oligomers having a nucleotide analog subunit comprising at least one combination of a modified sugar moiety and a modified internucleoside linkage. In various embodiments, one or more subunits are selected from a morpholino subunit optionally substituted with a phosphoramidate internucleoside linkage, a phosphorodiamidate internucleoside linkage, or a phosphorothioate internucleoside linkage, a 2' O-methyl subunit optionally substituted with a phosphoramidate internucleoside linkage, a phosphorodiamidate internucleoside linkage, or a phosphorothioate internucleoside linkage, a 2'O-methoxyethyl subunit optionally substituted with a phosphoramidate internucleoside linkage, a phosphorodiamidate internucleoside linkage, or a phosphorothioate internucleoside linkage, a 2'-fluoro subunit optionally substituted with a phosphoramidate internucleoside linkage, a phosphorodiamidate internucleoside linkage, or a phosphorothioate internucleoside linkages, a 2'O,4'C-ethylene-bridged nucleic acid subunit optionally substituted with a phosphoramidate internucleoside linkage, a phosphorodiamidate internucleoside linkage, or a phosphorothioate internucleoside linkage, a 2'-O-[2-(N-methylcarbamoyl)ethyl] subunit optionally substituted with a phosphoramidate internucleoside linkage, a phosphorodiamidate internucleoside linkage, or a phosphorothioate internucleoside linkage, a tricyclo-DNA subunit optionally substituted with a phosphoramidate internucleoside linkage, a phosphorodiamidate internucleoside linkage, or a phosphorothioate internucleoside linkage, a locked nucleic acid subunit optionally substituted with a phosphoramidate internucleoside linkage, a phosphorodiamidate internucleoside linkage, or a phosphorothioate internucleoside linkage, a morpholino subunit further comprising a phosphorodiamidate internucleoside linkage where a phosphorous atom of the phosphorodiamidate is covalently bonded to the nitrogen atom of the morpholine ring, and is covalently bonded to a (1,4-piperazin)-1-yl moiety or to a substituted (1,4-piperazin)-1-yl moiety, a morpholino subunit further comprising a phosphorodiamidate internucleoside linkage where a phosphorus atom of the phosphorodiamidate is covalently bonded to the nitrogen atom of the morpholine ring, and is covalently bonded to a 4-aminopiperdin-1-yl moiety or a substituted 4-aminopiperdin-1-yl moiety, a ribose sugar subunit substituted with a phosphorothioate internucleoside or a phosphoramidate internucleoside linkage, a deoxyribose sugar subunit substituted with a phosphorothioate internucleoside linkage or a phosphoramidate internucleoside linkage, a peptide nucleic acid subunit optionally substituted, or any combination of the foregoing.

In various aspects and embodiments, antisense oligomers further comprise a peptide covalently bonded to the antisense oligomer. In various embodiments, an arginine-rich cell-penetrating peptide is covalently bonded to the 3' or the 5' end of the antisense oligomer.

In various embodiments, the antisense oligomer specifically hybridizes to a myostatin target region. The target region may comprise splice junction sequence(s) set forth in Table 1. In various embodiments, the antisense oligomer specifically hybridizes to a target region spanning an intron/exon splice junction of the human myostatin pre-mRNA.

In various embodiments, the antisense oligomer comprises any of a targeting sequence set forth in Table 2, a fragment of at least 12 contiguous nucleotides of a targeting sequence in Table 2, or a variant having at least 90% sequence identity to a targeting sequence in Table 2. In further embodiments, the antisense oligomer consists or consists essentially of a targeting sequence set forth in Table 2.

In various aspects and embodiments, a nucleobase of a nucleotide subunit is independently selected from adenine, guanine, thymine, uracil, cytosine, inosine, hypoxanthine, 2,6-diaminopurine, 5-methyl cytosine, C5-propynyl-modified pyrimidines, and 10-(9-(aminoethoxy)phenoxazinyl).

In various aspects, the antisense oligomer of the disclosure is a compound of formula (I):

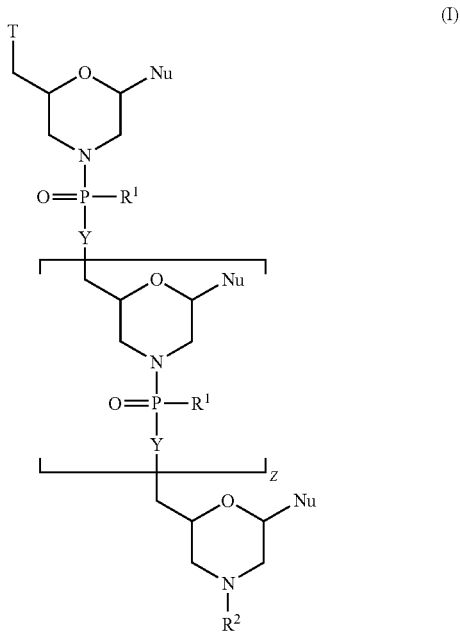

or a pharmaceutically acceptable salt thereof, where:

each Nu is a nucleobase which taken together forms a targeting sequence;

Z is an integer from 10 to 38;

each Y is independently selected from O and —NR⁴ where each R⁴ is independently selected from H, $C_1$-$C_6$ alkyl, aralkyl, —C(=NH)NH₂, —C(O)(CH₂)ₙNR⁵C(=NH)NH₂, —C(O)(CH₂)₂NHC(O)(CH₂)₅NR⁵C(=NH)NH₂, and G, where R⁵ is selected from H and $C_1$-$C_6$ alkyl and n is an integer from 1 to 5;

T is selected from OH and a moiety of the formula:

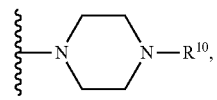

where:
A is selected from —OH and —N(R⁷)₂ where:
each R⁷ is independently selected from H and $C_1$-$C_6$ alkyl, and
R⁶ is selected from OH, —N(R⁹)CH₂C(O)NH₂, and a moiety of the formula:

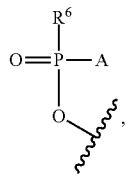

where:
R⁹ is selected from H and $C_1$-$C_6$ alkyl; and
R¹⁰ is selected from G, —C(O)—R¹¹OH, acyl, trityl, 4-methoxytrityl, —C(=NH)NH₂, —C(O)(CH₂)ₘNR²C(=NH)NH₂, and —C(O)(CH₂)₂NHC(O)(CH₂)NR¹²C(=NH)NH₂, where:
m is an integer from 1 to 5,
R¹¹ is of the formula —(O-alkyl)ᵧ— where y is an integer from 3 to 10 and each of the y alkyl groups is independently selected from $C_2$-$C_6$ alkyl; and
R¹² is selected from H and $C_1$-$C_6$ alkyl;

each instance of R¹ is independently selected from:
—N(R¹³)₂ where each R³ is independently selected from H and $C_1$-$C_6$ alkyl;
a moiety of formula (II):

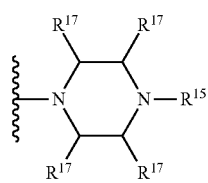

where:
R¹⁵ is selected from H, G, $C_1$-$C_6$ alkyl, —C(=NH)NH₂,
—C(O)(CH₂)qNR¹⁸C(=NH)NH₂, and
—C(O)(CH₂)₂NHC(O)(CH₂)₅NR¹⁸C(=NH)NH₂, where:

R¹⁸ is selected from H and $C_1$-$C_6$ alkyl; and
q is an integer from 1 to 5; and
each R¹⁷ is independently selected from H and methyl; and a moiety of formula (III):

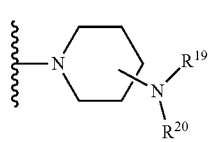

where:
R¹⁹ is selected from H, $C_1$-$C_6$ alkyl, —C(=NH)NH₂, —C(O)(CH₂)ᵣNR²²C(=NH)NH₂,
—C(O)CH(NH₂)(CH₂)₃NHC(=NH)NH₂,
—C(O)(CH₂)₂NHC(O)(CH₂)₅NR²²C(=NH)NH₂,
—C(O)CH(NH₂)(CH₂)₄NH₂, and G, where:
R²² is selected from H and $C_1$-$C_6$ alkyl; and
r is an integer from 1 to 5, and
R²⁰ is selected from H and $C_1$-$C_6$ alkyl; and R² is selected from H, G, acyl, trityl, 4-methoxytrityl, $C_1$-$C_6$ alkyl, —C(=NH)NH₂, —C(O)—R²³, —C(O)(CH₂)NR²⁴C(=NH)NH₂,
—C(O)(CH₂)₂NHC(O)(CH₂)₅NR²⁴C(=NH)NH₂,
—C(O)CH(NH₂)(CH₂)₃NHC(=NH)NH₂, and a
moiety of the formula:

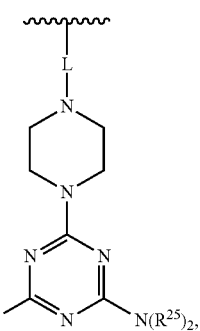

where,
R²³ is of the formula —(O-alkyl)ᵥ-OH where v is an integer from 3 to 10 and each of the v alkyl groups is independently selected from $C_2$-$C_6$ alkyl; and
R²⁴ is selected from H and $C_1$-$C_6$ alkyl;
s is an integer from 1 to 5;
L is selected from —C(O)(CH₂)₆C(O)— and —C(O)(CH₂)₂S₂(CH₂)₂C(O)—; and
each R²⁵ is of the formula —(CH₂)₂₀C(O)N(R²⁶)₂ where each R²⁶ is of the formula —(CH₂)₆NHC(=NH)NH₂,
where G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

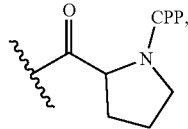

where the CPP is attached to the linker moiety by an amide bond at the CPP carboxy terminus, with the proviso that up to one instance of G is present, and where the targeting sequence is complementary to 12 or more contiguous nucleotides in a target region spanning an intron/exon junction of human myostatin pre-mRNA, said junction selected from intron 1/exon 2 and exon 2/intron 2. In some embodiments, the contiguous nucleotides include the splice intron/exon junction.

In various embodiments, the intron 1/exon 2 junction is selected from SEQ ID NO: 6 and the exon 2/intron 2 junction is selected from SEQ ID NO: 7 or SEQ ID NO: 8.

In various embodiments, Nu is independently adenine, guanine, thymine, uracil, cytosine, inosine, hypoxanthine, 2,6-diaminopurine, 5-methyl cytosine, C5-propynyl-modified pyrimidines, or 10-(9-(aminoethoxy)phenoxazinyl).

In various embodiments, the targeting sequence comprises a sequence selected from SEQ ID NOS: 1-5, 10-31, or 50-65, is selected from SEQ ID NOS: 1-5, 10-31, or 50-65, is a fragment of at least 12 contiguous nucleotides of a targeting sequence selected from SEQ ID NOS: 1-5, 10-31, or 50-65, or is a variant having at least 90% sequence identity to a targeting sequence selected from SEQ ID NOS: 1-5, 10-31, or 50-65, and wherein X is independently selected from uracil (U) or thymine (T). In some embodiments, X is uniformly U or uniformly T.

In various embodiments, R$^1$ of formula (I) is —N(CH$_3$)$_2$. In some embodiments, 50-90% of the R$^1$ groups are —N(CH$_3$)$_2$. In some embodiments, at least one R$^1$ is selected from:

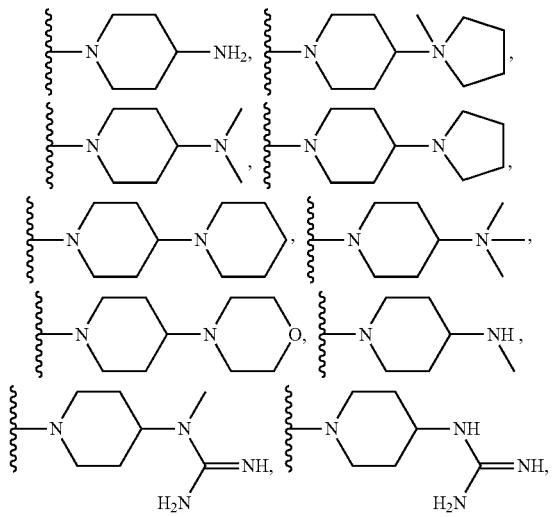

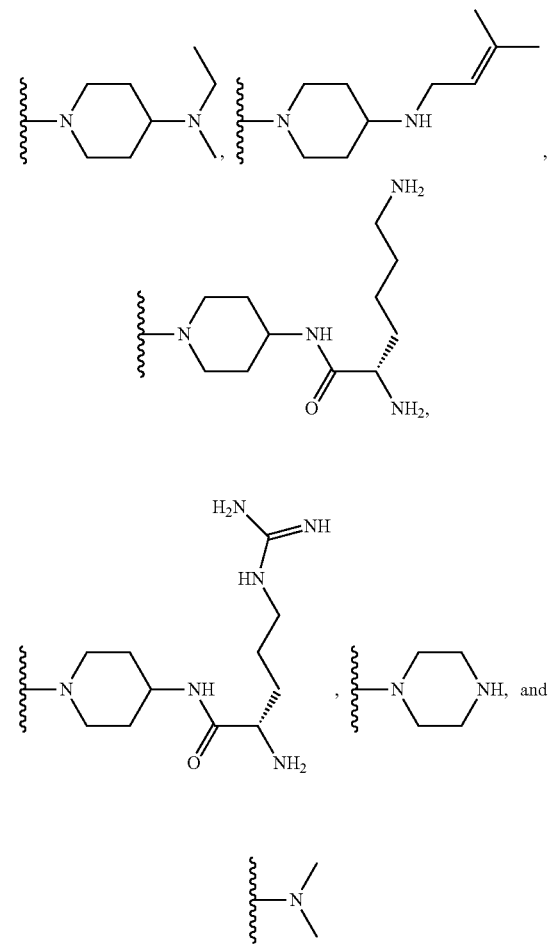

In various embodiments, T is of the formula:

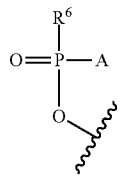

where A is —N(CH$_3$)$_2$, and R$^6$ is of the formula:

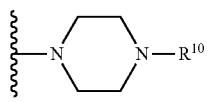

where R$^{10}$ is —C(O)R$^{11}$OH, wherein

R$^{11}$ is of the formula —(O-alkyl)$_y$—wherein y is an integer from 3 to 10 and each of the y alkyl groups is independently selected from C$_2$-C$_6$ alkyl.

In various embodiments, the antisense oligomer is a compound of formula (IV):

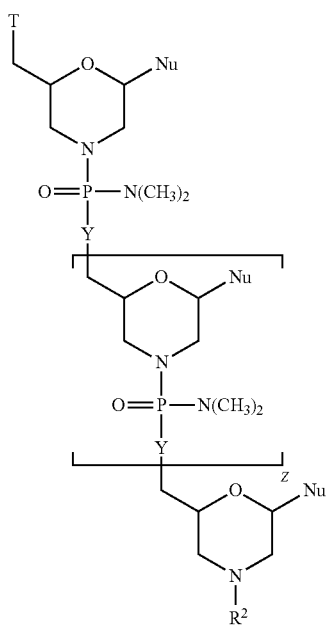

(IV)

or a pharmaceutically acceptable salt thereof, where:
each Nu is a nucleobase which taken together form a targeting sequence;
Z is an integer from 10 to 38;
each Y is independently selected from O and —NR$^4$, wherein each R$^4$ is independently selected from H, C$_1$-C$_6$ alkyl, aralkyl, —C(=NH)NH$_2$, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;
T is selected from OH and a moiety of the formula:

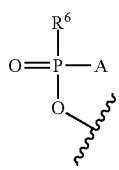

where:
A is selected from —OH and —N(R$^7$)$_2$, where:
each R$^7$ is independently selected from H and C$_1$-C$_6$ alkyl, and
R$^6$ is selected from OH, —N(R$^9$)CH$_2$C(O)NH$_2$, and a moiety of the formula:

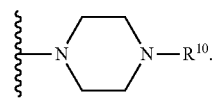

where:
R$^9$ is selected from H and C$_1$-C$_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^{12}$C(=NH)NH$_2$, and
—C(O)(CH$_2$)$_2$NHC(O)(CH$_2$)$_5$NR$^{12}$C(=NH)NH$_2$,
where:
m is an integer from 1 to 5,
R$^{11}$ is of the formula —(O-alkyl)$_y$—, wherein y is an integer from 3 to 10 and each of the y alkyl groups is independently selected from C$_2$-C$_6$ alkyl; and
R$^{12}$ is selected from H and C$_1$-C$_6$ alkyl; and
R$^2$ is selected from H, G, acyl, trityl, 4-methoxytrityl, C$_1$-C$_6$ alkyl, —C(=NH)NH$_2$, and —C(O)—R$^{23}$.

In various embodiments, the targeting sequence of compound (IV) comprises a sequence selected from SEQ ID NOS: 1-5, 10-31, or 50-65, is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T). In some embodiments, X is uniformly U or uniformly T.

In some embodiments, the targeting sequence is selected from SEQ ID NOS: 16-18.

In various embodiments, the antisense oligomer further comprises a peptide moiety which enhances cellular uptake.

In various aspects, antisense oligomers comprising a targeting sequence complementary to 12 or more contiguous nucleotides in a target region spanning a splice junction of myostatin pre-mRNA are provided. In some embodiments, the contiguous nucleotides include the splice intron/exon junction. In further aspects and embodiments, the splice junction comprises at least one of a splice junction between intron 1/exon 2 or a splice junction between intron 2/exon 2. In various embodiments, the target region comprises at least one of SEQ ID NO: 6, SEQ ID NO: 7 and SEQ ID NO: 8 as set forth in Table 1. In some embodiments, the targeting sequence comprises one of SEQ ID NOS: 1-5, 10-31, or 50-65, is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T). In various embodiments, the targeting sequence comprises SEQ ID NOS: 16-18.

In some embodiments of any of the methods or compositions described herein, Z is an integer from 8 to 28, from 15 to 38, 15 to 28, 8 to 25, from 15 to 25, from 10 to 38, from 10 to 25, from 12 to 38, from 12 to 25, from 14 to 38, or from 14 to 25. In some embodiments of any of the methods or compositions described herein, Z is 12, 13, 14, 15, 16, 17, 18, 19, 20, 21, 22, 23, 24, 25, 26, 27, 28, 29, 30, 31, 32, 33, 34, 35, 36, 37, or 38. In some embodiments of any of the methods or compositions described herein, Z is 12, 13, 14, 15, 16, 17, 18, 19, 20, 21, 22, 23, 24, 25, 26, 27, or 28. In some embodiments of any of the methods or compositions described herein, Z is 15, 16, 17, 18, 19, 20, 21, 22, 23, 24, or 25.

Also included are pharmaceutical compositions, comprising a physiologically-acceptable carrier and an antisense oligomer described herein.

Various aspects relate to methods of increasing muscle mass in a subject. In further aspects, methods of treating or preventing the decrease of muscle mass in a subject are provided, where, a subject may be a healthy subject or a subject afflicted with a muscle decreasing disease, disorder, or condition. In further aspects, methods of treating muscular dystrophy or a related disorder are provided. In further aspects, methods of inhibiting the expression of genomic exon 2 of the myostatin gene are provided. In further aspects, methods of inhibiting the splicing of myostatin pre-mRNA sequences comprising a splice junction are provided. In further aspects, methods of inhibiting the splicing of at least one of intron 1 and intron 2 from exon 2 in a myostatin pre-mRNA transcript are provided. In further aspects, methods of inhibiting the expression of exon 2 in a mature mRNA myostatin transcript are provided. In further aspects, methods of inhibiting the expression of myostatin mRNA are provided. In further aspects, methods of modulating the expression of a myostatin protein are provided. In further aspects, methods of inhibiting the expression of a functional myostatin protein are provided.

Various methods relating to increasing muscle mass in a subject or treating or preventing skeletal muscle mass deficiency in a subject includes, administering an antisense oligomer described herein to a subject in need thereof, where the antisense oligomer binds to a target region of a human myostatin pre-mRNA transcript, and where transcription of the target region into a human myostatin mRNA transcript is inhibited. In various embodiments, the target region comprises a splice junction. In further embodiments, the splice junction comprises at least one of the intron 1/exon 2 junction or the exon 2/intron 2 junction. In further embodiments, the antisense oligomer comprises a modified antisense oligomer. Further methods include: (a) measuring blood or tissue levels of myostatin protein in a subject; (b) administering to the subject, an effective amount of an antisense oligomer that binds to a target region in a human myostatin pre-mRNA transcript; (c) where transcription of exon 2 in the myostatin mRNA transcript is inhibited; (d) measuring myostatin protein levels in the subject at a select time; and, (e) repeating administering using the levels measured in (d) to adjust the dose or dosing schedule of the amount of antisense oligomer administered. In various embodiments, the level of myostatin protein is decreased in the subject after administering the antisense oligomer. In further embodiments, the antisense oligomer comprises a modified antisense oligomer.

Methods of treating muscular dystrophy and related disorders in a subject in need thereof include, administering to the subject in need thereof an effective amount of an antisense oligomer described herein. In embodiments, muscular dystrophy and related disorders comprises at least one of Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, Emery-Dreifuss muscular dystrophy, muscle wasting conditions or disorders, such as AIDS, cancer or chemotherapy related muscle wasting, and fibrosis or fibrosis-related disorders (for example, skeletal muscle fibrosis). In various embodiments, the antisense oligomer comprises a modified antisense oligomer as described herein.

Methods of inhibiting the expression of genomic exon 2 of the myostatin gene include administering an antisense oligomer to a subject in need thereof, where the antisense oligomer binds to a target region of a myostatin pre-mRNA transcript. Splicing of exon 2 from proximate introns (e.g., introns 1 and 2) is inhibited. Expression of pre-mRNA exon 2 into mature mRNA is inhibited. At least some mature mRNA excludes exon 2. Expression of myostatin mRNA myostatin is inhibited as the resulting transcript is missing key functional elements from exon 2. Accordingly, expression of genomic exon 2 is inhibited. In various embodiments, the target is a region spanning a splice junction of a human myostatin pre-mRNA transcript. In further embodiments, the splice junction comprises sequences from at least one of the intron 1/exon 2 junction or the exon 2/intron 2 junction. In further embodiments, the antisense oligomer comprises a modified antisense oligomer as described herein.

Methods of modulating the expression of a myostatin protein include, administering to a subject in need thereof an antisense oligomer to such subject, where the antisense oligomer binds to a target region of a myostatin pre-mRNA transcript. Exon 2 is excluded from at least some of the resulting mature mRNA transcript. Translation of the resulting mRNA to a myostatin protein is inhibited. In various embodiments, at least some protein originating from the pre-mRNA myostatin transcript is a non-functional protein as the resulting protein is missing key functional elements of the myostatin gene as contained in exon 2. In further embodiments, expression of a functional myostatin protein is inhibited. In further embodiments, the target region comprises a splice junction. In further embodiments, the splice junction comprises sequences from at least one of the intron 1/exon 2 junction or the exon 2/intron 2 junction. In further aspects and embodiments, translation of myostatin mRNA into a functional myostatin protein is inhibited. In further embodiments, the antisense oligomer comprises a modified antisense oligomer as described herein.

In various embodiments, expression of exon 2 within mature myostatin mRNA is inhibited by at least 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%.

Methods for decreasing the accumulation of a functional myostatin protein, for example as arising in a muscle cell or tissue are provided, comprising administering an antisense oligomer described herein to a subject in need thereof, where the antisense oligomer binds to a target region of a myostatin pre-mRNA transcript, and where transcription of the target region into a mature myostatin mRNA transcript is inhibited. In various embodiments, the target region is a region spanning a splice junction of a human myostatin pre-mRNA transcript, and in further embodiments, the splice junction comprises sequences spanning at least one of the intron 1/exon 2 junction or the exon 2/intron 2 junction. In further embodiments, the antisense oligomer comprises a modified antisense oligomer.

Further methods include administering an effective amount of an antisense oligomer described herein to a subject in need of such treatment to result in a peak blood concentration of at least about 200-400 nM of antisense oligomer in the subject. In further embodiments, the antisense oligomer comprises a modified antisense oligomer as described herein.

Methods of treating muscular dystrophy and related disorders in a subject in need thereof, include administering to the subject an effective amount of an antisense oligomer of the disclosure, where the antisense oligomer binds to a target region of a human myostatin pre-mRNA transcript, and where transcription of the target region into a human myostatin mRNA transcript is inhibited. Further aspects include antisense oligomers for use in the preparation of a medicament for the treatment of muscular dystrophy and related disorders. In various embodiments, the antisense oligomer comprises a modified antisense oligomer.

In certain embodiments, the method comprises reducing the myostatin levels in a subject by at least about 10% relative to a control. In some embodiments, the myostatin levels in a subject are reduced by at least about 1, 2, 3, 4, 5, 6, 7, 8, 9, or 10%.

These and other aspects of the present disclosure will become apparent upon reference to the following detailed description and attached drawings. All references disclosed herein are hereby incorporated by reference in their entirety as if each was incorporated individually.

DETAILED DESCRIPTION OF THE INVENTION

I. Definitions

Figure 1A:
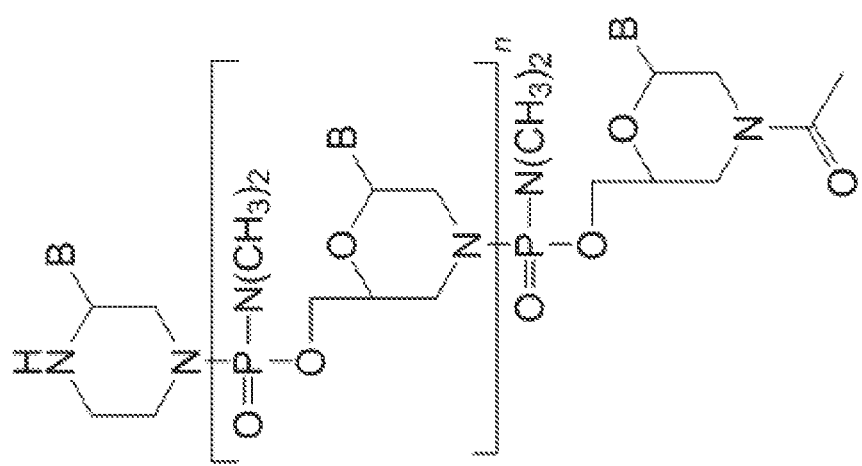
FIG. 1A illustrates a modified oligomer at the 5' end to add a linker.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

The term "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The terms "sequence" and "coding sequence" mean any nucleic acid sequence that contributes to the code for the polypeptide product of a gene. By contrast, the term "noncoding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

The term "consisting of" means including, and limited to, whatever follows the phrase "consisting of." Thus, the phrase "consisting of" indicates that the listed elements are required or mandatory, and that no other elements may be present. The term "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "administering," or "administer" include delivery of the antisense oligomers of the disclosure to a subject either by local or systemic administration. Administration may be topical (including ophthalmic and to mucous membranes including vaginal and rectal delivery), pulmonary, e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

The terms "contacting a cell," "introducing" or "delivering" include delivery of the oligomers of the disclosure into a cell by methods routine in the art, e.g., transfection (e.g., liposome, calcium-phosphate, polyethyleneimine), electroporation (e.g., nucleofection), microinjection).

The term "alkyl" refers to a linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_1$-$C_6$ alkyl, is intended to include $C_1$, $C_2$, $C_3$, $C_4$, $C_5$, and $C_6$ alkyl groups. Lower alkyl refers to alkyl groups containing 1 to 6 carbon atoms. Examples of alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The term "alkoxy" refers to a subset of alkyl in which an alkyl group as defined above with the indicated number of carbons attached through an oxygen bridge. For example, "alkoxy" refers to groups—O-alkyl, where the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

The term "aryl" used alone or as part of a larger moiety as in "aralkyl,", "aralkoxy," or "aryloxy-alkyl," refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring." "Aryl" also includes fused polycyclic aromatic ring systems in which an aromatic ring is fused to one or more rings. Non-limiting examples of useful aryl ring groups include phenyl, hydroxyphenyl, halophenyl, alkoxy-phenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl," as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "acyl" refers to a C(O)R group (in which R signifies H, alkyl or aryl as defined above). Examples of acyl groups include formyl, acetyl, benzoyl, phenylacetyl and similar groups.

The term "homolog" refers to compounds differing regularly by the successive addition of the same chemical group. For example, a homolog of a compound may differ by the addition of one or more —$CH_2$— groups, amino acid residues, nucleotides, or nucleotide analogs.

The terms "cell penetrating peptide" (CPP) or "a peptide moiety which enhances cellular uptake" are used interchangeably and refer to cationic cell penetrating peptides, also called "transport peptides," "carrier peptides," or "peptide transduction domains." For example, a peptide-conjugated phosphoramidate or phosphorodiamidate morpholino (PPMO) may include a cell penetrating peptide or peptide moiety which enhances cellular uptake as described herein. In various embodiments, a peptide may be covalently bonded to the antisense oligomer. In further embodiments, a peptide may be covalently bonded to the 3' end or the 5' end of the antisense oligomer. In further embodiments, a peptide may be linked to a piperazinyl moiety or to a nitrogen atom of the 3' terminal morpholine ring. In some embodiments, a cell penetrating peptide or peptide moiety which enhances cellular uptake may include an arginine-rich peptide as described herein.

The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. In some embodiments, the CPPs are of the formula —$[(C(O)CHR'NH)_m]R''$ where R' is a side chain of a naturally occurring amino acid or a one- or two-carbon homolog thereof, R'' is selected from Hydrogen or acyl, and m is an integer up to 50. Additional CPPs are well-known in the art and are disclosed, for example, in U.S. Published Application No. 20100016215, which is hereby incorporated by reference in its entirety. In other embodiments, m is an integer selected from 1 to 50 where, when m is 1, the moiety is a single amino acid or derivative thereof.

The term "amino acid" refers to a compound comprising a carbon atom to which are attached a primary amino group, a carboxylic acid group, a side chain, and a hydrogen atom. For example, the term "amino acid" includes, but is not limited to, Glycine, Alanine, Valine, Leucine, Isoleucine, Asparagine, Glutamine, Lysine, Aspartic Acid, Histidine, Methionine, Proline, Phenylalanine, Threonine, Tryptophan, Cysteine, Glutamic Acid, Serine, Tyrosine, Pyrolysine, Selenocystenine and Arginine. Additionally, as used herein, "amino acid" also includes derivatives of amino acids such as esters, and amides, and salts, as well as other derivatives, including derivatives having pharmaco properties upon metabolism to an active form. Accordingly, the term "amino acid" is understood to include naturally occurring and non-naturally occurring amino acids.

The term "an electron pair" refers to a valence pair of electrons that are not bonded or shared with other atoms.

The term "homology" refers to the percentage number of amino acids that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The term "isolated" refers to a material that is substantially or essentially free from components that normally accompany it in its native state. For example, an "isolated oligonucleotide," or "isolated oligomer" as used herein, may refer to an oligonucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with an oligonucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more antisense oligomer compounds or compositions to produce or cause a greater physiological response (e.g., downstream effects) in a cell or a subject relative to the response caused by either no antisense oligomer compound or a control compound. Relevant physiological or cellular responses (in vivo or in vitro) will be apparent to persons skilled in the art, and may include decreases in the inclusion or exclusion of exon 2 in a myostatin-coding mRNA, or decrease in the expression of functional myostatin protein in a cell, or tissue, such as in a subject in need thereof. A "decreased" or "reduced" amount is typically a "statistically significant" amount, and may include a decrease that is 1, 2, 3, 4, 5, 6, 7, 8, 9, 10, 15, 20, 30, 40, 50 or more times less (e.g., 100, 500, 1000 times), including all integers and decimal points in between and above 1 (e.g., 1.1, 1.2, 1.3, 1.4, 1.5, 1.6, 1.7, 1.8, 1.9), the amount produced by a subject in need thereof in the absence of administration of an antisense oligomer compound (e.g. the "native" or "natural" rate of expression of a specific subject or cohort) or a control compound. The terms "reduce" or "inhibit" may relate generally to the ability of one or more antisense oligomer compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of muscular dystrophy and related disorders, such as Duchennes muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, Emery-Dreifuss muscular dystrophy, muscle wasting conditions or disorders, such as AIDS, cancer or chemotherapy related muscle wasting, and fibrosis or fibrosis-related disorders (for example, skeletal muscle fibrosis), for example, where a reduction in symptoms or pathology may accompany or relate to a decrease in the expression of a functional myostatin protein and/or accumulation of a functional myostatin protein in one or more tissues. A "decrease" in a response may be "statistically significant" as compared to the response produced by a subject in need thereof in the absence of administration of an antisense oligomer compound (e.g. the "native" or "natural" rate of expression of a specific subject or cohort)) or a control compound, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The term "functional" in reference to a myostatin protein includes those proteins derived from a mRNA transcript containing sequences corresponding to exon 1, exon 2 and exon 3 of a myostatin gene. A non-functional protein includes a protein derived from a mRNA transcript missing all or any portion of the corresponding full gene sequence of exon 1, exon 2 and exon 3, or that contains all or a portion of the sequences corresponding to intron 1, intron 2, or other intron sequences, or where the non-functional state relates to missing functional elements as derived from a respective exon, or as otherwise derived from the inclusion of a respective intron, including partial or full sequences thereof.

The term "nucleotide" refers to a naturally occurring nucleotide comprising a nucleobase, a sugar and at least one phosphate group (e.g., a phosphodiester linking group).

The term "nucleotide analog" refers to a derivative of, or modification to, a naturally occurring nucleotide, for example, a nucleotide comprising at least one modification. Such modifications may include at least one of (i) a modified internucleoside linkage, (ii) a modified sugar moiety, or (iii) a combination of the foregoing. The skilled practitioner will appreciate that where a modification is specified with respect to any one component of a nucleotide subunit (e.g., a modified sugar), the unspecified portion(s) of the nucleotide subunit may remain unmodified (e.g., an unmodified internucleoside linkage, an unmodified nucleobase).

The terms "oligonucleotide," "oligomer," "oligo," "antisense oligonucleotide," "antisense oligomer," and "antisense oligo," and other appropriate combinations and derivations thereof, refer to linear sequences of nucleotides, or nucleotide analogs, where one or more nucleobases may hybridize to a portion of a target RNA against which the oligomer is directed, referred to as a target sequence, by Watson-Crick base pairing, to form an oligomer:RNA heteroduplex within the target sequence. Specifically, the terms "antisense," "oligonucleotide," "oligomer," "oligo" and "compound" may be used in various combinations and interchangeably to refer to such an oligomer. Cyclic subunits comprising portions of the nucleotides may be based on ribose or another pentose sugar, sugar analog or, in certain embodiments may be a modified sugar, for example, a morpholino group (see description of morpholino-based oligomers below).

The term "modified," "non-naturally-occurring," or "analogs," and other appropriate combinations and derivatives thereof, when referring to oligomers, refer to oligomers having one or more nucleotide subunits having at least one modification selected from (i) a modified internucleoside linkage, e.g., an internucleoside linkage other than the standard phosphodiester linkage found in naturally-occurring oligonucleotides, (ii) modified sugar moieties, e.g., moieties other rather than ribose or deoxyribose moieties found in naturally occurring oligonucleotides, or (iii) a combination of the foregoing. In various embodiments, a modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2'O-methyl subunit, a 2'O-methoxyethyl subunit, a 2'-fluoro subunit, a 2'-O-[2-(N-methylcarbamoyl)ethyl] subunit, and a morpholino subunit.

A modification to the internucleoside linkage may be between at least two sugar and/or modified sugar moieties of an oligomer. Nucleotide analogs support bases capable of hydrogen bonding by Watson-Crick base pairing to naturally occurring oligonucleotide bases, where the analog presents the bases in a manner to permit such hydrogen bonding in a sequence-specific fashion between the oligomer analog molecule and bases in the naturally occurring oligonucleotide (e.g., single-stranded RNA or single-stranded DNA). Exemplary analogs are those having a substantially uncharged, phosphorus containing internucleoside linkages.

A "nuclease-resistant" oligomer refers to one whose internucleoside linkage is substantially resistant to nuclease cleavage, in non-hybridized or hybridized form; by common extracellular and intracellular nucleases in the body (for example, by exonucleases such as 3'-exonucleases, endonucleases, RNase H); that is, the oligomer shows little or no nuclease cleavage under normal nuclease conditions in the body to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA. For example, a nuclease-resistant oligomer may be an antisense oligomer as described herein.

The terms "nucleobase" (Nu), "base pairing moiety" or "base" are used interchangeably to refer to a purine or pyrimidine base found in naturally occurring, or "native." DNA or RNA (e.g., uracil, thymine, adenine, cytosine, and guanine), as well as analogs of these naturally occurring purines and pyrimidines, that may confer improved properties, such as binding affinity to the oligomer. Exemplary analogs include hypoxanthine (the base component of the nucleoside inosine); 2, 6-diaminopurine; 5-methyl cytosine; C5-propynyl-modified pyrimidines; 10-(9-(aminoethoxy) phenoxazinyl) (G-clamp) and the like.

Further examples of base pairing moieties include, but are not limited to, uracil, thymine, adenine, cytosine, guanine and hypoxanthine (inosine) having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glenresearch.com); Krueger A T et al., Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

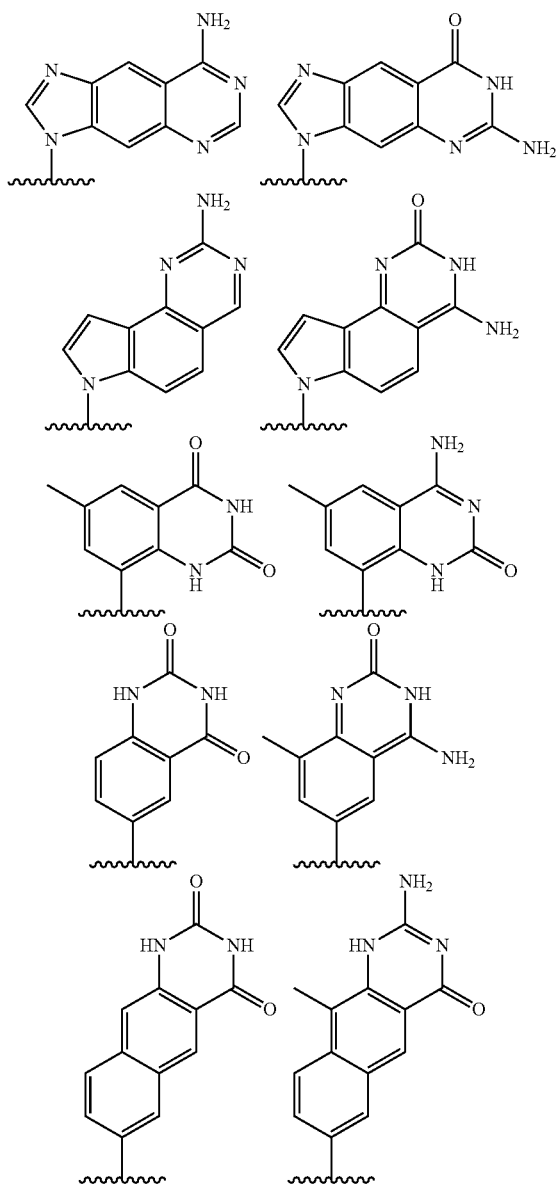

A nucleobase covalently linked to a ribose, sugar analog, modified sugar or morpholino comprises a nucleoside. "Nucleotides" comprise a nucleoside together with at least one linking phosphate group. The phosphate groups comprise covalent linkages to adjacent nucleosides form an oligomer. Thus, the phosphate group of the nucleotide is commonly referred to as forming an "internucleoside linkage." Accordingly, a nucleotide comprises a nucleoside as further described herein and an internucleoside linkage. In some embodiments, an antisense oligomer of the disclosure comprises subunits wherein a "subunit" includes naturally occurring nucleotides, nucleotide analogs as described herein, and combinations thereof. In certain embodiments, an antisense oligomer of the disclosure comprises subunits wherein at least one subunit is a nucleotide analog.

The terms "sequence identity" and "sequence homology" (e.g. a "sequence 50% identical to) refer to the extent that a sequence is identical on a nucleotide-by-nucleotide basis over a window of comparison. A "percentage identity" may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

As used herein, an oligomer "specifically hybridizes" to a target oligonucleotide if the oligomer hybridizes to the target under physiological conditions, with a melting point (Tm) substantially greater than 40° C., 45° C., 50° C., and in various embodiments, 60° C. to 80° C., or higher. Such hybridization preferably corresponds to stringent hybridization conditions. At a given ionic strength and pH, the Tm is the temperature at which 50% of a target sequence hybridizes to a complementary sequence. Such hybridization may occur with "near" or "substantial" complementarity of the antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100%.

As used herein, the term "subunit" refers to a naturally occurring nucleotide or a naturally occurring nucleotide comprising at least one modification. A modification may comprise at least one of (i) a modified internucleoside linkage, (ii) a modified sugar moiety, or (iii) a combination of the foregoing. In further embodiments, a modification may include a modified nucleobase.

As used herein, the term "sufficient length" refers to an antisense oligomer that is complementary to at least 12, more typically 12-40, contiguous nucleobases in a region spanning a human myostatin pre-mRNA splice junction region comprising intron 1/exon 2 or exon 2/intron 2. In various embodiments, the antisense oligomer comprises at least a number of nucleotides to be capable of specifically hybridizing to a target region of a myostatin pre-mRNA sequence. Preferably an oligomer of sufficient length is from 12 to 30 nucleotides in length. More preferably, an oligomer of sufficient length is from 12 to 27 nucleotides in length.

As used herein, the term a "subject" or a "subject in need thereof" includes a mammalian subject such as a human subject. Exemplary mammalian subjects have or are at risk for having muscular dystrophy and related disorders. As used herein, the term "muscular dystrophy" and "related disorders" refers to a muscular dystrophy or related disorder, a human autosomal recessive disease that is often characterized by over expression of myostatin protein in affected individuals. In some embodiments, muscular dystrophy and related disorders include, but are not limited to, Duchennes muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, Emery-Dreifuss muscular dystrophy, muscle wasting conditions or disorders, such as AIDS, cancer or chemotherapy related muscle wasting, and fibrosis or fibrosis-related disorders (for example, skeletal muscle fibrosis).

As used herein, the term "target" refers to a region within a pre-mRNA transcript as relating to the antisense oligomers contemplated herein. In various aspects, the target is a region spanning an intron/exon splice junction of human myostatin pre-mRNA. In various embodiments, the target region is a splice junction region comprising intron 1/exon 2 or exon 2/intron 2 of the pre-mRNA of myostatin. In various embodiments, the target region comprises all or at least a portion of SEQ ID NO: 6, SEQ ID NO: 7 or SEQ ID NO: 8, wherein the portion spans at least the splice junction of intron 1/exon 2 or exon 2/intron 2.

In various embodiments, the term "targeting sequence" refers to the sequence in the antisense oligomer or oligomer analog that is complementary to the target sequence in the pre-mRNA transcript. The entire sequence, or only a portion, of the antisense oligomer may be complementary to the target sequence. For example, in an oligomer having 20-30 bases, about 12, 13, 14, 15, 16, 17, 18, 19, 20, 21, 22, 23, 24, 25, 26, 27, 28, 29, or 30 may contain sequences (e.g. "targeting sequences") that are complementary to the target region within the pre-mRNA transcript. Typically, the targeting sequence is formed of contiguous bases in the oligomer, but may alternatively be formed of non-contiguous sequences that when placed together, e.g., from opposite ends of the oligomer, constitute a sequence that spans the target sequence.

A "targeting sequence" may have "near" or "substantial" complementarity to the target sequence and still function for its indended purpose, for example, to decrease expression of myostatin exon 2 coding pre-mRNA or decrease expression of a functional myostatin protein. Preferably, antisense oligomer compounds employed in the present disclosure have at most one mismatch with the target sequence out of 12 nucleotides, and preferably at most one mismatch out of 20. Alternatively, the antisense oligomers employed have at least 90% sequence homology, and preferably at least 95% sequence homology, with the exemplary targeting sequences as designated herein. A targeting sequence may be a sequence spanning an intron/exon splice junction of the human myostatin gene. In some embodiments, an intron/exon splice junction comprises intron 1/exon 2 or exon 2/intron 2.

As used herein, the term "TEG" or "triethylene glycol tail" refers to triethylene glycol moieties covalently bonded to the oligonucleotide, e.g., at its 3'- or 5'-end. For example, in some embodiments, "TEG" includes wherein T of the compound of formula (I) is of the formula:

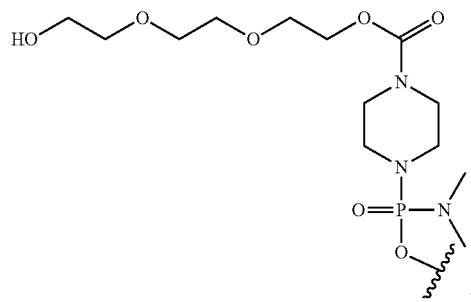

As used herein, the term a "therapeutically effective amount" or "effective amount" of a composition refers to an amount effective in the prevention or treatment of a disorder for the treatment of which the composition is effective. A "disorder" refers to any muscular dystrophy or related disorder that would benefit from treatment with the composition.

As used herein, the terms "quantifying," "quantification" or other related words refer to determining the quantity, mass, or concentration in a unit volume, of a nucleic acid, oligonucleotide, oligomer, peptide, polypeptide, or protein.

In various embodiments, as used herein, the term "treatment" includes treatment of a subject (e.g. a mammal, such as a human) or a cell to alter the current course of the subject or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

II. Modulation of the Intron/Exon Splice Junction of Myostatin Pre-mRNA

Various aspects relate to methods for modulating the splicing of intron and exons of myostatin pre-mRNA. Further aspects relate to inhibiting splicing at the splice junction site of intron 1/exon 2 and exon 2/intron 2. In further aspects, expression of myostatin exon 2 coding mRNA is inhibited, such as relative to exon-2 wildtype mRNA, in a given sample (e.g., serum, plasma, tissue, cellular etc.). Various methods include administering an antisense oligomer described herein that is complementary to a target region within the myostatin pre-mRNA, where expression of myostatin exon 2 mRNA is inhibited relative to the expression of exon-2 wildtype (i.e. control) mRNA.

For illustration purposes, and without being bound by theory, antisense oligomers as described herein are believed to facilitate blocking, inhibiting or modulating the processing of a pre-mRNA, such as by inhibiting the action of a spliceosome and production of a mature mRNA transcript, and may also induce degradation of targeted mRNAs. The antisense oligomer may be said to be "directed to" or "targeted against" a target sequence or target region with which it hybridizes. In certain embodiments, the target sequence includes a region including a 3' or 5' splice junction site of a pre-mRNA, a branch point, or other sequence involved in the regulation of splicing. The target sequence may include sequences within an intron/exon or an exon/intron splice junction site, or spanning an intron/exon or exon/intron splice junction.

An antisense oligomer having a sufficient sequence complementarity to a target pre-mRNA sequence to modulate splicing of the target RNA includes where the antisense oligomer has a sequence sufficient to trigger the masking or hindrance of a binding site for a spliceosome complex that would otherwise affect such splicing and/or otherwise includes alterations in the three-dimensional structure of the targeted pre-mRNA.

In various embodiments, the antisense oligomer has sufficient length and complementarity to a sequence spanning an intron 1/exon 2 or exon 2/intron 2 of the human myostatin pre-mRNA. In various embodiments, targeting sequences within an antisense oligomer hybridize to a region of one or more of the target sequences, for example SEQ ID NO: 6, SEQ ID NO: 7 or SEQ ID NO: 8, shown in Table 1 below. In some embodiments, antisense oligomers may be shorter, e.g., about 12 bases, or longer, e.g., about 40 bases, and include a small number of mismatches, as long as the sequence is sufficiently complementary to effect splice modulation upon hybridization to the target sequence, and optionally forms with the RNA a heteroduplex having a Tm of 45° C. or greater.

TABLE 1

Target sequences for Myostatin-targeted oligomers (from NG_009800)

| Name | Sequence (5'-3') | SEQ ID NO |
|---|---|---|
| SA2 | CTTTTCTTTTCTTATTCATTTATAG/<br>CTGATTTTCTAATGCAAGTGGATGG | 6 |
| SD2a | CCCAGGACCAGGAGAAGATGGGCTG/<br>GTAAGTGATAACTGAAAATAACATT | 7 |
| SD2b | ACCTTCCCAGGACCAGGAGAAGATGGGCTG/<br>GTAAGTGATAACTGAAAATAACATTATAAT | 8 |

"/" indicates the splice site

In various embodiments, the degree of complementarity between the antisense targeting sequence and the target sequence is sufficient to form a stable duplex. The region of complementarity of the antisense oligomers with the target sequence may be as short as 12-15 bases but can be 12-20 bases or more, e.g., 12-40 bases, 12-30 bases, 12-25 bases, 15-25 bases, or 15-20 bases, including all integers in between these ranges. An antisense oligomer of about 12-15 bases is generally long enough to have a unique complementary sequence. In certain embodiments, a minimum length of complementary bases may be required to achieve the requisite binding Tm, as discussed herein.

In various aspects, the oligomers are configured for additional functionality, including but not limited to bio-availability, stability, cellular update, and resistance to nuclease degradation. Generally, oligomers comprising 40 bases may be suitable, where at least a minimum number of bases, e.g., 12 bases, are complementary to the target sequence. In various aspects, the oligomers are configured to enhance facilitated or active cellular uptake. In various embodiments, these oligomers are optimized to a length of less than or about 30 bases. In various aspects, the antisense oligomers comprise one or more phosphoramidate morpholino monomer or phosphorodiamidate morpholino monomer subunits. In various embodiments, the antisense oligomers, comprise about 18-25 phosphoramidate morpholino monomer or phosphorodiamidate morpholino monomer subunits. In accordance with a further aspect of the disclosure, the antisense oligomer length and number of modified monomer subunits, including any of a phosphoramidate morpholino monomer or phosphorodiamidate morpholino monomer subunit are varied to obtain an optimum balance of formulation and post-administration stability, and cellular uptake. In certain embodiments, an optimized antisense oligomer comprises 18-25 bases in length with all or substantially all sub-units comprising a phosphoramidate morpholino monomer or phosphorodiamidate morpholino monomer subunit.

In various aspects, the antisense oligomers comprise, consist of, or consist essentially of 12 to 40 subunits, optionally comprising at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an intron/exon splice junction of human myostatin pre mRNA. In various embodiments, the contiguous nucleotides include the splice intron/exon junction. In further embodiments, the splice junctions may be selected from the splice junction at intron 1/exon 2 (e.g., SEQ ID NO: 6) or exon 2/intron 2 (e.g., SEQ ID NO: 7, or SEQ ID NO: 8).

Additional aspects include antisense oligomers of 12 to 40 subunits that specifically hybridize to a target region spanning an intron/exon splice junction of human myostatin pre-mRNA. The splice junctions are optionally selected from splice junctions at the intersection of intron 1/exon 2 and exon 2/intron 2. In embodiments, the splice junction of intron 1/exon 2 is selected from the splice junction within SEQ ID NO: 6; the splice junction of exon 2/intron 2 is selected from the splice junction within SEQ ID NO: 7, or SEQ ID NO: 8.

Additional aspects include antisense oligomers having a nucleotide analog subunit comprising a modified sugar moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl) ethyl] subunit, and a morpholino subunit.

Additional aspects include antisense oligomers having a nucleotide analog subunit comprising a modified internucleoside linkage. In various embodiments, the modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

Additional aspects include antisense oligomers having a nucleotide analog subunit comprising at least one combination of a modified sugar moiety and a modified internucleoside linkage, wherein various embodiments, one or more subunits are selected from:

a morpholino subunit optionally substituted with a phosphoramidate internucleoside linkage, a phosphorodiamidate internucleoside linkage, or a phosphorothioate internucleoside linkage, a 2' O-methyl subunit optionally substituted with a phosphoramidate internucleoside linkage, a phosphorodiamidate internucleoside linkage, or a phosphorothioate internucleoside linkage, a 2'O-methoxyethyl subunit optionally substituted with a phosphoramidate internucleoside linkage, a phosphorodiamidate internucleoside linkage, or a phosphorothioate internucleoside linkage, a 2'-fluoro subunit optionally substituted with a phosphoramidate internucleoside linkage, a phosphorodiamidate internucleoside linkage, or a phosphorothioate internucleoside linkages, a 2'O,4'C-ethylene-bridged nucleic acid subunit optionally substituted with a phosphoramidate internucleoside linkage, a phosphorodiamidate internucleoside linkage, or a phosphorothioate internucleoside linkage, a 2'-O-[2-(N-methylcarbamoyl)ethyl] subunit optionally substituted with a phosphoramidate internucleoside linkage, a phosphorodiamidate internucleoside linkage, or a phosphorothioate internucleoside linkage, a tricyclo-DNA subunit optionally substituted with a phosphoramidate internucleoside linkage, a phosphorodiamidate internucleoside linkage, or a phosphorothioate internucleoside linkage, a locked nucleic acid subunit optionally substituted with a phosphoramidate internucleoside linkage, a phosphorodiamidate internucleoside linkage, or a phosphorothioate internucleoside linkage, a morpholino subunit further comprising a phosphorodiamidate internucleoside linkage where a phosphorous atom of the phosphorodiamidate is covalently bonded to the nitrogen atom of the morpholine ring, and is covalently bonded to a (1,4-piperazin)-1-yl moiety or to a substituted (1,4-piperazin)-1-yl moiety, a morpholino subunit further comprising a phosphorodiamidate internucleoside linkage where a phosphorus atom of the phosphorodiamidate is covalently bonded to a 4-aminopiperdin-1-yl moiety or a substituted 4-aminopiperdin-1-yl moiety, a ribose sugar subunit substituted with a phosphorothioate internucleoside or a phosphoramidate internucleoside linkage, a deoxyribose sugar subunit substituted with a phosphorothioate internucleoside linkage or a phosphoramidate internucleoside linkage, a peptide nucleic acid subunit optionally substituted, or any combination of the foregoing.

In various aspects and embodiments, antisense oligomers of the disclosure further comprise a peptide covalently bonded to the antisense oligomer. In various embodiments, an arginine-rich cell-penetrating peptide is covalently bonded to the 3' or the 5' end of the antisense oligomer.

In embodiments, an antisense oligomer may consist of about 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, or range from 12 to 40, 12 to 30, 14 to 25, 15 to 30, 17 to 30, 17 to 27, 12 to 27, 12 to 25, and 12 to 20 bases. In some embodiments, the antisense oligomer is about 12 to about 40 or about 12 to about 30 bases in length. In some embodiments, the antisense oligomer is about 14 to about 25 or about 17 to about 27 bases in length. In some embodiments, an antisense oligomer sequence comprises at least about 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases that are complementary to the target sequences of Table 1 (e.g., SEQ ID NOS: 6, SEQ ID NO: 7 or SEQ ID NO: 8, or sequences that span at least a portion of SEQ ID NO: 6, SEQ ID NO: 7 or SEQ ID NO: 8).

The antisense oligomers typically comprise a base sequence which is sufficiently complementary to a sequence or region within or adjacent to intron 1, exon 2, or intron 2 of the pre-mRNA sequence of the human myostatin. Ideally, an antisense oligomer is able to effectively modulate aberrant splicing of the myostatin pre-mRNA, and thereby decrease expression of active myostatin protein. This requirement is optionally met when the oligomer compound has the ability to be actively taken up by mammalian cells, and once taken up, form a stable duplex (or heteroduplex) with the target mRNA, optionally with a Tm greater than about 40° C. or 45° C.

"Complementary" or "complementary" as used herein, refers to an antisense oligomer having about 90% to about 100% of the nucleotide sequence complementary to a target sequence. In embodiments, a complementary nucleotide sequence specifically hybridizes to a target sequence to induce a desired effect, for example, a therapeutic effect as described herein. In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo. Hence, certain oligomers may have substantial complementarity, meaning, about or at least about 90% sequence complementarity, e.g., 90%, 91%, 92%, 93%, 94%, 95%, 96%, 97%, 98%, 99% or 100% sequence complementarity, between the oligomer and the target sequence. Oligomer internucleoside linkages that are less susceptible to cleavage by nucleases are provided herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer need not necessarily comprise 100% complementary to the target sequence, it should have sufficient complementarity to effectively, stably and specifically bind to the target sequence, such that splicing of the target pre-mRNA is sufficiently modulated, for example, to achieve a therapeutic effect, as described herein.

Without being bound by theory, the stability of the duplex formed between an oligomer and a target sequence is believed to be a function of the binding Tm and the susceptibility of the duplex to cellular enzymatic cleavage. The Tm of an oligomer with respect to a complementary-sequence RNA duplex may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In various embodiments, the antisense oligomers have a binding Tm, with respect to a complementary-sequence RNA duplex, of greater than body temperature, such as, for example, greater than about 45° C. or 50° C. Tm's in the range 60-80° C. or greater are also included. According to well-known principles, the Tm of an oligomer, with respect to a complementary-based RNA hybrid duplex, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (45-50° C. or greater) at a length of 25 bases or less are generally preferred over those requiring greater than 25 bases for high Tm values.

Table 2 below shows exemplary targeting sequences (in a 5'-to-3' orientation) that are complementary to the intron/exon splice junction relating to intron 1/exon 2 or exon 2/intron 2 pre-mRNA sequences of the human myostatin gene.

TABLE 2

Antisense oligomer sequences for Myostatin-targeted oligomers

Myostatin Exon 2 Antisense Sequences

| Name | Sequence (5'-3') | SEQ ID NO |
|---|---|---|
| muhuMSTN-SD2(+24 - 01) | CCAGCCCAXCXXCXCCXGGXCCXGG | 1 |
| muhuMSTN-SD2(+18 - 07) | CACXXACCAGCCCAXCXXCXCCXGG | 2 |
| huMSTN-SA2(-01 + 25) | CCAXCCACXXGCAXXAGAAAAXCAGC | 3 |
| huMSTN-SA2(-9 + 15) | GCAXXAGAAAAXCAGCXAXAAAXG | 4 |
| huMSTN-SA2(-01 + 21) | CCACXXGCAXXAGAAAAXCAGC | 5 |
| huMSTN-SA2(-07 + 18) | CXXGCAXXAGAAAAXCAGCXAXAAA | 10 |
| huMSTN-SA2(-05 + 20) | CACXXGCAXXAGAAAAXCAGCXAXA | 11 |
| huMSTN-SA2(-04 + 21) | CCACXXGCAXXAGAAAAXCAGCXAX | 12 |
| huMSTN-SA2(-03 + 22) | XCCACXXGCAXXAGAAAAXCAGCXA | 13 |
| huMSTN-SA2(-02 + 23) | AXCCACXXGCAXXAGAAAAXCAGCX | 14 |
| huMSTN-SA2(-01 + 24) | CAXCCACXXGCAXXAGAAAAXCAGC | 15 |
| muhuMSTN-SD2(+04 - 21) | XXAXXXXCAGXXAXCACXXACCAGC | 16 |
| muhuMSTN-SD2(+07 - 18) | XXXXCAGXXAXCACXXACCAGCCCA | 17 |
| muhuMSTN-SD2(+10 - 15) | XCAGXXAXCACXXACCAGCCCAXCX | 18 |
| muhuMSTN-SD2(+13 - 12) | GXXAXCACXXACCAGCCCAXCXXCX | 19 |
| muhuMSTN-SD2(+16 - 09) | AXCACXXACCAGCCCAXCXXCXCCX | 20 |
| muhuMSTN-SD2(+19 - 06) | ACXXACCAGCCCAXCXXCXCCXGGX | 21 |
| muhuMSTN-SD2(+22 - 03) | XACCAGCCCAXCXXCXCCXGGXCCX | 22 |
| muhuMSTN-SD2(+01 - 24) | AXGXXAXXXXCAGXXAXCACXXACC | 23 |
| muhuMSTN-SD2(+02 - 23) | XGXXAXXXXCAGXXAXCACXXACCA | 24 |

TABLE 2-continued

Antisense oligomer sequences for Myostatin-targeted oligomers

Myostatin Exon 2 Antisense Sequences

| Name | Sequence (5'-3') | SEQ ID NO |
|---|---|---|
| muhuMSTN-SD2(+03 - 22) | GXXAXXXXCAGXXAXCACXXACCAG | 25 |
| muhuMSTN-SD2(+05 - 20) | XAXXXXCAGXXAXCACXXACCAGCC | 26 |
| muhuMSTN-SD2(+06 - 19) | AXXXXCAGXXAXCACXXACCAGCCC | 27 |
| muhuMSTN-SD2(+08 - 17) | XXXCAGXXAXCACXXACCAGCCCAX | 28 |
| muhuMSTN-SD2(+09 - 16) | XXCAGXXAXCACXXACCAGCCCAXC | 29 |
| muhuMSTN-SD2(+11 - 14) | CAGXXAXCACXXACCAGCCCAXCXX | 30 |
| muhuMSTN-SD2(+12 - 13) | AGXXAXCACXXACCAGCCCAXCXXC | 31 |
| muhuMSTN-SD2(+07 - 16) | XXCAGXXAXCACXXACCAGCCCA | 50 |
| muhuMSTN-SD2(+08 - 16) | XXCAGXXAXCACXXACCAGCCCAX | 51 |
| muhuMSTN-SD2(+01 - 23) | XGXXAXXXXCAGXXAXCACXXACC | 52 |
| muhuMSTN-SD2(+02 - 22) | GXXAXXXXCAGXXAXCACXXACCA | 53 |
| muhuMSTN-SD2(+09 - 15) | XCAGXXAXCACXXACCAGCCCAXC | 54 |
| muhuMSTN-SD2(+06 - 16) | XXCAGXXAXCACXXACCAGCCC | 55 |
| muhuMSTN-SD2(+09 - 14) | CAGXXAXCACXXACCAGCCCAXC | 56 |
| muhuMSTN-SD2(+05 - 16) | XXCAGXXAXCACXXACCAGCC | 57 |
| muhuMSTN-SD2(+09 - 13) | AGXXAXCACXXACCAGCCCAXC | 58 |
| muhuMSTN-SD2(+02 - 19) | AXXXXCAGXXAXCACXXACCA | 59 |
| muhuMSTN-SD2(+04 - 16) | XXCAGXXAXCACXXACCAGC | 60 |
| muhuMSTN-SD2(+02 - 21) | XXAXXXXCAGXXAXCACXXACCA | 61 |
| muhuMSTN-SD2(+02 - 20) | XAXXXXCAGXXAXCACXXACCA | 62 |
| muhuMSTN-SD2(+09 - 12) | GXXAXCACXXACCAGCCCAXC | 63 |
| muhuMSTN-SD2(+02 - 18) | XXXXCAGXXAXCACXXACCA | 64 |
| muhuMSTN-SD2(+09 - 11) | XXAXCACXXACCAGCCCAXC | 65 |

Oligomers with "hu" are human specific and "muhu" both murine and human "X" is selected from either uracil (U) or thymine (T)

Certain antisense oligomers thus comprise, consist, or consist essentially of a sequence in Table 2 (e.g., SEQ ID NOS: 1-5, 10-31 and 50-65), is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T). For instance, certain antisense oligomers comprise about or at least about 12, 13, 14, 15, 16, 17, 18, 19, 20, 21, 22, 23, 24, 25, 26, 27, 28, 29 or 30 contiguous or non-contiguous nucleotides of any of SEQ ID NOS: 1-5, 10-31, or 50-65. For non-contiguous portions, intervening nucleotides can be deleted or substituted with a different nucleotide, or intervening nucleotides can be added. Additional examples of variants include oligomers having about or at least about 90% sequence identity or homology, e.g., 90%, 91%, 92%, 93%, 94%, 95%, 96%, 97%, 98%, 99% or 100% sequence identity or homology, over the entire length of any of SEQ ID NOS: 1-5, 10-31, or 50-65. In preferred embodiments, the targeting sequence is selected from SEQ ID NOS: 16-18.

The activity of antisense oligomers and variants thereof can be assayed according to routine techniques in the art. For example, splice forms and expression levels of surveyed RNAs may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed oligonucleotide) from a cell, tissue or organism, and by hybridizing the mRNA/cDNA with a reference oligonucleotide that is a complement of the assayed nucleic acid, or a fragment thereof. cDNA can, optionally, be amplified using any of a variety of polymerase chain reaction or in vitro transcription methods prior to hybridization with the complementary oligonucleotide; preferably, it is not amplified. Expression of one or more transcripts can also be detected using quantitative PCR to assess the level of expression of the transcript(s).

III. Antisense Oligomer Chemistries

A. General Characteristics

In various aspects and embodiments, the antisense oligomers specifically hybridize to a splice junction region of myostatin pre-mRNA. Exemplary antisense oligomers comprise a targeting sequence set forth in Table 2, a fragment of at least 12 contiguous nucleotides of a targeting sequence in Table 2, or a variant having at least 90% sequence identity to a targeting sequence in Table 2. Other exemplary antisense oligomers consist or consist essentially of a targeting sequence set forth in Table 2.

Nuclease-resistant antisense oligomers are provided in a further aspect. In various embodiments, an antisense oligomer is provided comprising one or more internucleoside linkage modification(s). In other embodiments, an antisense oligomer is provided comprising one or more modified sugar moieties. In other embodiments, an antisense oligomer is provided comprising a combination of one or more modified internucleoside linkages and one or more modified sugar moieties. In other embodiments, an antisense oligomer is provided comprising a modified nucleobase, alone or in combination with any of a modified internucleoside linkage or a modified sugar moiety.

In various embodiments, an antisense oligomer may comprise an oligomer having completely modified internucleoside linkages, for example, 100% of the internucleoside linkages are modified (for example, a 25 mer antisense oligomer comprises 24 internucleoside linkages modified with one or any combination of the modifications as described herein). In various embodiments, an antisense oligomer may comprise about 100% to 2.5% of its internucleoside linkages modified. In various embodiments, an antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its internucleoside linkages modified, and iterations in between. In other embodiments, an antisense oligomer may comprise any combination of modifications as described herein.

In various embodiments, including embodiments in combination with embodiments of percent of modified internucleoside linkages, an antisense oligomer may comprise an oligomer having completely modified sugar moieties, for example, 100% of the sugar moieties are modified (for example, a 25 mer antisense oligomer comprises 25 sugar moieties modified with one or any combination of the modifications as described herein). In various embodiments, an antisense oligomer may comprise about 100% to 2.5% of its sugar moieties modified. In various embodiments, an antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its sugar moieties modified, and iterations in between. In other embodiments, an antisense oligomer may comprise any combination of modifications as described herein.

In various embodiments, the antisense oligomer is substantially uncharged, and is optionally suitable as a substrate for active or facilitated transport across the cell membrane. In some embodiments, all of the internucleoside linkages are uncharged. The ability of the oligomer to form a stable duplex with the target pre-mRNA may also relate to other features of the oligomer, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm.

In various embodiments, the antisense oligomer has at least one internucleoside linkage that is positively charged or cationic at physiological pH. In further embodiments, the antisense oligomer has at least one internucleoside linkage that exhibits a pKa between about 5.5 and about 12. In further embodiments, the antisense oligomer contains about, at least about, or no more than about 1, 2, 3, 4, 5, 6, 7, 8, 9, or 10 internucleoside linkages that exhibits a pKa between about 4.5 and about 12. In some embodiments, the antisense oligomer contains about or at least about 10%, 15%, 20%, 25%, 30%, 35%, 40%, 45%, 50%, 55%, 60%, 65%, 70%, 75%, 80%, 85%, 90%, 95%, or 100% internucleoside linkages that exhibit a pKa between about 4.5 and about 12. Optionally, the antisense oligomer has at least one internucleoside linkage with both a basic nitrogen and an alkyl, aryl, or aralkyl group. In particular embodiments, the cationic internucleoside linkage or linkages comprise a 4-aminopiperdin-1-yl (APN) group, or a derivative thereof. In some embodiments, the antisense oligomer comprises a morpholine ring. While not being bound by theory, it is believed that the presence of a cationic linkage or linkages (e.g., APN group or APN derivative) in the oligomer facilitates binding to the negatively charged phosphates in the target nucleotide. Thus, the formation of a heteroduplex between mutant RNA and the cationic linkage-containing oligomer may be held together by both an ionic attractive force and Watson-Crick base pairing.

In various embodiments, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In some embodiments, however, up to all of the internucleoside linkages are cationic linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are cationic linkages. In further embodiments, an oligomer of about 19-20 monomer subunits may have 2-10, e.g., 4-8, cationic linkages, and the remainder uncharged linkages. In other specific embodiments, an oligomer of 14-15 subunits may have 2-7, e.g., 2, 3, 4, 5, 6, or 7 cationic linkages and the remainder uncharged linkages. The total number of cationic linkages in the oligomer can thus vary from about 1 to 10 to 15 to 20 to 30 or more (including all integers in between), and can be interspersed throughout the oligomer.

In some embodiments, an antisense oligomer may have about or up to about 1 cationic linkage per every 2-5 or 2, 3, 4, or 5 uncharged linkages, such as about 4-5 or 4 or 5 per every 10 uncharged linkages.

Certain embodiments include antisense oligomers that contain about 10%, 15%, 20%, 25%, 30%, 35%, 40%, 45%, 50%, 55%, 60%, 65%, 70%, 75%, 80%, 85%, 90%, 95%, or 100% cationic linkages. In certain embodiments, optimal improvement in antisense activity may be seen if about 25% of the internucleoside linkages are cationic. In certain embodiments, enhancement may be seen with a small number (e.g., 10-20%) of cationic linkages, or where the number of cationic linkages is in the range of 50-80%, such as about 60%.

In further embodiments, the cationic linkages are interspersed along the internucleoside linkage. Such oligomers optionally contain at least two consecutive uncharged linkages; that is, the oligomer optionally does not have a strictly alternating pattern along its entire length. In specific instances, each one or two cationic linkage(s) is/are separated along the internucleoside linkage by at least 1, 2, 3, 4, or 5 uncharged linkages.

Also included are oligomers having blocks of cationic linkages and blocks of uncharged linkages. For example, a central block of uncharged linkages may be flanked by blocks of cationic linkages, or vice versa. In some embodiments, the oligomer has approximately equal-length 5', 3' and center regions, and the percentage of cationic linkages in the center region is greater than about 50%, 60%, 70%, or 80% of the total number of cationic linkages.

In certain antisense oligomers, the bulk of the cationic linkages (e.g., 70%, 75%, 80%, or 90% of the cationic linkages) are distributed close to the "center-region" of the internucleoside linkages, e.g., the 6, 7, 8, 9, 10, 11, 12, 13, 14, or 15 centermost linkages. For example, a 16, 17, 18, 19, 20, 21, 22, 23, or 24-mer oligomer may have at least 50%, 60%, 70%, or 80% of the total cationic linkages localized to the 8, 9, 10, 11, or 12 centermost linkages.

B. Chemistry Features

The antisense oligomers may contain a variety of nucleotide analog subunits. Further examples include:
phosphoroamidate containing oligomers,
phosphorodiamidate containing oligomers,
phosphorothioate containing oligomers,
morpholino containing oligomers optionally substituted with a phosphoramidate internucleoside linkage or a phosphorodiamidate internucleoside linkage,
2'O-methyl containing oligomers optionally substituted with a phosphorothioate internucleoside linkage,
locked nucleic acid (LNA) containing oligomers optionally substituted with a phosphorothioate internucleoside linkage,
2' O-methoxyethyl (MOE) containing oligomers optionally substituted with a phosphorothioate internucleoside linkage,
2'-fluoro-containing oligomers optionally substituted with a phosphorothioate internucleoside linkage,
2'O,4'C-ethylene-bridged nucleic acids (ENAs) containing oligomers optionally substituted with a phosphorothioate internucleoside linkage,
tricyclo-DNA (tc-DNA) containing oligomers optionally substituted with a phosphorothioate internucleoside linkage,
2'-O-[2-(N-methylcarbamoyl)ethyl] containing oligomers optionally substituted with a phosphorothioate internucleoside linkage,
morpholino containing oligomers further comprising a phosphorodiamidate internucleoside linkage wherein the phosphorous atom of the phosphorodiamidate is covalently bonded to the nitrogen atom of a morpholine ring, and is covalently bonded to a (1,4-piperazin)-1-yl moiety or to a substituted (1,4-piperazin)-1-yl (PMOplus) moiety,
morpholino containing oligomers further comprising a phosphorodiamidate internucleoside linkage wherein the phosphorus atom of the phosphorodiamidate is covalently bonded to the nitrogen atom of a morpholine ring and is covalently bonded to a 4-aminopiperdin-1-yl moiety (i.e., APN) or a substituted 4-aminopiperdin-1-yl (PMO-X) moiety,
ribose sugar containing oligomers further comprising a phosphorothioate internucleoside linkage or a phosphoramidate internucleoside linkage,
deoxyribose sugar containing oligomers further comprising a phosphorothioate internucleoside linkage oligomer or a phosphoramidate internucleoside linkage,
peptide-conjugated phosphorodiamidate morpholino containing oligomers (PPMO) which are further optionally substituted,
peptide nucleic acid (PNA) oligomers which are further optionally substituted including further substitutions,
and combinations of any of the foregoing.

In certain embodiments, the phosphorous atom of a phosphorodiamidate linkage is further substituted with a (1,4-piperazin)-1-yl moiety, a substituted (1,4-piperazin)-1-yl moiety, a 4-aminopiperidin-1-yl moiety, or a substituted 4-aminopiperidin-1-yl moiety.

In general, PNA and LNA chemistries can utilize shorter targeting sequences because of their relatively high target binding strength relative to PMO and 2'O-Me oligomers. Phosphorothioate and 2'O-Me chemistries can be combined to generate a 2'O-Me-phosphorothioate analog. See, e.g., PCT Publication Nos. WO/2013/112053 and WO/2009/008725, which are hereby incorporated by reference in their entireties.

In some instances, antisense oligomers, such as phosphorodiamidate morpholino oligomers (PMO), can be covalently bonded to cell penetrating peptides (CPPs) to facilitate intracellular delivery. Peptide-conjugated PMOs are called PPMOs and certain embodiments include those described in PCT Publication No. WO/2012/150960, which is hereby incorporated by reference in its entirety. In some embodiments, an arginine-rich peptide sequence covalently bonded, for example, to the 3' terminal end of an antisense oligomer as described herein may be used.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (Egholm, Buchardt et al. 1993). The internucleoside linkages of PNAs are formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA oligomer comprising PNA subunits is depicted below:

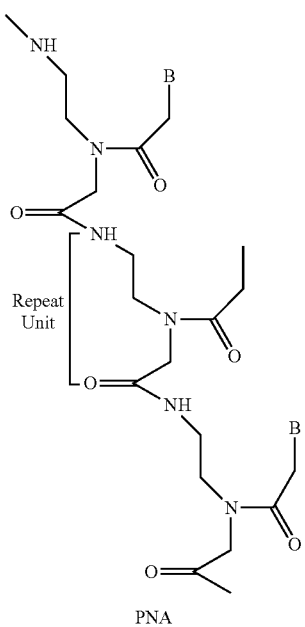

PNA

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE (Daejeon, Korea) has developed Bts PNA monomers (Bts; benzothiazole-2-sulfonyl group) and oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is hereby incorporated by reference in its entirety.

2. Locked Nucleic Acids (LNAs)

Antisense oligomer compounds may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230, which are hereby incorporated by reference in their entirety. A non-limiting example of an LNA oligomer comprising LNA subunits and phosphodiester internucleoside linkages is depicted below:

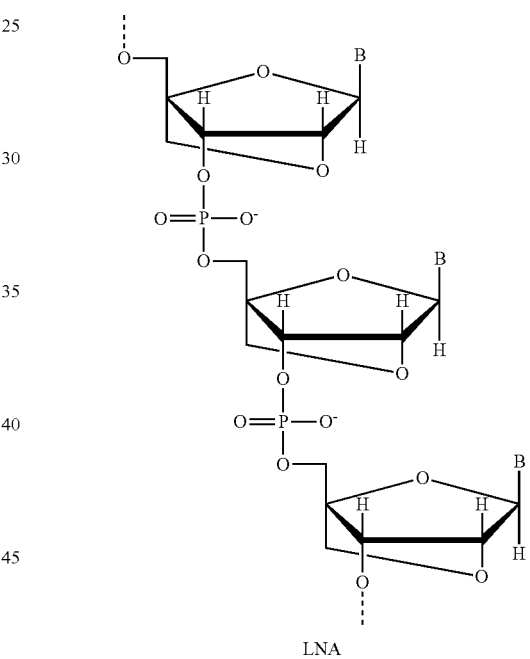

LNA

Compounds of the disclosure may incorporate one or more LNAs; in some cases, the compounds may be entirely composed of LNAs. Methods for the synthesis of individual LNA nucleoside subunits and their incorporation into oligomers are described, for example, in U.S. Pat. Nos. 7,572,582, 7,569,575, 7,084,125, 7,060,809, 7,053,207, 7,034,133, 6,794,499, and 6,670,461, which are hereby incorporated by reference in their entirety. Typical internucleoside linkers include phosphodiester and phosphorothioate moieties; alternatively, non-phosphorous containing linkers may be employed. Further embodiments include an LNA containing compound where each LNA subunit is separated by a DNA subunit. Certain compounds are composed of alternating LNA and DNA subunits where the internucleoside linker is phosphorothioate.

2'O,4'C-ethylene-bridged nucleic acids (ENAs) are another member of the class of BNAs. A non-limiting example of an ENA subunit and phosphodiester internucleoside linkage is depicted below:

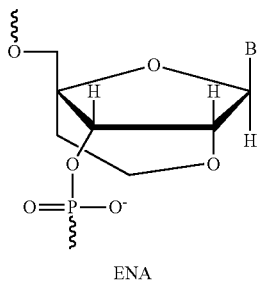

ENA

ENA oligomers and their preparation are described in Obika et al., *Tetrahedron Ltt* 38(50): 8735, which is hereby incorporated by reference in its entirety. Compounds of the disclosure may incorporate one or more ENA subunits.

3. Phosphorothioates

"Phosphorothioates" (or S-oligos) are a variant of native DNA or RNA in which one of the nonbridging oxygens of the phosphodiester internucleoside linkages is replaced by sulfur. A non-limiting example of a phosphorothioate DNA (at left), comprising deoxyribose subunits and phosphorothioate internucleoside linkages, and phosphorothioate RNA (at right), comprising ribose subunits and phosophorothioate internucleoside linkages, are each depicted below:

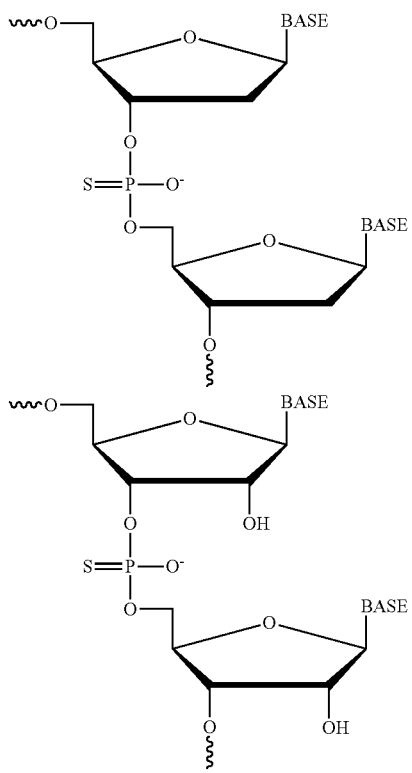

The sulfurization of the internucleoside bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates may be made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990, which are hereby incorporated by reference in their entirety). The latter methods avoid the problem of elemental sulfur's insolubility in most organic solvents and the toxicity of carbon disulfide. The TETD and BDTD methods also yield higher purity phosphorothioates.

4. Tricyclo-DNAs and Tricyclo-Phosphorothioate Nucleotides

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in PCT Publication No. WO 2010/115993, which is hereby incorporated by reference in its entirety. Compounds of the disclosure may incorporate one or more tricyclo-DNA subunits; in some cases, the compounds may be entirely composed of tricyclo-DNA subunits.

Tricyclo-phosphorothioate nucleotides are tricyclo-DNA subunits with phosphorothioate internucleoside linkages. Tricyclo-phosphorothioate nucleotides and their synthesis are described in PCT Publication No. WO 2013/053928, which is hereby incorporated by reference in its entirety. Compounds of the disclosure may incorporate one or more tricyclo-DNA subunits; in some cases, the compounds may be entirely composed of tricyclo-DNA nucleotides. A non-limiting example of a tricyclo-DNA/tricycle subunit and phosphodiester internucleoside linkage is depicted below:

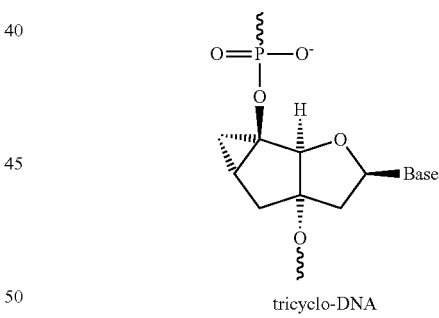

tricyclo-DNA 5. 2' O-Methyl, 2' O-MOE, and 2'-F Oligomers

"2'O-Me oligomer" molecules comprise subunits that carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphorothioate oligomers (PTOs) for further stabilization. 2'O-Me oligomers (wherein the 2'OMe subunits are connected by phosphodiester or phosphorothioate internucleoside linkages) can be synthesized according to routine techniques in the art (see, e.g., Yoo et al., Nucleic Acids Res. 32:2008-16, 2004, which is hereby incorporated by reference in its entirety). A non-limiting example of a 2' O-Me oligomer comprising 2'OMe subunits and phosphodiester intersubunit linkages is depicted below:

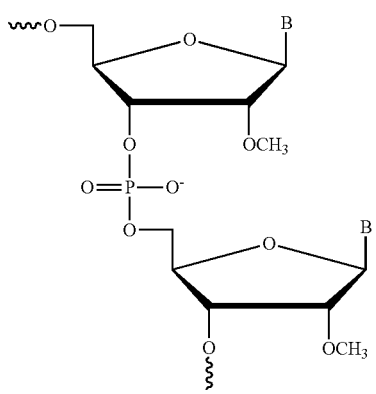

2' O-Me oligomers may also comprise a phosphorothioate linkage (2' O-Me phosphorothioate oligomers). 2' O-Methoxyethyl Oligomers (2'-O MOE), like 2' O-Me oligomers, comprise subunits that carry a methoxyethyl group at the 2'-OH residue of the ribose molecule and are discussed in Martin et al., *Helv. Chim. Acta,* 78, 486-504, 1995, which is hereby incorporated by reference in its entirety. A non-limiting example of a 2' O-MOE subunit is depicted below:

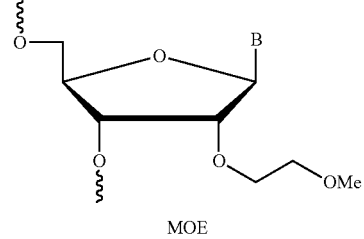

MOE

In contrast to the preceding alkylated 2'OH ribose derivatives, 2'-fluoro oligomers comprise subunits that have a fluoro radical in at the 2' position in place of the 2'OH. A non-limiting example of a 2'-F oligomer comprising 2'-F subunits and phosphodiester internucleoside linkages is depicted below:

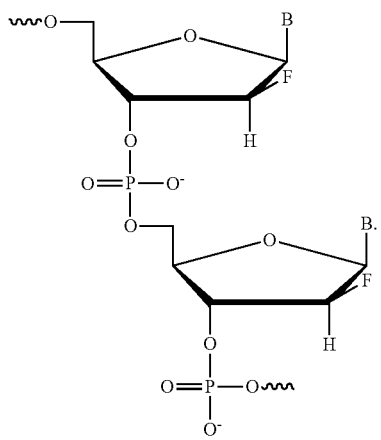

2'-fluoro oligomers are further described in WO 2004/043977, which is hereby incorporated by reference in its entirety. Compounds of the disclosure may incorporate one or more 2'O-Methyl, 2' O-MOE, and 2'-F subunits and may utilize any of the internucleoside linkages described here. In some instances, a compound of the disclosure could be composed of entirely 2'O-Methyl, 2' O-MOE, or 2'-F subunits. One embodiment of a compound of the disclosure is composed entirely of 2'O-methyl subunits.

6. 2'—O-[2-(N-methylcarbamoyl)ethyl] Oligonucleotides (MCEs)

MCEs are another example of 2'O modified ribonucleosides useful in the compounds of the disclosure. Here, the 2'OH is derivatized to a 2-(N-methylcarbamoyl)ethyl moiety to increase nuclease resistance. A non-limiting example of an MCE oligomer comprising MCE subunits and phosphodiester internucleoside linkages is depicted below:

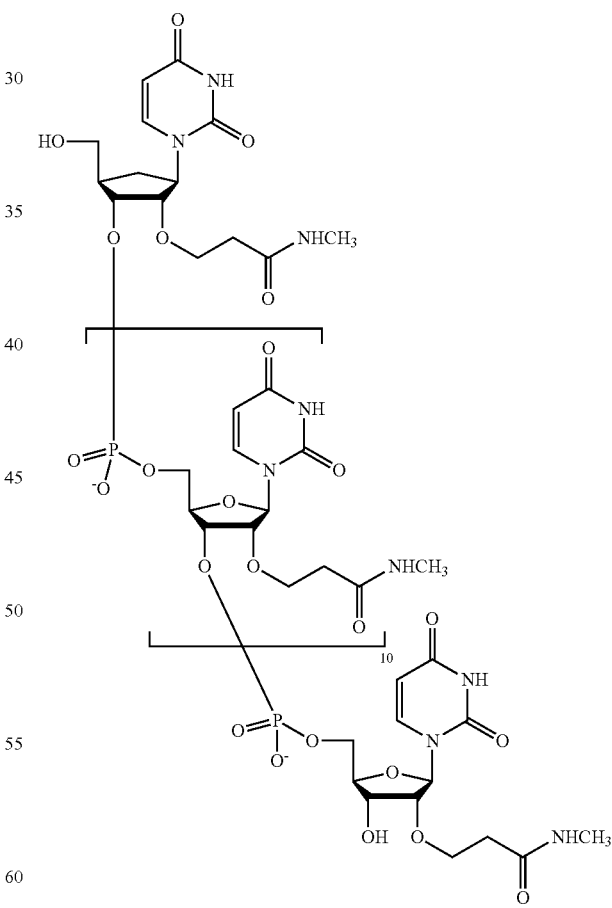

MCEs and their synthesis are described in Yamada et al., J Org. Chem., 76(9):3042-53, which is hereby incorporated by reference in its entirety. Compounds of the disclosure may incorporate one or more MCE subunits.

7. Morpholino-Based Oligomers

Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic internucleoside linkages of the morpholino-based oligomers described herein, one nitrogen is always pendant to the linkage chain. The second nitrogen, in a phosphorodiamidate linkage, is typically the ring nitrogen in a morpholine ring structure.

"PMO-X" refers to phosphorodiamidate morpholino-based oligomers having a phosphorus atom with (i) a covalent bond to the nitrogen atom of a morpholine ring and (ii) a second covalent bond to the ring nitrogen of, for example, a 4-aminopiperdin-1-yl (i.e., APN) or a derivative of 4-aminopiperdin-1-yl. Exemplary PMO-X oligomers are disclosed in PCT Application No. PCT/US2011/38459 and PCT Publication No. WO 2013/074834, which are hereby incorporated by reference in their entirety. PMO-X includes "PMO-apn" or "APN," which refers to a PMO-X oligomer which comprises at least one internucleoside linkage where a phosphorus atom is linked to a morpholino group and to the ring nitrogen of a 4-aminopiperdin-1-yl (i.e., APN). In specific embodiments, an antisense oligomer comprising a targeting sequence as set forth in Table 2 comprises at least one APN-containing linkage or APN derivative-containing linkage. Various embodiments include morpholino-based oligomers that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

In various embodiments, the antisense oligomer is a compound of formula (I):

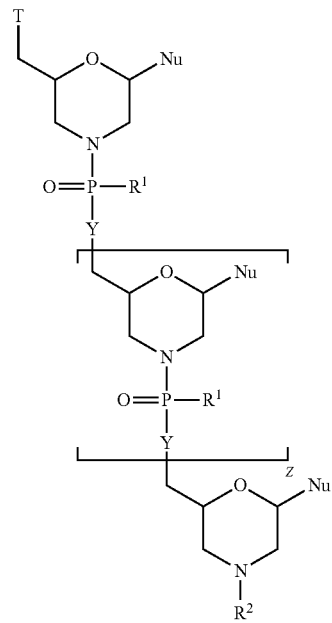

(I)

or a pharmaceutically acceptable salt thereof, wherein:

each Nu is a nucleobase which taken together forms a targeting sequence;

Z is an integer from 10 to 38;

each Y is independently selected from O and —NR$^4$ wherein each R$^4$ is independently selected from H, $C_1$-$C_6$ alkyl, aralkyl, —C(=NH)NH$_2$, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and $C_1$-$C_6$ alkyl and n is an integer from 1 to 5;

T is selected from OH and a moiety of the formula:

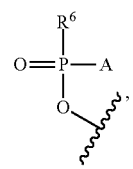

wherein:

A is selected from —OH, —N(R$^7$)$_2$, and R$^1$ wherein:
each R$^7$ is independently selected from H and $C_1$-$C_6$ alkyl, and R$^6$ is selected from OH, —N(R$^9$)CH$_2$C(O)NH$_2$, and a moiety of the formula:

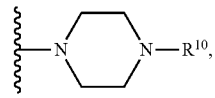

wherein:

R$^9$ is selected from H and $C_1$-$C_6$ alkyl; and

R$^{10}$ is selected from G, —C(O)—R$^{11}$OH, acyl, trityl, 4-methoxytrityl, —C(=NH)NH$_2$, —C(O)(CH$_2$)$_m$NR$^2$C(=NH)NH$_2$, and —C(O)(CH$_2$)$_2$NHC(O)(CH$_2$)$_5$NR$^{12}$C(=NH)NH$_2$,
wherein:
m is an integer from 1 to 5,
R$^{11}$ is of the formula —(O-alkyl)$_y$— wherein y is an integer from 3 to 10 and each of the y alkyl groups is independently selected from C$_2$-C$_6$ alkyl; and
R$^{12}$ is selected from H and C$_1$-C$_6$ alkyl;
each instance of R$^1$ is independently selected from:
—N(R$^{13}$)$_2$ wherein each R$^3$ is independently selected from H and C$_1$-C$_6$ alkyl;
a moiety of formula (II):

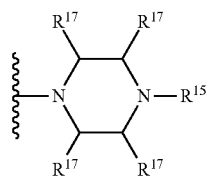

(II)

wherein:
R$^{15}$ is selected from H, G, C$_1$-C$_6$ alkyl, —C(=NH)NH$_2$,
—C(O)(CH$_2$)$_q$NR$^{18}$C(=NH)NH$_2$, and
—C(O)(CH$_2$)$_2$NHC(O)(CH$_2$)$_5$NR$^{18}$C(=NH)NH$_2$, wherein:
R$^{18}$ is selected from H and C$_1$-C$_6$ alkyl; and
q is an integer from 1 to 5; and
each R$^{17}$ is independently selected from H and methyl; and
a moiety of formula (III):

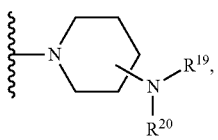

(III)

wherein:
R$^{19}$ is selected from H, C$_1$-C$_6$ alkyl, —C(=NH)NH$_2$,
—C(O)(CH$_2$)$_r$NR$^{22}$C(=NH)NH$_2$, —C(O)CH(NH$_2$)(CH$_2$)$_3$NHC(=NH)NH$_2$,
—C(O)(CH$_2$)$_2$NHC(O)(CH$_2$)$_5$NR$^{22}$C(=NH)NH$_2$,
—C(O)CH(NH$_2$)(CH$_2$)$_4$NH$_2$, and G wherein:
R$^{22}$ is selected from H and C$_1$-C$_6$ alkyl; and
r is an integer from 1 to 5,
R$^{20}$ is selected from H and C$_1$-C$_6$ alkyl; and
R$^2$ is selected from H, G, acyl, trityl, 4-methoxytrityl, C$_1$-C$_6$ alkyl, —C(=NH)NH$_2$, —C(O)—R$^{23}$, —C(O)(CH$_2$)$_s$NR$^{24}$C(=NH)NH$_2$,
—C(O)(CH$_2$)$_2$NHC(O)(CH$_2$)$_5$NR$^{24}$C(=NH)NH$_2$,
—C(O)CH(NH$_2$)(CH$_2$)$_3$NHC(=NH)NH$_2$, and a moiety of the formula:

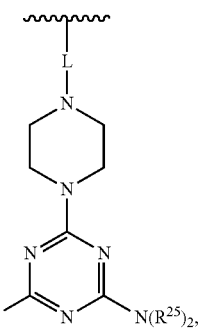

wherein,
R$^{23}$ is of the formula —(O-alkyl)$_v$-OH, wherein v is an integer from 3 to 10 and each of the v alkyl groups is independently selected from C$_2$-C$_6$ alkyl; and
R$^{24}$ is selected from H and C$_1$-C$_6$ alkyl;
s is an integer from 1 to 5;
L is selected from —C(O)(CH$_2$)$_6$C(O)— and —C(O)(CH$_2$)$_2$S$_2$(CH$_2$)$_2$C(O)—; and
each R$^{25}$ is of the formula —(CH$_2$)$_{20}$C(O)N(R$^{26}$)$_2$ wherein each R$^{26}$ is of the formula —(CH$_2$)$_6$NHC(=NH)NH$_2$,
wherein G is a cell penetrating peptide ("CPP") and linker moiety selected
from —C(O)(CH$_2$)$_5$NH—CPP, —C(O)(CH$_2$)$_2$NH—CPP,
—C(O)(CH$_2$)$_2$NHC(O)(CH$_2$)$_5$NH—CPP,
and —C(O)CH$_2$NH—CPP, or G is of the formula:

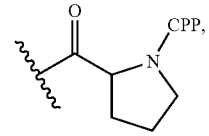

wherein the CPP is attached to the linker moiety by an amide bond at the CPP carboxy terminus, with the proviso that up to one instance of G is present.

In various embodiments, the targeting sequence is complementary to or spanning at least a portion of a splice junction region within intron 1/exon 2 (e.g., SEQ ID NO: 6), or exon 2/intron 2 (e.g., SEQ ID NO: 7, or SEQ ID NO: 8) of the human myostatin pre-mRNA. In some embodiments, the targeting sequence is complementary to 12 or more contiguous nucleotides in a target region spanning an intron/exon junction of human myostatin pre-mRNA, said junction selected from intron 1/exon 2 and exon 2/intron 2. In various embodiments, the contiguous nucleotides include the splice intron/exon junction.

In various embodiments, the targeting sequence comprises one of SEQ ID NOS: 1-5, 10-31, or 50-65, is selected from one of SEQ ID NOS: 1-5, 10-31, or 50-65, is a fragment of at least 12 contiguous nucleotides of a sequence selected from at least one of SEQ ID NOS: 1-5, 10-31, or 50-65, or is a variant having at least 90% sequence identity to a sequence selected from at least one of SEQ ID NOS: 1-5, 10-31, or 50-65, and wherein X is independently selected from uracil (U) or thymine (T). In some embodiments, X is uniformly U or uniformly T.

In some embodiments, the targeting sequence of formula (I) is selected from:

a) SEQ ID NO: 1 (CCAGCC-CAXCXXCXCCXGGXCCXGG) wherein Z is 23;
b) SEQ ID NO: 2 (CACXXACCAGCC-CAXCXXCXCCXGG) wherein Z is 23;
c) SEQ ID NO: 3 (CCAXCCACXXGCAXX-AGAAAAXCAGC) wherein Z is 24;
d) SEQ ID NO: 4 (GCAXXAGAAAAXCAGCXAX-AAAXG) wherein Z is 22;
e) SEQ ID NO: 5 (CCACXXGCAXXAGAAAAX-CAGC) wherein Z is 20;
f) SEQ ID NO: 10 (CXXGCAXXAGAAAAX-CAGCXAXAAA) wherein Z is 23;
g) SEQ ID NO: 11 (CACXXGCAXXAGAAAAX-CAGCXAXA) wherein Z is 23;
h) SEQ ID NO: 12 (CCACXXGCAXXAGAAAAX-CAGCXAX) wherein Z is 23;
i) SEQ ID NO: 13 (XCCACXXGCAXXAGAAAAX-CAGCXA) wherein Z is 23;
j) SEQ ID NO: 14 (AXCCACXXGCAXXAGAAAAX-CAGCX) wherein Z is 23;
k) SEQ ID NO: 15 (CAXCCACXXGCAXX-AGAAAAXCAGC) wherein Z is 23;
l) SEQ ID NO: 16 (XXAXXXXCAGXXAXCACXX-ACCAGC) wherein Z is 23;
m) SEQ ID NO: 17 (XXXXCAGXXAXCACXX-ACCAGCCCA) wherein Z is 23;
n) SEQ ID NO: 18 (XCAGXXAXCACXXACCAGCC-CAXCX) wherein Z is 23;
o) SEQ ID NO: 19 (GXXAXCACXXACCAGCC-CAXCXXCX) wherein Z is 23;
p) SEQ ID NO: 20 (AXCACXXACCAGCC-CAXCXXCXCCX) wherein Z is 23;
q) SEQ ID NO: 21 (ACXXACCAGCC-CAXCXXCXCCXGGX) wherein Z is 23;
r) SEQ ID NO: 22 (XACCAGCC-CAXCXXCXCCXGGXCCX) wherein Z is 23;
s) SEQ ID NO: 23 (AXGXXAXXXXCAGXXAX-CACXXACC) wherein Z is 23;
t) SEQ ID NO: 24 (XGXXAXXXXCAGXXAXCACXX-ACCA) wherein Z is 23;
u) SEQ ID NO: 25 (GXXAXXXXCAGXXAXCACXX-ACCAG) wherein Z is 23;
v) SEQ ID NO: 26 (XAXXXXCAGXXAXCACXX-ACCAGCC) wherein Z is 23;
w) SEQ ID NO: 27 (AXXXXCAGXXAXCACXX-ACCAGCCC) wherein Z is 23;
x) SEQ ID NO: 28 (XXXCAGXXAXCACXX-ACCAGCCCAX) wherein Z is 23;
y) SEQ ID NO: 29 (XXCAGXXAXCACXXACCAGCC-CAXC) wherein Z is 23;
z) SEQ ID NO: 30 (CAGXXAXCACXXACCAGCC-CAXCXX) wherein Z is 23;
aa) SEQ ID NO: 31 (AGXXAXCACXXACCAGCC-CAXCXXC) wherein Z is 23;
bb) SEQ ID NO: 50 (XXCAGXXAXCACXX-ACCAGCCCA) wherein Z is 21;
cc) SEQ ID NO: 51 (XXCAGXXAXCACXX-ACCAGCCCAX) wherein Z is 22;
dd) SEQ ID NO: 52 (XGXXAXXXXCAGXXAX-CACXXACC) wherein Z is 22;
ee) SEQ ID NO: 53 (GXXAXXXXCAGXXAXCACXX-ACCA) wherein Z is 22;
ff) SEQ ID NO: 54 (XCAGXXAXCACXXACCAGCC-CAXC) wherein Z is 22;
gg) SEQ ID NO: 55 (XXCAGXXAXCACXX-ACCAGCCC) wherein Z is 20;
hh) SEQ ID NO: 56 (CAGXXAXCACXXACCAGCC-CAXC) wherein Z is 21;
ii) SEQ ID NO: 57 (XXCAGXXAXCACXXACCAGCC) wherein Z is 19;
jj) SEQ ID NO: 58 (AGXXAXCACXXACCAGCC-CAXC) wherein Z is 20;
kk) SEQ ID NO: 59 (AXXXXCAGXXAXCACXX-ACCA) wherein Z is 19;
ll) SEQ ID NO: 60 (XXCAGXXAXCACXXACCAGC) wherein Z is 18;
mm) SEQ ID NO: 61 (XXAXXXXCAGXXAXCACXX-ACCA) wherein Z is 21;
nn) SEQ ID NO: 62 (XAXXXXCAGXXAXCACXX-ACCA) wherein Z is 20;
oo) SEQ ID NO: 63 (GXXAXCACXXACCAGCC-CAXC) wherein Z is 19;
pp) SEQ ID NO: 64 (XXXXCAGXXAXCACXXACCA) wherein Z is 18; and
qq) SEQ ID NO: 65 (XXAXCACXXACCAGCCCAXC) wherein Z is 18,
and wherein X is independently selected from uracil (U) or thymine (T).

In some embodiments, $R^3$ is a moiety of the formula:

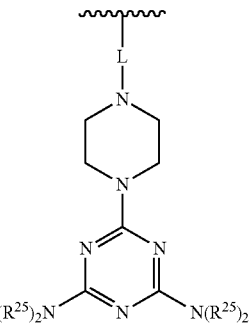

where L is selected from —C(O)(CH$_2$)$_6$C(O)— or —C(O)(CH$_2$)$_2$S$_2$(CH$_2$)$_2$C(O)—, and
and each $R^{25}$ is of the formula —(CH$_2$)$_{20}$C(O)N(R$^{26}$)$_2$ wherein each $R^{26}$ is of the formula —(CH$_2$)$_6$NHC(=NH)NH$_2$. Such moieties are further described in U.S. Pat. No. 7,935,816, which is hereby incorporated by reference in its entirety.

In certain embodiments, $R^3$ may comprise either moiety depicted below:

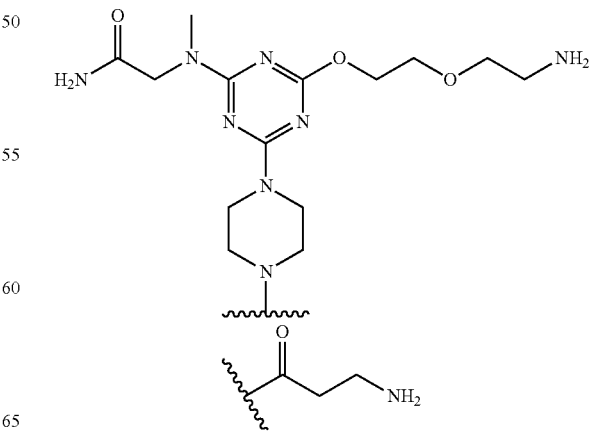

In various embodiments, Y is O, $R^2$ is selected from H or G, $R^3$ is selected from an electron pair or H. In some embodiments, $R^2$ is G wherein the CPP is of a sequence selected from SEQ ID NOS: 32-47. In certain embodiments, $R^2$ is H.

In certain embodiments, each $R^1$ is —$N(CH_3)_2$. In some embodiments, about 50-90% of the $R_1$ groups are dimethylamino (i.e. —$N(CH_3)_2$). In certain embodiments, about 66% of the $R_1$ groups are dimethylamino.

In some embodiments of the disclosure, $R_1$ may be selected from:

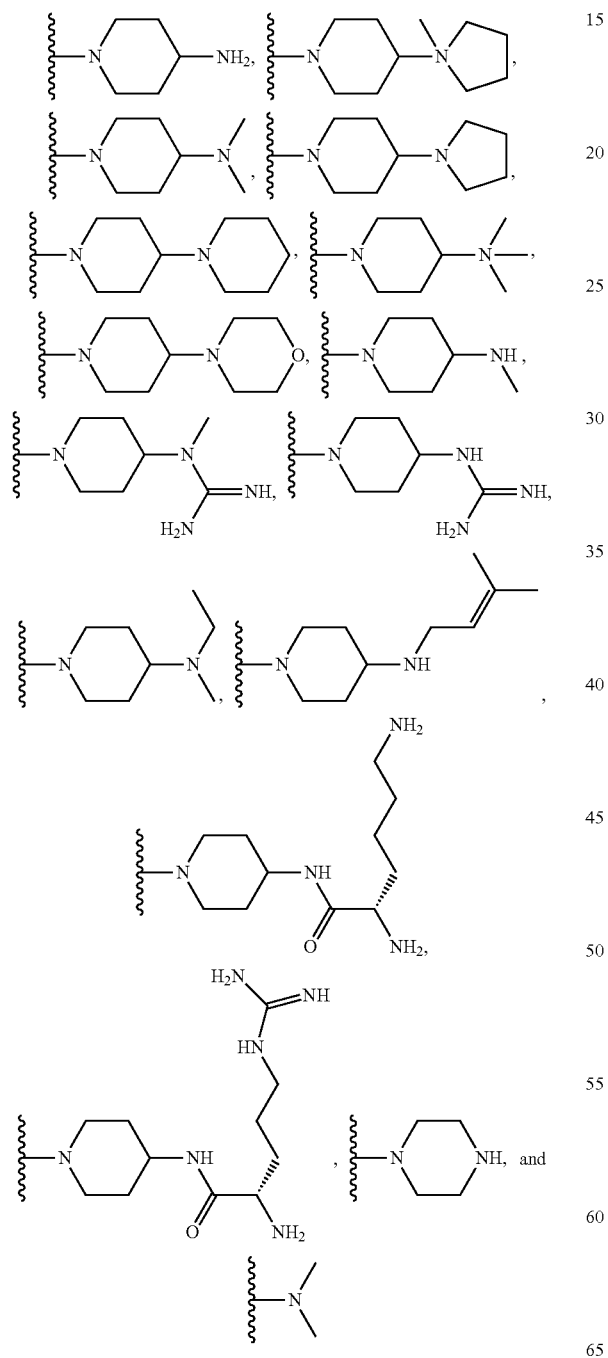

In some embodiments, at least one $R^1$ is:

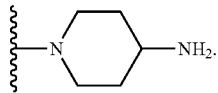

In some embodiments, T is of the formula:

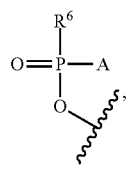

wherein A is —$N(CH_3)_2$, and $R^6$ is of the formula:

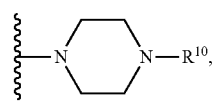

wherein $R^{10}$ is —$C(O)R^{11}OH$, wherein
$R^{11}$ is of the formula —$(O\text{-alkyl})_y$— wherein y is an integer from 3 to 10 and
each of the y alkyl groups is independently selected from $C_2$-$C_6$ alkyl.

In some embodiments, Y is O, and T is selected from:

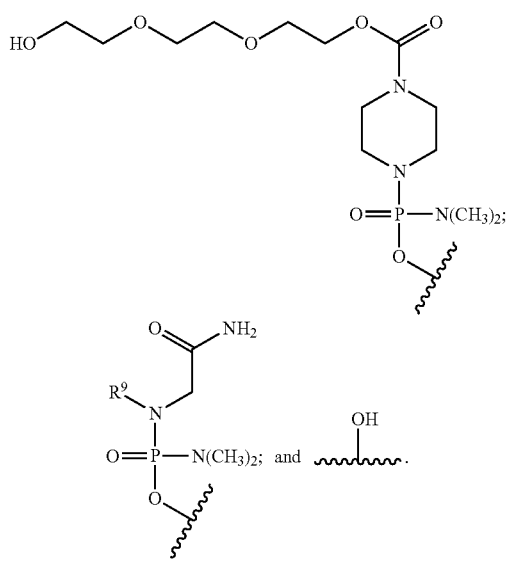

In certain embodiments, T is of the formula:

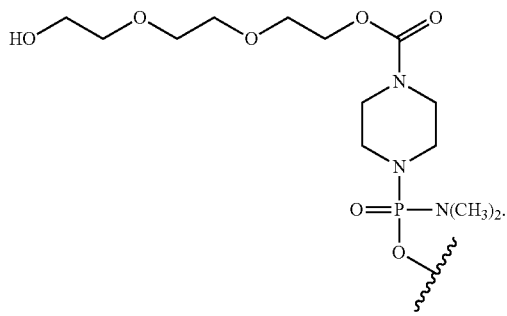 [SMILES: *OP(=O)(N(C)C)N1CCN(C(=O)OCCOCCOCCO)CC1]

In various embodiments, Y is O, R² is selected from H or G, R³ is selected from an electron pair or H. In some embodiments, R² is G, wherein the CPP is of a sequence selected from SEQ ID NOS: 32-47 described below.

In other embodiments, the antisense oligomer is a compound of formula (IV):

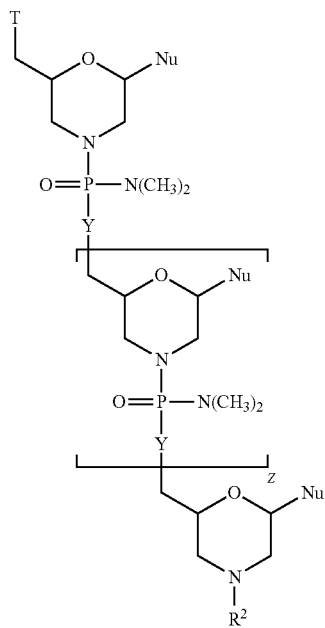

(IV)

or a pharmaceutically acceptable salt thereof, where:
each Nu is a nucleobase which taken together forms a targeting sequence;
Z is an integer from 10 to 38;
each Y is independently selected from O and —NR⁴, wherein each R⁴ is independently selected from H, $C_1$-$C_6$ alkyl, aralkyl, —C(=NH)NH₂, —C(O)(CH₂)₁NR⁵C(=NH)NH₂,
—C(O)(CH₂)₂NHC(O)(CH₂)₅NR⁵C(=NH)NH₂, and G, wherein R⁵ is selected from H and $C_1$-$C_6$ alkyl and n is an integer from 1 to 5;

T is selected from OH and a moiety of the formula:

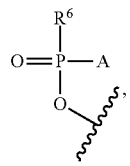

wherein:
A is selected from —OH and —N(R⁷)₂, wherein:
each R⁷ is independently selected from H and $C_1$-$C_6$ alkyl, and
R⁶ is selected from OH, —N(R⁹)CH₂C(O)NH₂, and a moiety of the formula:

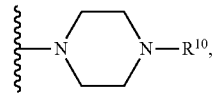

wherein:
R⁹ is selected from H and $C_1$-$C_6$ alkyl; and
R¹⁰ is selected from G, —C(O)—R¹¹OH, acyl, trityl, 4-methoxytrityl,
—C(=NH)NH₂, —C(O)(CH₂)$_m$NR¹²C(=NH)NH₂, and
—C(O)(CH₂)₂NHC(O)(CH₂)₅NR¹²C(=NH)NH₂,
wherein:
m is an integer from 1 to 5,
R¹¹ is of the formula —(O-alkyl)$_y$—wherein y is an integer from 3 to 10 and each of the y alkyl groups is independently selected from $C_2$-$C_6$ alkyl; and
R¹² is selected from H and $C_1$-$C_6$ alkyl; and
R² is selected from H, G, acyl, trityl, 4-methoxytrityl, $C_1$-$C_6$ alkyl, —C(=NH)NH₂, and —C(O)—R²³.

In various embodiments, the targeting sequence is complementary to or spans at least a portion of a splice junction region within intron 1/exon 2 (e.g., SEQ ID NO: 6) or exon 2/intron 2 (e.g., SEQ ID NO: 7, or SEQ ID NO: 8) of the human myostatin pre-mRNA. In some embodiments, the targeting sequence is complementary to 12 or more contiguous nucleotides in a target region spanning an intron/exon junction of human myostatin pre-mRNA, said junction selected from intron 1/exon 2 and exon 2/intron 2. In various embodiments, the contiguous nucleotides include the splice intron/exon junction.

In various embodiments, the targeting sequence of compound (IV) comprises a sequence selected from SEQ ID NOS:1-5, 10-31, or 50-65, is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T). In some embodiments, X is uniformly U or uniformly T.

In some embodiments, the targeting sequence of formula (IV) is selected from:
a) SEQ ID NO: 1 (CCAGCC-CAXCXXCXCCXGGXCCXGG) wherein Z is 23;
b) SEQ ID NO: 2 (CACXXACCAGCC-CAXCXXCXCCXGG) wherein Z is 23;
c) SEQ ID NO: 3 (CCAXCCACXXGCAXX-AGAAAAXCAGC) wherein Z is 24;

d) SEQ ID NO: 4 (GCAXXAGAAAAXCAGCXAX-AAAXG) wherein Z is 22;

e) SEQ ID NO: 5 (CCACXXGCAXXAGAAAAX-CAGC) wherein Z is 20;

f) SEQ ID NO: 10 (CXXGCAXXAGAAAAX-CAGCXAXAAA) wherein Z is 23;

g) SEQ ID NO: 11 (CACXXGCAXXAGAAAAX-CAGCXAXA) wherein Z is 23;

h) SEQ ID NO: 12 (CCACXXGCAXXAGAAAAX-CAGCXAX) wherein Z is 23;

i) SEQ ID NO: 13 (XCCACXXGCAXXAGAAAAX-CAGCXA) wherein Z is 23;

j) SEQ ID NO: 14 (AXCCACXXGCAXXAGAAAAX-CAGCX) wherein Z is 23;

k) SEQ ID NO: 15 (CAXCCACXXGCAXX-AGAAAAXCAGC) wherein Z is 23;

l) SEQ ID NO: 16 (XXAXXXXCAGXXAXCACXX-ACCAGC) wherein Z is 23;

m) SEQ ID NO: 17 (XXXXCAGXXAXCACXX-ACCAGCCCA) wherein Z is 23;

n) SEQ ID NO: 18 (XCAGXXAXCACXXACCAGCC-CAXCX) wherein Z is 23;

o) SEQ ID NO: 19 (GXXAXCACXXACCAGCC-CAXCXXCX) wherein Z is 23;

p) SEQ ID NO: 20 (AXCACXXACCAGCC-CAXCXXCXCCX) wherein Z is 23;

q) SEQ ID NO: 21 (ACXXACCAGCC-CAXCXXCXCCXGGX) wherein Z is 23;

r) SEQ ID NO: 22 (XACCAGCC-CAXCXXCXCCXGGXCCX) wherein Z is 23;

s) SEQ ID NO: 23 (AXGXXAXXXXCAGXXAX-CACXXACC) wherein Z is 23;

t) SEQ ID NO: 24 (XGXXAXXXXCAGXXAXCACXX-ACCA) wherein Z is 23;

u) SEQ ID NO: 25 (GXXAXXXXCAGXXAXCACXX-ACCAG) wherein Z is 23;

v) SEQ ID NO: 26 (XAXXXXCAGXXAXCACXX-ACCAGCC) wherein Z is 23;

w) SEQ ID NO: 27 (AXXXXCAGXXAXCACXX-ACCAGCCC) wherein Z is 23;

x) SEQ ID NO: 28 (XXXCAGXXAXCACXX-ACCAGCCCAX) wherein Z is 23;

y) SEQ ID NO: 29 (XXCAGXXAXCACXXACCAGCC-CAXC) wherein Z is 23;

z) SEQ ID NO: 30 (CAGXXAXCACXXACCAGCC-CAXCXX) wherein Z is 23;

aa) SEQ ID NO: 31 (AGXXAXCACXXACCAGCC-CAXCXXC) wherein Z is 23;

bb) SEQ ID NO: 50 (XXCAGXXAXCACXX-ACCAGCCCA) wherein Z is 21;

cc) SEQ ID NO: 51 (XXCAGXXAXCACXX-ACCAGCCCAX) wherein Z is 22;

dd) SEQ ID NO: 52 (XGXXAXXXXCAGXXAX-CACXXACC) wherein Z is 22;

ee) SEQ ID NO: 53 (GXXAXXXXCAGXXAXCACXX-ACCA) wherein Z is 22;

ff) SEQ ID NO: 54 (XCAGXXAXCACXXACCAGCC-CAXC) wherein Z is 22;

gg) SEQ ID NO: 55 (XXCAGXXAXCACXX-ACCAGCCC) wherein Z is 20;

hh) SEQ ID NO: 56 (CAGXXAXCACXXACCAGCC-CAXC) wherein Z is 21;

ii) SEQ ID NO: 57 (XXCAGXXAXCACXXACCAGCC) wherein Z is 19;

jj) SEQ ID NO: 58 (AGXXAXCACXXACCAGCC-CAXC) wherein Z is 20;

kk) SEQ ID NO: 59 (AXXXXCAGXXAXCACXX-ACCA) wherein Z is 19;

ll) SEQ ID NO: 60 (XXCAGXXAXCACXXACCAGC) wherein Z is 18;

mm) SEQ ID NO: 61 (XXAXXXXCAGXXAXCACXX-ACCA) wherein Z is 21;

nn) SEQ ID NO: 62 (XAXXXXCAGXXAXCACXX-ACCA) wherein Z is 20;

oo) SEQ ID NO: 63 (GXXAXCACXXACCAGCC-CAXC) wherein Z is 19;

pp) SEQ ID NO: 64 (XXXXCAGXXAXCACXXACCA) wherein Z is 18; and qq) SEQ ID NO: 65 (XXAXCACXXACCAGCCCAXC) wherein Z is 18;

and wherein X is independently selected from uracil (U) or thymine (T).

In various embodiments, Y is O, $R^2$ is selected from H or G, $R^3$ is selected from an electron pair or H. In some embodiments, $R^2$ is G, wherein the CPP is of a sequence selected from SEQ ID NOS: 32-47. In certain embodiments, $R^2$ is H.

In some embodiments, Y is O, and T is selected from:

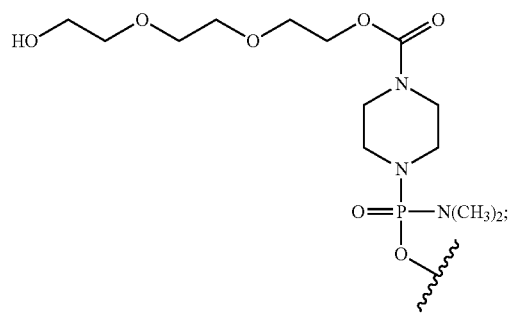

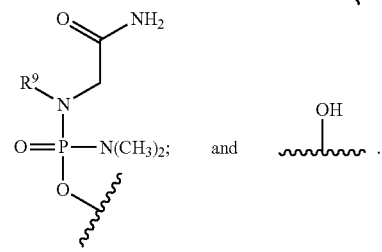

In some embodiments, T is of the formula:

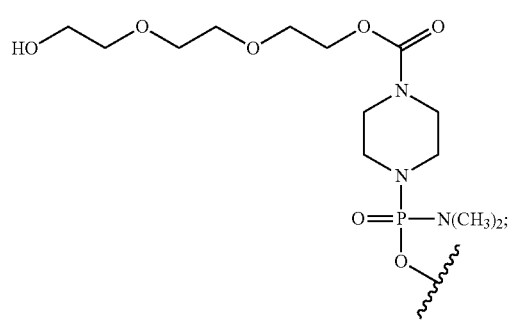 [SMILES: *OP(=O)(N(C)C)N1CCN(C(=O)OCCOCCOCCO)CC1]

$R^2$ is hydrogen; and $R^3$ is an electron pair.

In some embodiments, the antisense oligomer is a compound of formula (V):

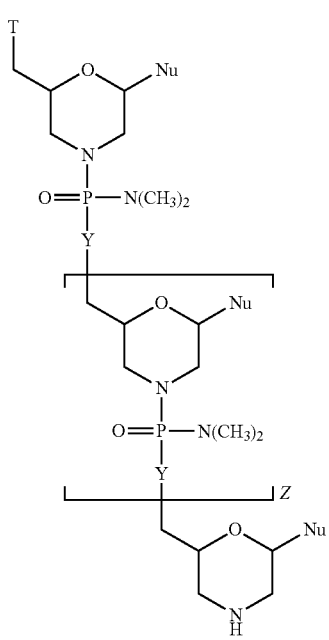

(V)

or a pharmaceutically acceptable salt thereof, where:
each Nu is a nucleobase which taken together forms a targeting sequence;
Z is an integer from 10 to 38;
each Y is independently selected from O and —NR$^4$ wherein each R$^4$ is independently selected from H, $C_1$-$C_6$ alkyl, aralkyl, —C(=NH)NH$_2$, —C(O)(CH$_2$)$_1$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and $C_1$-$C_6$ alkyl and n is an integer from 1 to 5;
T is selected from OH and a moiety of the formula:

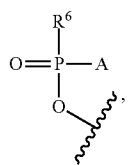

wherein:
A is selected from —OH and —N(R$^7$)$_2$, wherein:
each R$^7$ is independently selected from H and $C_1$-$C_6$ alkyl, and
R$^6$ is selected from OH, —N(R$^9$)CH$_2$C(O)NH$_2$, and a moiety of the formula:

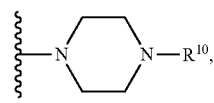

wherein:
R$^9$ is selected from H and $C_1$-$C_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^2$C(=NH)NH$_2$, and —C(O)(CH$_2$)$_2$NHC(O)(CH$_2$)$_5$NR$^{12}$C(=NH)NH$_2$,
wherein:
m is an integer from 1 to 5,
R$^{11}$ is of the formula —(O-alkyl)$_y$—, wherein y is an integer from 3 to 10 and
each of the y alkyl groups is independently selected from $C_2$-$C_6$ alkyl; and
R$^{12}$ is selected from H and $C_1$-$C_6$ alkyl;
wherein G is a cell penetrating peptide ("CPP") and linker moiety selected
from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP,
and —C(O)CH$_2$NH—CPP, or G is of the formula:

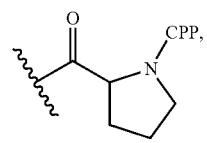

wherein the CPP is attached to the linker moiety by an amide bond at the CPP carboxy terminus, with the proviso that up to one instance of G is present.

In various embodiments, the targeting sequence is complementary to or spans at least a portion of a splice junction region within intron 1/exon 2 (e.g., SEQ ID NO: 6) or exon 2/intron 2 (e.g., SEQ ID NO: 7, or SEQ ID NO: 8) of a human myostatin pre-mRNA. In some embodiments, the targeting sequence is complementary to 12 or more contiguous nucleotides in a target region spanning an intron/exon junction of human myostatin pre-mRNA, said junction selected from intron 1/exon 2 and exon 2/intron 2. In various embodiments, the contiguous nucleotides include the splice intron/exon junction.

In various embodiments, the targeting sequence of compound (V) comprises a sequence selected from SEQ ID NOS: 1-5, 10-31, or 50-65, is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T). In some embodiments, X is uniformly U or uniformly T.

In some embodiments, the targeting sequence of formula (V) is selected from:
a) SEQ ID NO: 1 (CCAGCCCAXCXXCXCCXGGXCCXGG) wherein Z is 23;
b) SEQ ID NO: 2 (CACXXACCAGCCCAXCXXCXCCXGG) wherein Z is 23;
c) SEQ ID NO: 3 (CCAXCCACXXGCAXXAGAAAAXCAGC) wherein Z is 24;
d) SEQ ID NO: 4 (GCAXXAGAAAAXCAGCXAXAAAXG) wherein Z is 22;
e) SEQ ID NO: 5 (CCACXXGCAXXAGAAAAXCAGC) wherein Z is 20;
f) SEQ ID NO: 10 (CXXGCAXXAGAAAAXCAGCXAXAAA) wherein Z is 23;
g) SEQ ID NO: 11 (CACXXGCAXXAGAAAAXCAGCXAXA) wherein Z is 23;
h) SEQ ID NO: 12 (CCACXXGCAXXAGAAAAXCAGCXAX) wherein Z is 23;
i) SEQ ID NO: 13 (XCCACXXGCAXXAGAAAAXCAGCXA) wherein Z is 23;

j) SEQ ID NO: 14 (AXCCACXXGCAXXAGAAAAX-CAGCX) wherein Z is 23;

k) SEQ ID NO: 15 (CAXCCACXXGCAXX-AGAAAAXCAGC) wherein Z is 23;

l) SEQ ID NO: 16 (XXAXXXXCAGXXAXCACXX-ACCAGC) wherein Z is 23;

m) SEQ ID NO: 17 (XXXXCAGXXAXCACXX-ACCAGCCCA) wherein Z is 23;

n) SEQ ID NO: 18 (XCAGXXAXCACXXACCAGCC-CAXCX) wherein Z is 23;

o) SEQ ID NO: 19 (GXXAXCACXXACCAGCC-CAXCXXCX) wherein Z is 23;

p) SEQ ID NO: 20 (AXCACXXACCAGCC-CAXCXXCXCCX) wherein Z is 23;

q) SEQ ID NO: 21 (ACXXACCAGCC-CAXCXXCXCCXGGX) wherein Z is 23;

r) SEQ ID NO: 22 (XACCAGCC-CAXCXXCXCCXGGXCCX) wherein Z is 23;

s) SEQ ID NO: 23 (AXGXXAXXXXCAGXXAX-CACXXACC) wherein Z is 23;

t) SEQ ID NO: 24 (XGXXAXXXXCAGXXAXCACXX-ACCA) wherein Z is 23;

u) SEQ ID NO: 25 (GXXAXXXXCAGXXAXCACXX-ACCAG) wherein Z is 23;

v) SEQ ID NO: 26 (XAXXXXCAGXXAXCACXX-ACCAGCC) wherein Z is 23;

w) SEQ ID NO: 27 (AXXXXCAGXXAXCACXX-ACCAGCCC) wherein Z is 23;

x) SEQ ID NO: 28 (XXXCAGXXAXCACXX-ACCAGCCCAX) wherein Z is 23;

y) SEQ ID NO: 29 (XXCAGXXAXCACXXACCAGCC-CAXC) wherein Z is 23;

z) SEQ ID NO: 30 (CAGXXAXCACXXACCAGCC-CAXCXX) wherein Z is 23;

aa) SEQ ID NO: 31 (AGXXAXCACXXACCAGCC-CAXCXXC) wherein Z is 23;

bb) SEQ ID NO: 50 (XXCAGXXAXCACXX-ACCAGCCCA) wherein Z is 21;

cc) SEQ ID NO: 51 (XXCAGXXAXCACXX-ACCAGCCCAX) wherein Z is 22;

dd) SEQ ID NO: 52 (XGXXAXXXXCAGXXAX-CACXXACC) wherein Z is 22;

ee) SEQ ID NO: 53 (GXXAXXXXCAGXXAXCACXX-ACCA) wherein Z is 22;

ff) SEQ ID NO: 54 (XCAGXXAXCACXXACCAGCC-CAXC) wherein Z is 22;

gg) SEQ ID NO: 55 (XXCAGXXAXCACXX-ACCAGCCC) wherein Z is 20;

hh) SEQ ID NO: 56 (CAGXXAXCACXXACCAGCC-CAXC) wherein Z is 21;

ii) SEQ ID NO: 57 (XXCAGXXAXCACXXACCAGCC) wherein Z is 19;

jj) SEQ ID NO: 58 (AGXXAXCACXXACCAGCC-CAXC) wherein Z is 20;

kk) SEQ ID NO: 59 (AXXXXCAGXXAXCACXX-ACCA) wherein Z is 19;

ll) SEQ ID NO: 60 (XXCAGXXAXCACXXACCAGC) wherein Z is 18;

mm) SEQ ID NO: 61 (XXAXXXXCAGXXAXCACXX-ACCA) wherein Z is 21;

nn) SEQ ID NO: 62 (XAXXXXXCAGXXAXCACXX-ACCA) wherein Z is 20;

oo) SEQ ID NO: 63 (GXXAXCACXXACCAGCC-CAXC) wherein Z is 19;

pp) SEQ ID NO: 64 (XXXXCAGXXAXCACXXACCA) wherein Z is 18; and qq) SEQ ID NO: 65 (XXAXCACXXACCAGCCCAXC) wherein Z is 18;

and wherein X is independently selected from uracil (U) or thymine (T).

In some embodiments, Y is O, and T is selected from:

In some embodiments, T is of the formula:

In certain embodiments, the antisense oligomer of the disclosure is a compound of formula (VI):

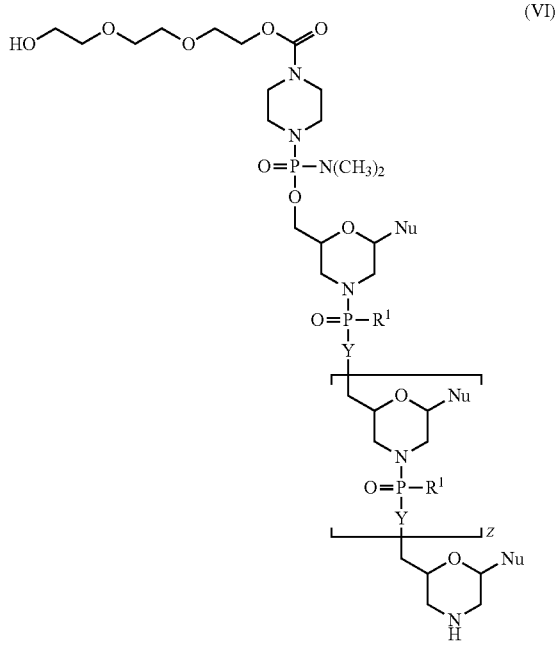

(VI)

or a pharmaceutically acceptable salt thereof, where:
each Nu is a nucleobase which taken together form a targeting sequence;
Z is an integer from 15 to 25;
each Y is O;
each R¹ is independently selected from:

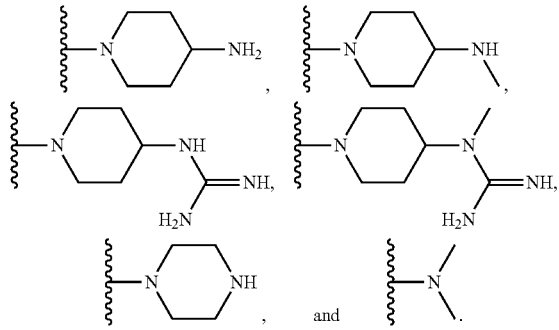

In various embodiments, at least one R¹ is —N(CH₃)₂. In some embodiments, each R¹ is —N(CH₃)₂.

In various embodiments, the targeting sequence is complementary to or spans at least a portion of a splice junction region within intron 1/exon 2 (e.g., SEQ ID NO: 6) or exon 2/intron 2 (e.g., SEQ ID NO: 7, or SEQ ID NO: 8) of the human myostatin pre-mRNA. In some embodiments, the targeting sequence is complementary to 12 or more contiguous nucleotides in a target region spanning an intron/exon junction of human myostatin pre-mRNA, said junction selected from intron 1/exon 2 and exon 2/intron 2. In various embodiments, the contiguous nucleotides include the splice intron/exon junction.

In various embodiments, the targeting sequence of compound (VI) comprises a sequence selected from SEQ ID NOS: 1-5, 10-31, or 50-65, is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T).

In some embodiments, the targeting sequence of formula (VI) is selected from:
a) SEQ ID NO: 1 (CCAGCC-CAXCXXCXCCXGGXCCXGG) wherein Z is 23;
b) SEQ ID NO: 2 (CACXXACCAGCC-CAXCXXCXCCXGG) wherein Z is 23;
c) SEQ ID NO: 3 (CCAXCCACXXGCAXX-AGAAAAXCAGC) wherein Z is 24;
d) SEQ ID NO: 4 (GCAXXAGAAAAXCAGCXAX-AAAXG) wherein Z is 22;
e) SEQ ID NO: 5 (CCACXXGCAXXAGAAAAX-CAGC) wherein Z is 20;
f) SEQ ID NO: 10 (CXXGCAXXAGAAAAX-CAGCXAXAAA) wherein Z is 23;
g) SEQ ID NO: 11 (CACXXGCAXXAGAAAAX-CAGCXAXA) wherein Z is 23;
h) SEQ ID NO: 12 (CCACXXGCAXXAGAAAAX-CAGCXAX) wherein Z is 23;
i) SEQ ID NO: 13 (XCCACXXGCAXXAGAAAAX-CAGCXA) wherein Z is 23;
j) SEQ ID NO: 14 (AXCCACXXGCAXXAGAAAAX-CAGCX) wherein Z is 23;
k) SEQ ID NO: 15 (CAXCCACXXGCAXX-AGAAAAXCAGC) wherein Z is 23;
l) SEQ ID NO: 16 (XXAXXXXCAGXXAXCACXX-ACCAGC) wherein Z is 23;
m) SEQ ID NO: 17 (XXXXCAGXXAXCACXX-ACCAGCCCA) wherein Z is 23;
n) SEQ ID NO: 18 (XCAGXXAXCACXXACCAGCC-CAXCX) wherein Z is 23;
o) SEQ ID NO: 19 (GXXAXCACXXACCAGCC-CAXCXXCX) wherein Z is 23;
p) SEQ ID NO: 20 (AXCACXXACCAGCC-CAXCXXCXCCX) wherein Z is 23;
q) SEQ ID NO: 21 (ACXXACCAGCC-CAXCXXCXCCXGGX) wherein Z is 23;
r) SEQ ID NO: 22 (XACCAGCC-CAXCXXCXCCXGGXCCX) wherein Z is 23;
s) SEQ ID NO: 23 (AXGXXAXXXXCAGXXAX-CACXXACC) wherein Z is 23;
t) SEQ ID NO: 24 (XGXXAXXXXCAGXXAXCACXX-ACCA) wherein Z is 23;
u) SEQ ID NO: 25 (GXXAXXXXCAGXXAXCACXX-ACCAG) wherein Z is 23;
v) SEQ ID NO: 26 (XAXXXXCAGXXAXCACXX-ACCAGCC) wherein Z is 23;
w) SEQ ID NO: 27 (AXXXXCAGXXAXCACXX-ACCAGCCC) wherein Z is 23;
x) SEQ ID NO: 28 (XXXCAGXXAXCACXX-ACCAGCCCAX) wherein Z is 23;
y) SEQ ID NO: 29 (XXCAGXXAXCACXXACCAGCC-CAXC) wherein Z is 23;
z) SEQ ID NO: 30 (CAGXXAXCACXXACCAGCC-CAXCXX) wherein Z is 23;
aa) SEQ ID NO: 31 (AGXXAXCACXXACCAGCC-CAXCXXC) wherein Z is 23;
bb) SEQ ID NO: 50 (XXCAGXXAXCACXX-ACCAGCCCA) wherein Z is 21;
cc) SEQ ID NO: 51 (XXCAGXXAXCACXX-ACCAGCCCAX) wherein Z is 22;
dd) SEQ ID NO: 52 (XGXXAXXXXCAGXXAX-CACXXACC) wherein Z is 22;

ee) SEQ ID NO: 53 (GXXAXXXXCAGXXAXCACXX-ACCA) wherein Z is 22;

ff) SEQ ID NO: 54 (XCAGXXAXCACXXACCAGCC-CAXC) wherein Z is 22;

gg) SEQ ID NO: 55 (XXCAGXXAXCACXX-ACCAGCCC) wherein Z is 20;

hh) SEQ ID NO: 56 (CAGXXAXCACXXACCAGCC-CAXC) wherein Z is 21;

ii) SEQ ID NO: 57 (XXCAGXXAXCACXXACCAGCC) wherein Z is 19;

jj) SEQ ID NO: 58 (AGXXAXCACXXACCAGCC-CAXC) wherein Z is 20;

kk) SEQ ID NO: 59 (AXXXXCAGXXAXCACXX-ACCA) wherein Z is 19;

ll) SEQ ID NO: 60 (XXCAGXXAXCACXXACCAGC) wherein Z is 18;

mm) SEQ ID NO: 61 (XXAXXXXCAGXXAXCACXX-ACCA) wherein Z is 21;

nn) SEQ ID NO: 62 (XAXXXXCAGXXAXCACXX-ACCA) wherein Z is 20;

oo) SEQ ID NO: 63 (GXXAXCACXXACCAGCC-CAXC) wherein Z is 19;

pp) SEQ ID NO: 64 (XXXXCAGXXAXCACXXACCA) wherein Z is 18; and qq) SEQ ID NO: 65 (XXAXCACXXACCAGCCCAXC) wherein Z is 18;

and wherein X is independently selected from uracil (U) or thymine (T).

In some embodiments, the antisense oligomer is a compound of formula (VII):

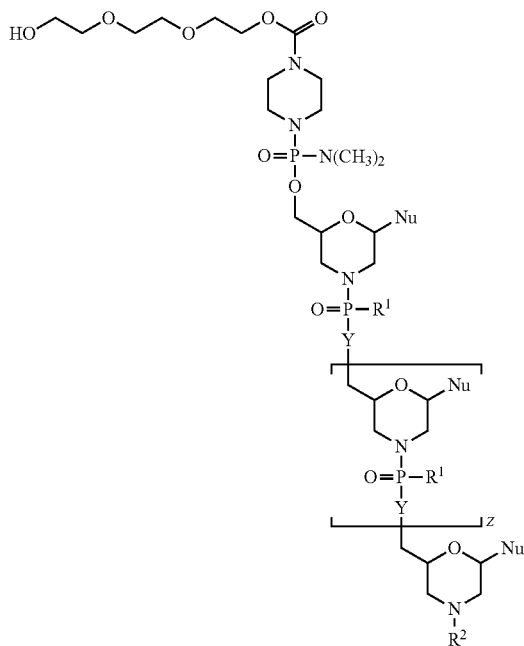

or a pharmaceutically acceptable salt thereof, where:
each Nu is a nucleobase which taken together form a targeting sequence; and
Z is an integer from 10 to 38;
each Y is O;

each $R^1$ is independently selected from:

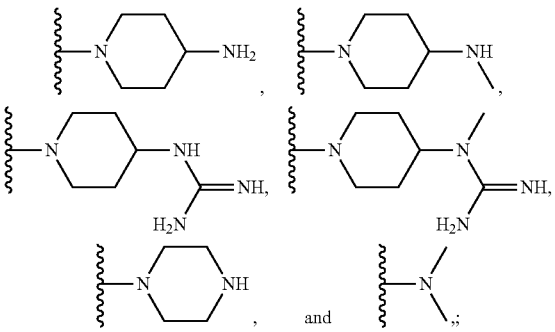

$R^2$ is selected from H, acyl, trityl, 4-methoxytrityl, $C_1$-$C_6$ alkyl, —C(=NH)NH$_2$, and —C(O)—$R^{23}$.

In various embodiments, the targeting sequence is complementary to or spans at least a portion of a splice junction region within intron 1/exon 2 (e.g., SEQ ID NO: 6) or exon 2/intron 2 (e.g., SEQ ID NO: 7, or SEQ ID NO: 8) of the human myostatin pre-mRNA. In some embodiments, the targeting sequence is complementary to 12 or more contiguous nucleotides in a target region spanning an 5 intron/exon junction of human myostatin pre-mRNA, said junction selected from intron 1/exon 2 and exon 2/intron 2. In various embodiments, the contiguous nucleotides include the splice intron/exon junction.

In various embodiments, the targeting sequence of compound (VII) comprises a sequence selected from SEQ ID NOS: 1-5, 10-31, or 50-65, is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T). In some embodiments, X is uniformly U or uniformly T.

In some embodiments, the targeting sequence of formula (VII) is selected from:

a) SEQ ID NO: 1 (CCAGCC-CAXCXXCXCCXGGXCCXGG) wherein Z is 23;

b) SEQ ID NO: 2 (CACXXACCAGCC-CAXCXXCXCCXGG) wherein Z is 23;

c) SEQ ID NO: 3 (CCAXCCACXXGCAXX-AGAAAAXCAGC) wherein Z is 24;

d) SEQ ID NO: 4 (GCAXXAGAAAAXCAGCXAX-AAAXG) wherein Z is 22;

e) SEQ ID NO: 5 (CCACXXGCAXXAGAAAAX-CAGC) wherein Z is 20;

f) SEQ ID NO: 10 (CXXGCAXXAGAAAAX-CAGCXAXAAA) wherein Z is 23;

g) SEQ ID NO: 11 (CACXXGCAXXAGAAAAX-CAGCXAXA) wherein Z is 23;

h) SEQ ID NO: 12 (CCACXXGCAXXAGAAAAX-CAGCXAX) wherein Z is 23;

i) SEQ ID NO: 13 (XCCACXXGCAXXAGAAAAX-CAGCXA) wherein Z is 23;

j) SEQ ID NO: 14 (AXCCACXXGCAXXAGAAAAX-CAGCX) wherein Z is 23;

k) SEQ ID NO: 15 (CAXCCACXXGCAXX-AGAAAAXCAGC) wherein Z is 23;

l) SEQ ID NO: 16 (XXAXXXXCAGXXAXCACXX-ACCAGC) wherein Z is 23;

m) SEQ ID NO: 17 (XXXXCAGXXAXCACXX-ACCAGCCCA) wherein Z is 23;

n) SEQ ID NO: 18 (XCAGXXAXCACXXACCAGCC-CAXCX) wherein Z is 23;
o) SEQ ID NO: 19 (GXXAXCACXXACCAGCC-CAXCXXCX) wherein Z is 23;
p) SEQ ID NO: 20 (AXCACXXACCAGCC-CAXCXXCXCCX) wherein Z is 23;
q) SEQ ID NO: 21 (ACXXACCAGCC-CAXCXXCXCCXGGX) wherein Z is 23;
r) SEQ ID NO: 22 (XACCAGCC-CAXCXXCXCCXGGXCCX) wherein Z is 23;
s) SEQ ID NO: 23 (AXGXXAXXXXCAGXXAX-CACXXACC) wherein Z is 23;
t) SEQ ID NO: 24 (XGXXAXXXXCAGXXAXCACXX-ACCA) wherein Z is 23;
u) SEQ ID NO: 25 (GXXAXXXXCAGXXAXCACXX-ACCAG) wherein Z is 23;
v) SEQ ID NO: 26 (XAXXXXCAGXXAXCACXX-ACCAGCC) wherein Z is 23;
w) SEQ ID NO: 27 (AXXXXCAGXXAXCACXX-ACCAGCCC) wherein Z is 23;
x) SEQ ID NO: 28 (XXXCAGXXAXCACXX-ACCAGCCCAX) wherein Z is 23;
y) SEQ ID NO: 29 (XXCAGXXAXCACXXACCAGCC-CAXC) wherein Z is 23;
z) SEQ ID NO: 30 (CAGXXAXCACXXACCAGCC-CAXCXX) wherein Z is 23;
aa) SEQ ID NO: 31 (AGXXAXCACXXACCAGCC-CAXCXXC) wherein Z is 23;
bb) SEQ ID NO: 50 (XXCAGXXAXCACXX-ACCAGCCCA) wherein Z is 21;
cc) SEQ ID NO: 51 (XXCAGXXAXCACXX-ACCAGCCCAX) wherein Z is 22;
dd) SEQ ID NO: 52 (XGXXAXXXXCAGXXAX-CACXXACC) wherein Z is 22;
ee) SEQ ID NO: 53 (GXXAXXXXCAGXXAXCACXX-ACCA) wherein Z is 22;
ff) SEQ ID NO: 54 (XCAGXXAXCACXXACCAGCC-CAXC) wherein Z is 22;
gg) SEQ ID NO: 55 (XXCAGXXAXCACXX-ACCAGCCC) wherein Z is 20;
hh) SEQ ID NO: 56 (CAGXXAXCACXXACCAGCC-CAXC) wherein Z is 21;
ii) SEQ ID NO: 57 (XXCAGXXAXCACXXACCAGCC) wherein Z is 19;
jj) SEQ ID NO: 58 (AGXXAXCACXXACCAGCC-CAXC) wherein Z is 20;
kk) SEQ ID NO: 59 (AXXXXCAGXXAXCACXX-ACCA) wherein Z is 19;
ll) SEQ ID NO: 60 (XXCAGXXAXCACXXACCAGC) wherein Z is 18;
mm) SEQ ID NO: 61 (XXAXXXXCAGXXAXCACXX-ACCA) wherein Z is 21;
nn) SEQ ID NO: 62 (XAXXXXCAGXXAXCACXX-ACCA) wherein Z is 20;
oo) SEQ ID NO: 63 (GXXAXCACXXACCAGCC-CAXC) wherein Z is 19;
pp) SEQ ID NO: 64 (XXXXCAGXXAXCACXXACCA) wherein Z is 18; and
qq) SEQ ID NO: 65 (XXAXCACXXACCAGCCCAXC) wherein Z is 18;
and wherein X is independently selected from uracil (U) or thymine (T).

In various embodiments, Y is O, $R^2$ is selected from H or G, $R^3$ is selected from an electron pair or H. In some embodiments, $R^2$ is G, wherein the CPP is a sequence selected from SEQ ID NOS: 32-47. In certain embodiments, $R^2$ is H.

In certain embodiments, the antisense oligomer is a compound of formula (VIII):

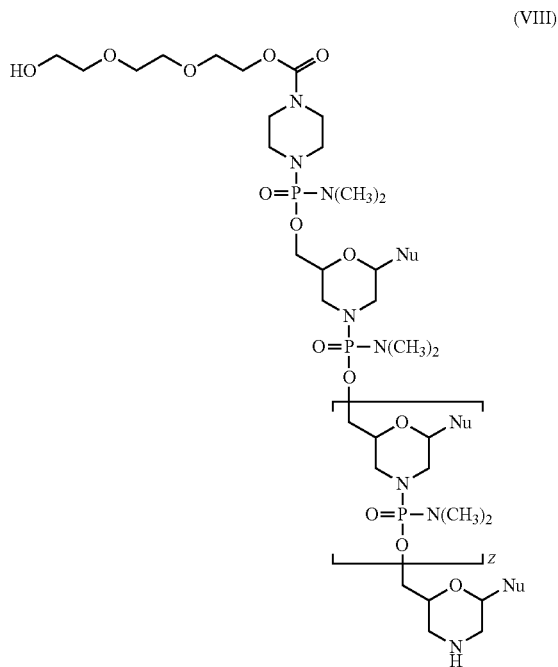

(VIII)

or a pharmaceutically acceptable salt thereof, where:
each Nu is a nucleobase which taken together form a targeting sequence; and
Z is an integer from 10 to 38.

In various embodiments, the targeting sequence is complementary to or spans at least a portion of a splice junction region within intron 1/exon 2 (e.g., SEQ ID NO: 6) or exon 2/intron 2 (e.g., SEQ ID NO: 7, or SEQ ID NO: 8) of the human myostatin pre-mRNA. In some embodiments, the targeting sequence is complementary to 12 or more contiguous nucleotides in a target region spanning an intron/exon junction of human myostatin pre-mRNA, said junction selected from intron 1/exon 2 and exon 2/intron 2. In various embodiments, the contiguous nucleotides include the splice intron/exon junction.

In various embodiments, the targeting sequence of compound (VIII) comprises a sequence selected from SEQ ID NOS: 1-5, 10-31, or 50-65, is selected from SEQ ID NOS: 1-5, 10-31, or 50-65, is a fragment of at least 12 contiguous nucleotides of a targeting sequence selected from SEQ ID NOS: 1-5, 10-31, or 50-65, or is a variant having at least 90% sequence identity to a targeting sequence selected from SEQ ID NOS: 1-5, 10-31, or 50-65, and wherein X is independently selected from uracil (U) or thymine (T). In some embodiments, X is uniformly U or uniformly T.

In some embodiments, the targeting sequence of compound (VIII) is selected from:
a) SEQ ID NO: 1 (CCAGCC-CAXCXXCXCCXGGXCCXGG) wherein Z is 23;
b) SEQ ID NO: 2 (CACXXACCAGCC-CAXCXXCXCCXGG) wherein Z is 23;
c) SEQ ID NO: 3 (CCAXCCACXXGCAXX-AGAAAAXCAGC) wherein Z is 24;
d) SEQ ID NO: 4 (GCAXXAGAAAAXCAGCXAX-AAAXG) wherein Z is 22;

e) SEQ ID NO: 5 (CCACXXGCAXXAGAAAAX-CAGC) wherein Z is 20;
f) SEQ ID NO: 10 (CXXGCAXXAGAAAAX-CAGCXAXAAA) wherein Z is 23;
g) SEQ ID NO: 11 (CACXXGCAXXAGAAAAX-CAGCXAXA) wherein Z is 23;
h) SEQ ID NO: 12 (CCACXXGCAXXAGAAAAX-CAGCXAX) wherein Z is 23;
i) SEQ ID NO: 13 (XCCACXXGCAXXAGAAAAX-CAGCXA) wherein Z is 23;
j) SEQ ID NO: 14 (AXCCACXXGCAXXAGAAAAX-CAGCX) wherein Z is 23;
k) SEQ ID NO: 15 (CAXCCACXXGCAXX-AGAAAAXCAGC) wherein Z is 23;
l) SEQ ID NO: 16 (XXAXXXXCAGXXAXCACXX-ACCAGC) wherein Z is 23;
m) SEQ ID NO: 17 (XXXXCAGXXAXCACXX-ACCAGCCCA) wherein Z is 23;
n) SEQ ID NO: 18 (XCAGXXAXCACXXACCAGCC-CAXCX) wherein Z is 23;
o) SEQ ID NO: 19 (GXXAXCACXXACCAGCC-CAXCXXCX) wherein Z is 23;
p) SEQ ID NO: 20 (AXCACXXACCAGCC-CAXCXXCXCCX) wherein Z is 23;
q) SEQ ID NO: 21 (ACXXACCAGCC-CAXCXXCXCCXGGX) wherein Z is 23;
r) SEQ ID NO: 22 (XACCAGCC-CAXCXXCXCCXGGXCCX) wherein Z is 23;
s) SEQ ID NO: 23 (AXGXXAXXXXCAGXXAX-CACXXACC) wherein Z is 23;
t) SEQ ID NO: 24 (XGXXAXXXXCAGXXAXCACXX-ACCA) wherein Z is 23;
u) SEQ ID NO: 25 (GXXAXXXXCAGXXAXCACXX-ACCAG) wherein Z is 23;
v) SEQ ID NO: 26 (XAXXXXCAGXXAXCACXX-ACCAGCC) wherein Z is 23;
w) SEQ ID NO: 27 (AXXXXCAGXXAXCACXX-ACCAGCCC) wherein Z is 23;
x) SEQ ID NO: 28 (XXXCAGXXAXCACXX-ACCAGCCCAX) wherein Z is 23;
y) SEQ ID NO: 29 (XXCAGXXAXCACXXACCAGCC-CAXC) wherein Z is 23;
z) SEQ ID NO: 30 (CAGXXAXCACXXACCAGCC-CAXCXX) wherein Z is 23;
aa) SEQ ID NO: 31 (AGXXAXCACXXACCAGCC-CAXCXXC) wherein Z is 23;
bb) SEQ ID NO: 50 (XXCAGXXAXCACXX-ACCAGCCCA) wherein Z is 21;
cc) SEQ ID NO: 51 (XXCAGXXAXCACXX-ACCAGCCCAX) wherein Z is 22;
dd) SEQ ID NO: 52 (XGXXAXXXXCAGXXAX-CACXXACC) wherein Z is 22;
ee) SEQ ID NO: 53 (GXXAXXXXCAGXXAXCACXX-ACCA) wherein Z is 22;
ff) SEQ ID NO: 54 (XCAGXXAXCACXXACCAGCC-CAXC) wherein Z is 22;
gg) SEQ ID NO: 55 (XXCAGXXAXCACXX-ACCAGCCC) wherein Z is 20;
hh) SEQ ID NO: 56 (CAGXXAXCACXXACCAGCC-CAXC) wherein Z is 21;
ii) SEQ ID NO: 57 (XXCAGXXAXCACXXACCAGCC) wherein Z is 19;
jj) SEQ ID NO: 58 (AGXXAXCACXXACCAGCC-CAXC) wherein Z is 20;
kk) SEQ ID NO: 59 (AXXXXCAGXXAXCACXX-ACCA) wherein Z is 19;
ll) SEQ ID NO: 60 (XXCAGXXAXCACXXACCAGC) wherein Z is 18;
mm) SEQ ID NO: 61 (XXAXXXXCAGXXAXCACXX-ACCA) wherein Z is 21;
nn) SEQ ID NO: 62 (XAXXXXCAGXXAXCACXX-ACCA) wherein Z is 20;
oo) SEQ ID NO: 63 (GXXAXCACXXACCAGCC-CAXC) wherein Z is 19;
pp) SEQ ID NO: 64 (XXXXCAGXXAXCACXXACCA) wherein Z is 18; and
qq) SEQ ID NO: 65 (XXAXCACXXACCAGCCCAXC) wherein Z is 18;
and wherein X is independently selected from uracil (U) or thymine (T).

In some embodiments, each Nu of the antisense oligomers of the disclosure, including compounds of formula (I), (IV), (V), (VI), (VII) and (VIII), is independently selected from adenine, guanine, thymine, uracil, cytosine, hypoxanthine (inosine), 2,6-diaminopurine, 5-methyl cytosine, C5-propynyl-modified pyrimidines, and 10-(9-(aminoethoxy)phenoxazinyl). In some embodiments, the targeting sequence of the antisense oligomers of the disclosure, including compounds of formula (I), (IV), (V), (VI), (VII) and (VIII), comprises a sequence selected from SEQ ID NOS: 1-5, 10-31, or 50-65, is selected from SEQ ID NOS: 1-5, 10-31, or 50-65, is a fragment of at least 12 contiguous nucleotides of a sequence selected from SEQ ID NOS: 1-5, 10-31, or 50-65, or is a variant having at least 90% sequence identity to a sequence selected from SEQ ID NOS: 1-5, 10-31, or 50-65, and wherein X is independently selected from uracil (U) or thymine (T). In some embodiments, X is uniformly U or uniformly T.

In some embodiments of any of the methods or compositions described herein, Z is an integer from 8 to 28, from 15 to 38, 15 to 28, 8 to 25, from 15 to 25, from 10 to 38, from 10 to 25, from 12 to 38, from 12 to 25, from 14 to 38, or from 14 to 25. In some embodiments of any of the methods or compositions described herein, Z is 12, 13, 14, 15, 16, 17, 18, 19, 20, 21, 22, 23, 24, 25, 26, 27, 28, 29, 30, 31, 32, 33, 34, 35, 36, 37, or 38. In some embodiments of any of the methods or compositions described herein, Z is 12, 13, 14, 15, 16, 17, 18, 19, 20, 21, 22, 23, 24, 25, 26, 27, or 28. In some embodiments of any of the methods or compositions described herein, Z is 15, 16, 17, 18, 19, 20, 21, 22, 23, 24, or 25.

In some embodiments, each Z of the modified antisense oligomers of the disclosure, including compounds of formulas (I), (IV), (V), (VI), (VII), and (VIII), is an integer from 8 to 28.

In some embodiments, each Z of the modified antisense oligomers of the disclosure, including compounds of formulas (I), (IV), (V), (VI), (VII), and (VIII), is an integer from 15 to 38.

In some embodiments, each Z of the modified antisense oligomers of the disclosure, including compounds of formulas (I), (IV), (V), (VI), (VII), and (VIII), is an integer from 15 to 28.

In some embodiments, each Z of the modified antisense oligomers of the disclosure, including compounds of formulas (I), (IV), (V), (VI), (VII), and (VIII), is an integer from 8 to 25.

In some embodiments, each Z of the modified antisense oligomers of the disclosure, including compounds of formulas (I), (IV), (V), (VI), (VII), and (VIII), is an integer from 15 to 25.

In some embodiments, each Z of the modified antisense oligomers of the disclosure, including compounds of formulas (I), (IV), (V), (VI), (VII), and (VIII), is an integer from 10 to 38.

In some embodiments, each Z of the modified antisense oligomers of the disclosure, including compounds of formulas (I), (IV), (V), (VI), (VII), and (VIII), is an integer from 10 to 25.

In some embodiments, each Z of the modified antisense oligomers of the disclosure, including compounds of formulas (I), (IV), (V), (VI), (VII), and (VIII), is an integer from 12 to 38.

In some embodiments, each Z of the modified antisense oligomers of the disclosure, including compounds of formulas (I), (IV), (V), (VI), (VII), and (VIII), is an integer from 12 to 25.

In some embodiments, each Z of the modified antisense oligomers of the disclosure, including compounds of formulas (I), (IV), (V), (VI), (VII), and (VIII), is an integer from 14 to 38.

In some embodiments, each Z of the modified antisense oligomers of the disclosure, including compounds of formulas (I), (IV), (V), (VI), (VII), and (VIII), is an integer from 14 to 25.

In some embodiments, each Z of the modified antisense oligomers of the disclosure, including compounds of formulas (I), (IV), (V), (VI), (VII), and (VIII), is 12, 13, 14, 15, 16, 17, 18, 19, 20, 21, 22, 23, 24, 25, 26, 27, 28, 29, 30, 31, 32, 33, 34, 35, 36, 37, or 38.

In some embodiments, each Z of the modified antisense oligomers of the disclosure, including compounds of formulas (I), (IV), (V), (VI), (VII), and (VIII), is 12, 13, 14, 15, 16, 17, 18, 19, 20, 21, 22, 23, 24, 25, 26, 27, or 28.

In some embodiments, each Z of the modified antisense oligomers of the disclosure, including compounds of formulas (I), (IV), (V), (VI), (VII), and (VIII), is 15, 16, 17, 18, 19, 20, 21, 22, 23, 24, or 25.

In some embodiments of any of the compounds described herein (e.g., compounds having any one of the formulas: (I), (IV), (V), (VI), (VII), or (VIII)), the targeting sequence comprises at least 11 (e.g., at least 12, 13, 14, 15, 16, 17, 18, 19, 20, 21, 22, 23, 24 or 25) contiguous bases of any one of SEQ ID NOS: 1-5, 10-31, or 50-65, wherein X is independently selected from uracil (U) or thymine (T). In some embodiments, X is uniformly U or uniformly T.

Additional antisense oligomers/chemistries that can be used in accordance with the present disclosure include those described in the following patents and patent publications, which are hereby incorporated by reference in their entirety: PCT Publication Nos. WO 2007/002390; WO 2010/120820; and WO 2010/148249; U.S. Pat. No. 7,838,657; and U.S. Patent Application No. 2011/0269820.

C. The Preparation of Morpholino Subunits and Phosphoroamidate Internucleoside Linkers Morpholino monomer subunits, the modified internucleoside linkages, and oligomers comprising the same can be prepared as described, for example, in U.S. Pat. Nos. 5,185,444, and 7,943,762, which are hereby incorporated by reference in their entirety. The morpholino subunits can be prepared according to the following general Reaction Scheme I.

Reaction Scheme 1: Preparation, Protection, and Activation of Morpholino Subunit.

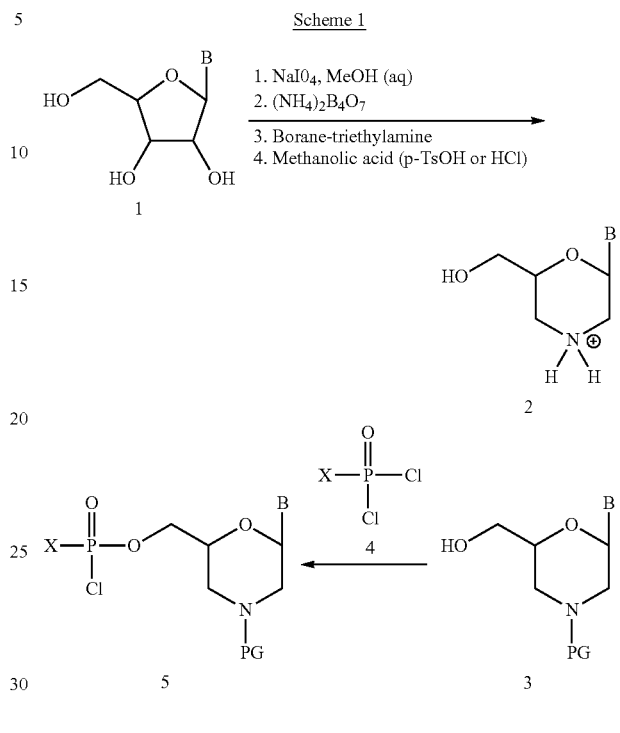

Referring to Reaction Scheme 1, where B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in U.S. Pat. No. 8,076,476, which is hereby incorporated by reference in its entirety.

Reaction of compound 3 with the activated phosphorous compound 4, results in morpholino subunits having the desired linkage moiety compound 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. Nos. 5,185,444, 7,943,762, and 8,779,128, which are hereby incorporated by reference in its entirety.

Compounds of structure 5 can be used in solid-phase automated oligomer synthesis for preparation of oligomers comprising the internucleoside linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$. An exemplary method is demonstrated in FIG. 1A. Once supported, the protecting group (e.g., trityl) is removed and the free amine is reacted with an activated phosphorous moiety of a second compound of structure 5. This sequence is repeated until the desired length of oligo is obtained. The protecting group in the terminal 5' end may either be removed or left on if a 5'-modification is desired. The oligo can be removed from the solid support using any number of methods, for example treatment with DTT followed by ammonium hydroxide.

The preparation of modified morpholino subunits and morpholino-based oligomers are described in more detail in the Examples. The morpholino-based oligomers containing any number of modified linkages may be prepared using methods described herein, methods known in the art and/or described by reference herein. Also described in the examples are global modifications of morpholino-based oligomers prepared as previously described (see e.g., PCT Publication No. WO 2008/036127, which is hereby incorporated by reference in its entirety).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999), which is hereby incorporated by reference in its entirety. It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

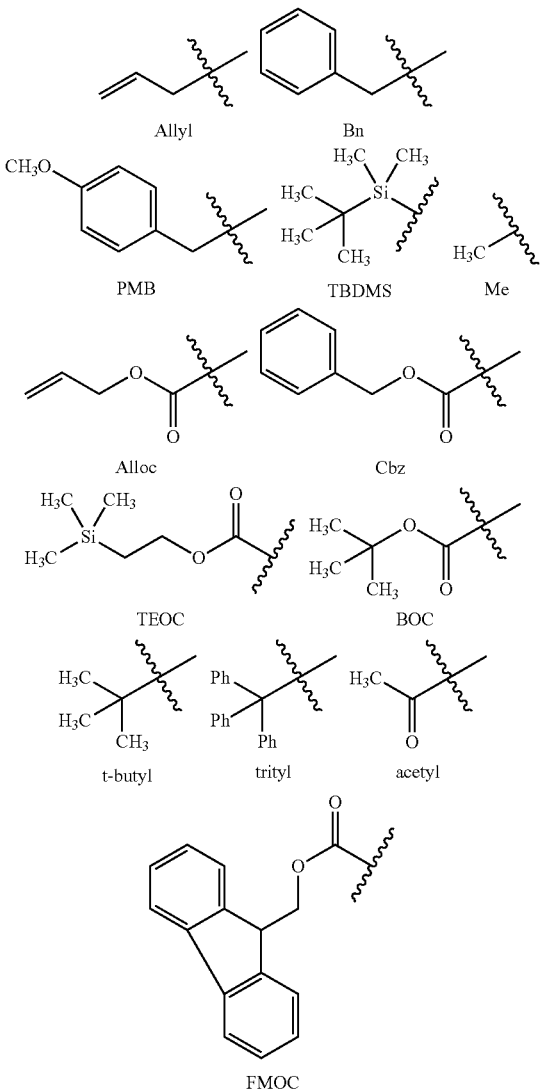

Unless otherwise noted, all chemicals were obtained from Sigma-Aldrich-Fluka (St. Louis, Mo.). Benzoyl adenosine, benzoyl cytidine, and phenylacetyl guanosine were obtained from Carbosynth Limited (Berkshire, UK).

Synthesis of PMO, PMOplus, PPMO, and PMO-X containing further linkage modifications as described herein was done using methods known in the art and described in pending U.S. patent application Ser. Nos. 12/271,036 and 12/271,040 and PCT Publication No. WO 2009/064471, which is hereby incorporated by reference in its entirety.

PMO with a 3' trityl modification are synthesized essentially as described in PCT Publication No. WO 2009/064, 471, with the exception that the detritylation step is omitted.

D. Cell-Penetrating Peptides

Figure 1B:
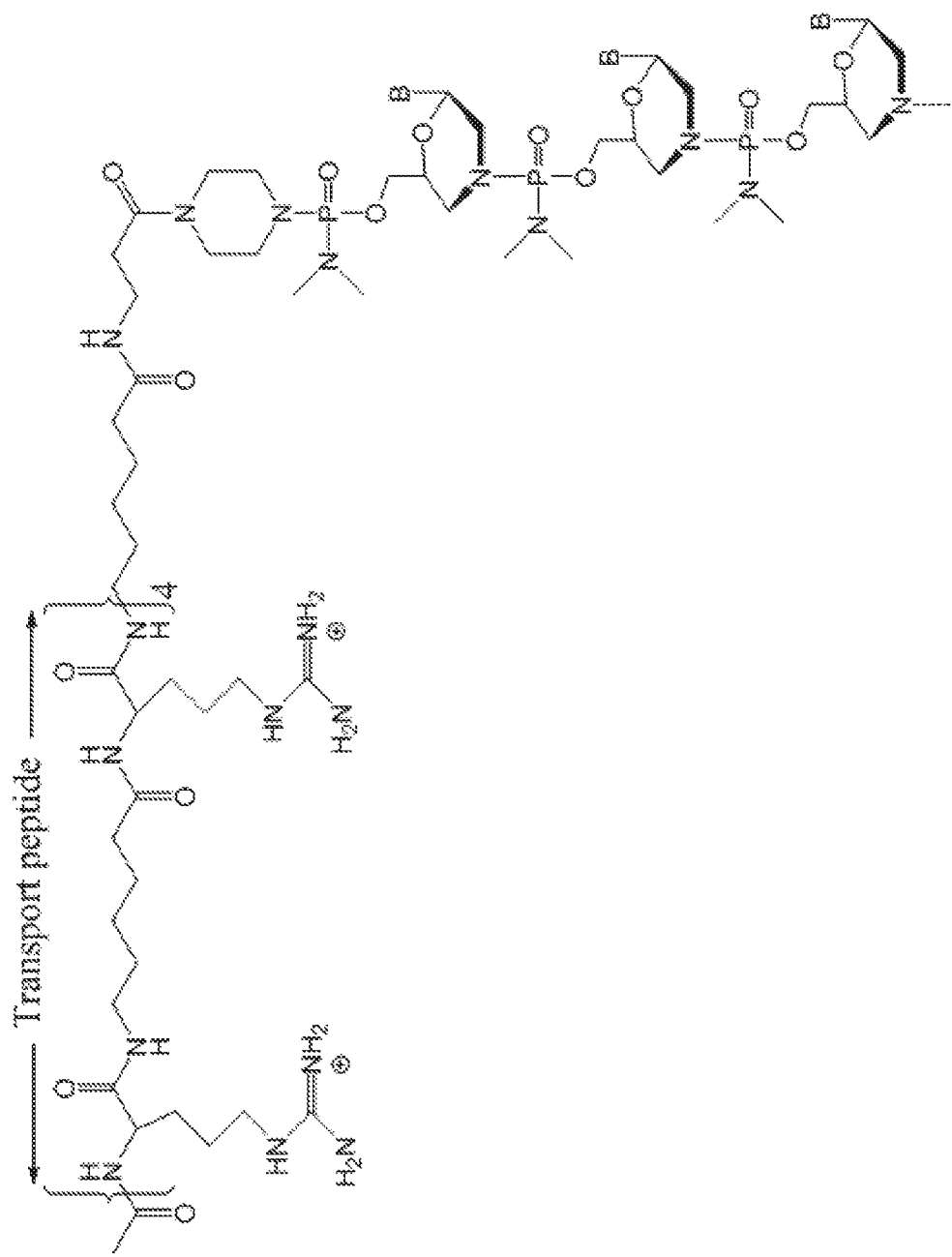
FIGS. 1B and 1C illustrates an antisense oligonucleotide covalently bonded to a cell penetrating peptide (CPP).
Figure 1C:
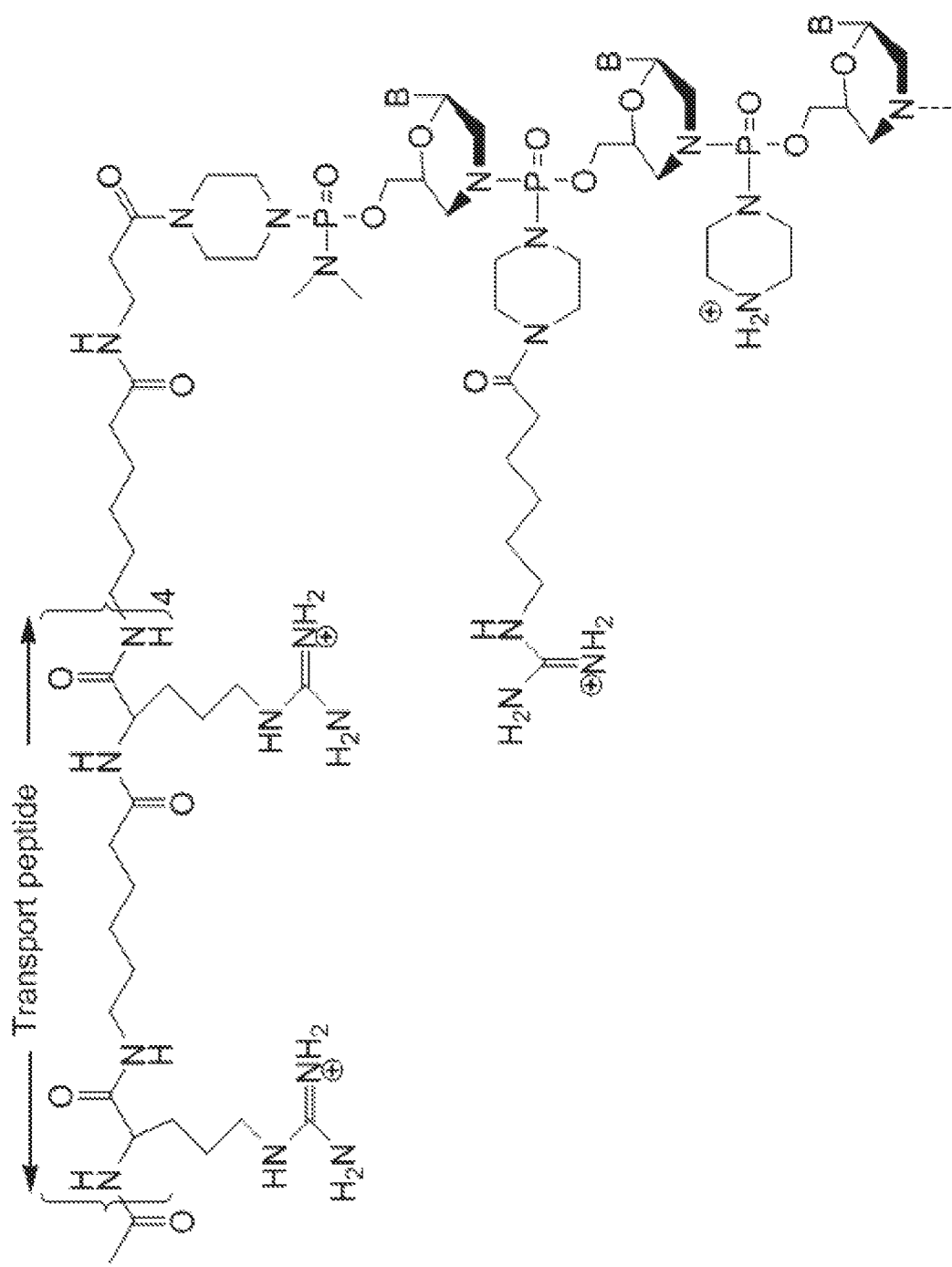
Figure 1E:
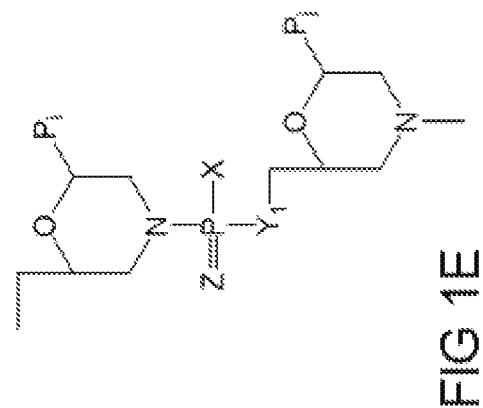
FIGS. 1D, 1E, 1F and 1G illustrate a repeating subunit segment of exemplary morpholino oligonucleotides, designated D through G.
Figure 1G:
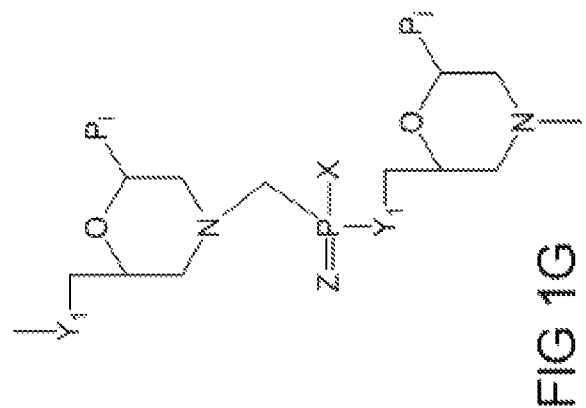
Figure 1D:
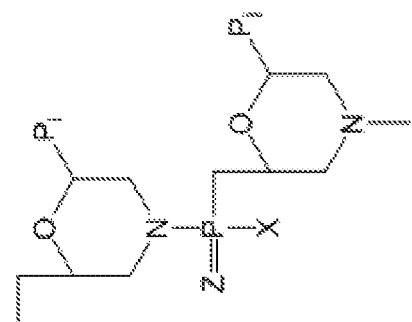
Figure 1F:
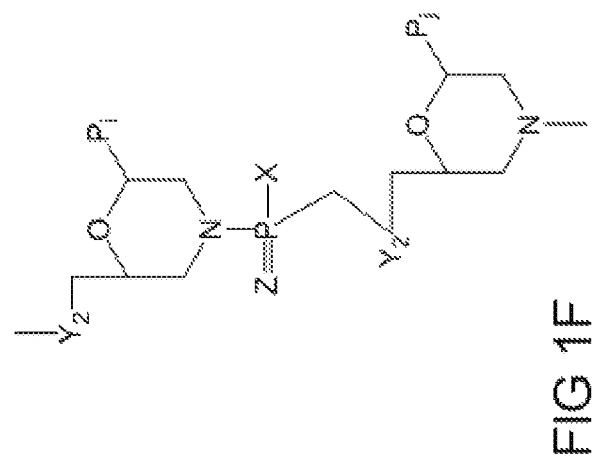

The antisense oligomer compounds of the disclosure may be covalently bonded to a peptide, also referred to herein as a cell penetrating peptide (CPP). In certain preferred embodiments, the peptide is an arginine-rich peptide transport moiety effective to enhance transport of the compound into cells. The transport moiety is preferably attached to a terminus of the oligomer, as shown, for example, in FIGS. 1B and 1C. The peptides have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration. In one embodiment, the cell-penetrating peptide may be an arginine-rich peptide transporter. In another embodiment, the cell-penetrating peptide may be Penetratin or the Tat peptide. These peptides are well known in the art and are disclosed, for example, in US Publication No. 2010-0016215 A1, which is hereby incorporated by reference in its entirety. One approach to conjugation of peptides to antisense oligonucleotides of the disclosure can be found in PCT publication WO2012/150960, which is hereby incorporated by reference in its entirety. Some embodiments of a peptide-conjugated oligonucleotide of the present disclosure utilize glycine as the linker between the CPP and the antisense oligonucleotide. For example, a peptide-conjugated PMO of the disclosure consists of $R_6$-G-PMO.

The transport moieties as described above have been shown to greatly enhance cell entry of attached oligomers, relative to uptake of the oligomer in the absence of the attached transport moiety. Uptake is preferably enhanced at least ten fold, and more preferably twenty fold, relative to the unconjugated compound.

The use of arginine-rich peptide transporters (i.e., cell-penetrating peptides) are particularly useful in practicing the present disclosure. Certain peptide transporters have been shown to be highly effective at delivery of antisense compounds into primary cells including muscle cells (Marshall, Oda et al. 2007; Jearawiriyapaisarn, Moulton et al. 2008; Wu, Moulton et al. 2008, which are hereby incorporated by reference in their entirety). Furthermore, compared to other known peptide transporters such as Penetratin and the Tat peptide, the peptide transporters described herein, when covalently bonded to an antisense PMO, demonstrate an enhanced ability to alter splicing of several gene transcripts (Marshall, Oda et al. 2007, which is hereby incorporated by reference in its entirety).

Exemplary peptide transporters, excluding linkers are given below in Table 3.

TABLE 3

Exemplary peptide transporters

| NAME (DESIGNATION) | SEQUENCE | SEQ ID NO[A] |
|---|---|---|
| rTAT | RRRQRRKKR | 32 |
| Tat | RKKRRQRRR | 33 |
| $R_9F_2$ | RRRRRRRRRFF | 34 |
| $R_5F_2R_4$ | RRRRRFFRRRR | 35 |
| $R_4$ | RRRR | 36 |
| $R_5$ | RRRRR | 37 |
| $R_6$ | RRRRRR | 38 |
| $R_7$ | RRRRRRR | 39 |
| $R_8$ | RRRRRRRR | 40 |
| $R_9$ | RRRRRRRRR | 41 |
| $(RX)_8$ | RAhxRAhxRAhxRAhxRAhxRAhxRAhxRAhx | 42 |
| $(RAhxR)_4$; (P007) | RAhxRRAhxRRAhxRRAhxR | 43 |
| $(RAhxR)_5$; (CP04057) | RAhxRRAhxRRAhxRRAhxRRAhxR | 44 |
| $(RAhxRRBR)_2$(CP06062) | RAhxRRBRRAhxRRBR | 45 |
| $(RAR)_4F_2$ | RARRARRARRARFF | 46 |
| $(RGR)_4F_2$ | RGRRGRRGRRGRFF | 47 |

[A]Sequences assigned to SEQ ID NOS do not include the linkage portion (e.g., C (cys), G (gly), P (pro), Ahx, B, AhxB where Ahx and B refer to 6-aminohexanoic acid and beta-alanine, respectively).

In various embodiments, G, (as recited in formulas I, IV, and V), is a cell penetrating peptide ("CPP") and linker moiety selected from:
—C(O)(CH$_2$)$_5$NH—CPP,    —C(O)(CH$_2$)$_2$NH—CPP, —C(O)(CH$_2$)$_2$NHC(O)(CH$_2$)$_5$NH—CPP,
and —C(O)CH$_2$NH—CPP, or G is of the formula:

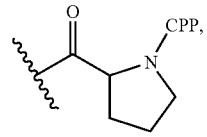

wherein the CPP is attached to the linker moiety by an amide bond at the CPP carboxy terminus.

In some embodiments, the CPP is selected from SEQ ID NOS: 32-47.

IV. Formulations

The compounds of the disclosure may also be admixed, encapsulated, covalently bonded to, or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, which are hereby incorporated by reference in their entirety.

The antisense compounds of the disclosure encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the disclosure, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the disclosure are prepared as SATE [(S-acetyl-2-thioethyl) phosphate] derivatives according to the methods disclosed in PCT Publication No. WO 1993/24510 to Gosselin et al., published Dec. 9, 1993 or in PCT Publication No. WO 1994/26764 and U.S. Pat. No. 5,770,713 to Imbach et al., which are hereby incorporated by reference in their entirety The term "pharmaceutically acceptable salts" refers to physiologically and pharmaceutically acceptable salts of the compounds of the disclosure: i.e., salts that retain the desired biological activity of the parent compound and do not impart undesired toxicological effects thereto. For oligomers, examples of pharmaceutically acceptable salts and their uses are further described in U.S. Pat. No. 6,287,860, which is hereby incorporated by reference in its entirety.

The present disclosure also includes pharmaceutical compositions and formulations which include the antisense compounds of the disclosure. The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, gel capsules, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present disclosure include, but are not limited to, solutions, emulsions, foams and liposome-containing formulations. The pharmaceutical compositions and formulations of the present disclosure may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present disclosure. Emulsions and their uses are well known in the art and are further described in U.S. Pat. No. 6,287,860, which is hereby incorporated by reference in its entirety.

Formulations of the present disclosure include liposomal formulations. As used in the present disclosure, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic oligomers, such as a polyethylene glycol (PEG) moiety. Liposomes and their uses are further described in U.S. Pat. No. 6,287,860, which is hereby incorporated by reference in its entirety.

The pharmaceutical formulations and compositions of the present disclosure may also include surfactants. The use of surfactants in drug products, formulations and in emulsions is well known in the art. Surfactants and their uses are further described in U.S. Pat. No. 6,287,860, which is hereby incorporated by reference in its entirety.

In some embodiments, the present disclosure employs various penetration enhancers to effect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is hereby incorporated by reference in its entirety.

One of skill in the art will recognize that formulations are routinely designed according to their intended use, i.e. route of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860, which is hereby incorporated by reference in its entirety. Topical formulations are described in detail in U.S. patent application Ser. No. 09/315,298 filed on May 20, 1999, which is hereby incorporated by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860, which is hereby incorporated by reference in its entirety. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860, which is hereby incorporated by reference in its entirety. Oral formulations for oligomers and their preparation are described in detail in U.S. patent application Ser. No. 09/108,673 (filed Jul. 1, 1998), Ser. No. 09/315,298 (filed May 20, 1999) and Ser. No. 10/071,822 (filed Feb. 8, 2002), which are hereby incorporated by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

In another related embodiment, compositions of the disclosure may contain one or more antisense compounds, particularly oligomers, targeted to a first nucleic acid and one or more additional antisense compounds targeted to a second nucleic acid target. Alternatively, compositions of the disclosure may contain two or more antisense compounds targeted to different regions of the same nucleic acid target. Numerous examples of antisense compounds are known in the art. Two or more combined compounds may be used together or sequentially.

V. Methods of Use

Various aspects relate to methods of increasing muscle mass in a subject. In further aspects, methods of treating or preventing the decrease of muscle mass in a subject is provided, where, a subject may be a healthy subject or a subject afflicted with a muscle decreasing disease, disorder, or condition. In further aspects, methods of treating muscular dystrophy or a related disorder are provided. In further aspects, methods of inhibiting the expression of genomic exon 2 of the myostatin gene are provided. In further aspects, methods of inhibiting the splicing of myostatin pre-mRNA sequences comprising a splice junction are provided. In further aspects, methods of inhibiting the splicing of at least one of intron 1 and intron 2 from exon 2 in a myostatin pre-mRNA transcript are provided. In further aspects, methods of inhibiting the expression of exon 2 in a mature mRNA myostatin transcript are provided. In further aspects, methods of inhibiting the expression of myostatin mRNA are provided. In further aspects, methods of modulating the expression of a myostatin protein are provided. In further aspects, methods of inhibiting the expression of a functional myostatin protein are provided.

In further aspects and embodiments, methods of treating an individual afflicted with or at risk for developing muscular dystrophy and related disorders are provided, comprising administering an effective amount of an antisense oligomer of the disclosure to the subject. In various embodiments, the antisense oligomer comprises a nucleotide sequence of sufficient length and complementarity to specifically hybridize to a splice junction region within the pre-mRNA transcript of the myostatin gene, where binding of the antisense oligomer to the region decreases the level of exon 2 containing myostatin mRNA in a cell and/or tissue of the subject. Exemplary antisense targeting sequences are shown in Table 2.

Also included are antisense oligomers for use in the preparation of a medicament for the treatment of muscular dystrophy and related disorders, comprising a nucleotide sequence of sufficient length and complementarity to specifically hybridize to a region within the pre-mRNA transcript of the myostatin gene, where binding of the antisense oligomer to the target region decreases the level of exon 2 myostatin mRNA.

In various aspects and embodiments comprising methods of treating muscular dystrophy and related disorders, and medicaments for the treatment of muscular dystrophy and related disorders, the antisense oligomer comprises 12 to 40 subunits, optionally having at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an intron/exon splice junction of human myostatin pre mRNA. In various embodiments, the contiguous nucleotides include the splice intron/exon junction. In further embodiments, the splice junctions may be selected from the splice junction at intron 1/exon 2 (e.g., SEQ ID NO: 6) or exon 2/intron 2 (e.g., SEQ ID NO: 7, or SEQ ID NO: 8). These may include 12 to 40 subunits that specifically hybridize to a target region spanning an intron/exon splice junction of human myostatin pre-mRNA. The splice junctions are optionally selected from splice junctions at the intersection of intron 1/exon 2 and exon 2/intron 2. In embodiments, the splice junction of intron 1/exon 2 is selected from the splice junction within SEQ ID NO: 6; the splice junction of exon 2/intron 2 is selected from the splice junction within SEQ ID NO: 7, or SEQ ID NO: 8.

These additional aspects and embodiments include antisense oligomers having a nucleotide analog subunit comprising a modified sugar moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

These additional aspects and embodiments include antisense oligomers having a nucleotide analog subunit comprising a modified internucleoside linkage. In various embodiments, the modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

These additional aspects and embodiments include antisense oligomers having a nucleotide analog subunit comprising at least one combination of a modified sugar moiety and a modified internucleoside linkage.

Various aspects relate to methods of decreasing expression of exon 2 myostatin mRNA transcript or decreasing the expression of functional myostatin protein in a cell, tissue, and/or subject, using the antisense oligomers as described herein. In some instances, exon-2 myostatin mRNA transcript or functional myostatin protein is decreased or reduced by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject (for example, a subject not having muscular dystrophy or a related disorder), a control composition without the antisense oligomer, the absence of treatment, and/or an earlier time-point. Also included are methods of decreasing the expression of exon 2 containing mRNA transcript or functional myostatin protein relative to the levels of a healthy control, for example, a subject not having muscular dystrophy or a related disorder.

Various aspects relate to methods of decreasing expression of a functional/active myostatin protein in a cell, tissue, and/or subject, as described herein. In certain instances, the level of functional/active myostatin protein is decreased by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject (for example, a subject having muscular dystrophy or a related disorder), a control composition without the antisense oligomer, the absence of treatment, and/or an earlier time-point. Also included are methods of decreasing the expression of functional/active myostatin protein relative to the levels of an affected control, for example, a subject having muscular dystrophy or a related disorder.

Various aspects relate to methods of inhibiting the progression of muscular dystrophy and related disorders in a subject using the antisense oligomers as described herein.

Various aspects relate to methods of reducing, or improving, as appropriate, one or more symptoms of muscular dystrophy and related disorders in a subject in need thereof. Particular examples include symptoms of progressive muscle weakness such as frequent falls, difficulty getting up from a lying or sitting position, trouble running and jumping, waddling gait, walking on the toes, large calf muscles, muscle pain and stiffness and learning disabilities.

Still further aspects relate to methods of increasing skeletal muscle mass in a subject. Still further aspects relate to methods of treating or preventing the decrease of muscle mass in a subject, in a healthy subject or a subject afflicted with a disease, disorder or condition. Still further aspects relate to methods of treating skeletal muscle mass deficiency in a subject afflicted with a disease, disorder, or condition. In various embodiments, blood or tissue levels of myostatin protein are measured in a patient prior to administration of an antisense oligomer described herein. An effective amount of an antisense oligomer herein is administered to the subject. Blood or tissue levels of myostatin protein are measured in the subject after a select time and administration of the antisense oligomer. Optionally, the dosage and/or dosing schedule of the antisense oligomer is adjusted according to the measurement, for example, to increase the dosage to ensure a therapeutic amount is present in the subject. A select time may include an amount of time after administration of an antisense oligomer described herein, to allow time for the antisense oligomer to be absorbed into the bloodstream and/or metabolized by the liver and other metabolic processes. In some embodiments, a select time may be about 1, 2, 3, 4, 5, 6, 7, 8, 9, 10, 11, 12, 15, 18, 20, 22, or 24 hours after administration of an antisense oligomer.

In some embodiments, a select time may be about 12, 18 or 24 hours after administration of an antisense oligomer. In other embodiments, a select time may be about 1, 2, 3, 4, 5, 6 or 7 days after administration of an antisense oligomer.

Antisense oligomers herein may be administered to subjects to treat (prophylactically or therapeutically) muscular dystrophy and related disorders. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced. Direct CNS delivery may be employed, for instance, intracerebral ventribular or intrathecal administration may be used as routes of administration.

In particular embodiments, the antisense oligomer(s) are administered to the subject by intravenous (IV) or subcutaneous (SC), i.e., they are administered or delivered intravenously into a vein or subcutaneously into the fat layer between the skin and muscle. Non-limiting examples of intravenous injection sites include a vein of the arm, hand, leg, or foot. Non-limiting examples of subcutaneous injections sites include the abdomen, thigh, lower back or upper arm. In exemplary embodiments, a PMO, PMO-X, or PPMO forms of the antisense oligomer is administered by IV or SC. In other embodiments, the antisense oligomer(s) are administered to the subject by intramuscular (IM), e.g., they are administered or delivered intramuscularly into the deltoid muscle of the arm, the vastus lateralis muscle of the leg, the ventrogluteal muscles of the hips, or dorsogluteal muscles of the buttocks.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, which are hereby incorporated by reference in their entirety.

The antisense oligomers described herein may also be delivered via an implantable device. Design of such a device is an art-recognized process, with, e.g., synthetic implant design described in, e.g., U.S. Pat. No. 6,969,400, which are hereby incorporated by reference in their entirety.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49 (2000), which is hereby incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The antisense oligomers of the present disclosure may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure where hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers of the disclosure. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in PCT Publication No. WO 1993/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules. Each such reference is hereby incorporated by reference in their entirety.

In one embodiment, the antisense oligomer is administered to a mammalian subject, e.g., human or domestic animal, exhibiting the symptoms of muscular dystrophy and related disorders, in a suitable pharmaceutical carrier. In one aspect of the method, the subject is a human subject, e.g., a patient diagnosed as having muscular dystrophy and related disorders. In one preferred embodiment, the antisense oligomer is contained in a pharmaceutically acceptable carrier, and is delivered orally. In another preferred embodiment, the oligomer is contained in a pharmaceutically acceptable carrier, and is delivered intravenously (i.v.).

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mRNA which does not comprise myostatin exon 2 in relation to a reference exon 2-containing myostatin mRNA as determined by standard techniques such as RT-PCR, Northern blotting, ELISA or Western blotting.

In some embodiments, the antisense oligomer is actively taken up by mammalian cells. In further embodiments, the antisense oligomer may be covalently bonded to a transport moiety (e.g., transport peptide or CPP) as described herein to facilitate such uptake.

VI. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 gg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, where the oligomer is administered in maintenance doses, ranging from 1-1000 mg oligomer per 70 kg of body weight for oral administration, or 0.5 mg to 1000 mg oligomer per 70 kg of body weight for i.v. administration, once or more daily, to once every 20 years.

While the present disclosure has been described with specificity in accordance with certain of its embodiments, the following examples serve only to illustrate the disclosure and are not intended to limit the same. Each of the references, patents, patent applications, GenBank accession numbers, and the like recited in the present application are hereby incorporated by reference in its entirety.

VII. Examples

Example 1

Design and Manufacture of Antisense Oligonucleotides

Figure 2A:
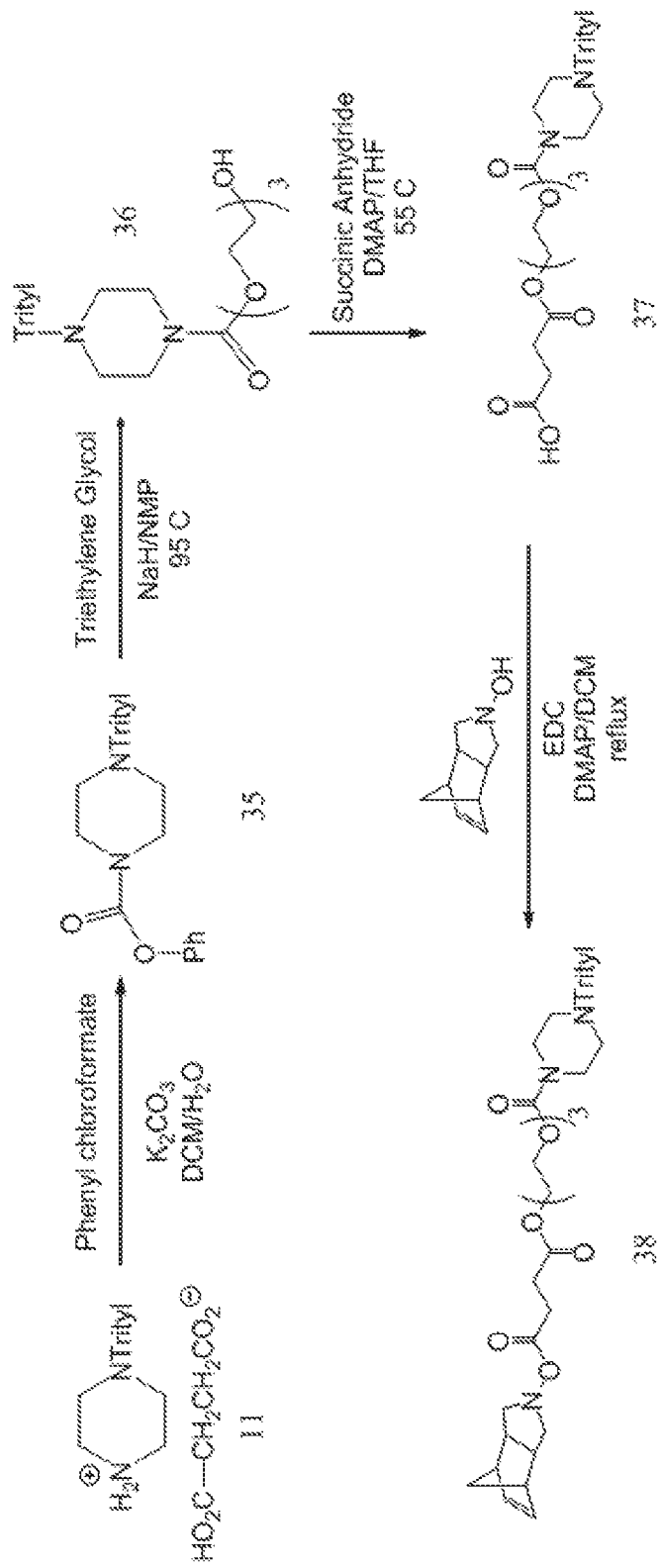
FIG. 2A illustrates preparation of trityl piperazine phenyl carbamate.

Antisense oligonucleotides of the disclosure were designed to bind to a target region spanning an intron 1/exon 2 and exon 2/intron 2 splice junction of a human myostatin pre-mRNA transcript and prepared using the following protocol:

Preparation of trityl piperazine phenyl carbamate 35 (FIG. 2A): To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile.

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO$_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts.

Introduction of the activated "Tail" onto the anchor-loaded resin was performed in dimethyl imidazolidinone (DMI) by the procedure used for incorporation of the subunits during solid phase synthesis.

Preparation of the Solid Support for Synthesis of morpholino-based oligomers: This procedure was performed in a silanized, jacketed peptide vessel (ChemGlass, N.J., USA)

with a coarse porosity (40-60 μm) glass frit, overhead stirrer, and 3-way Teflon stopcock to allow N2 to bubble up through the frit or a vacuum extraction.

The resin treatment/wash steps in the following procedure consist of two basic operations: resin fluidization or stirrer bed reactor and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

Figure 2B:
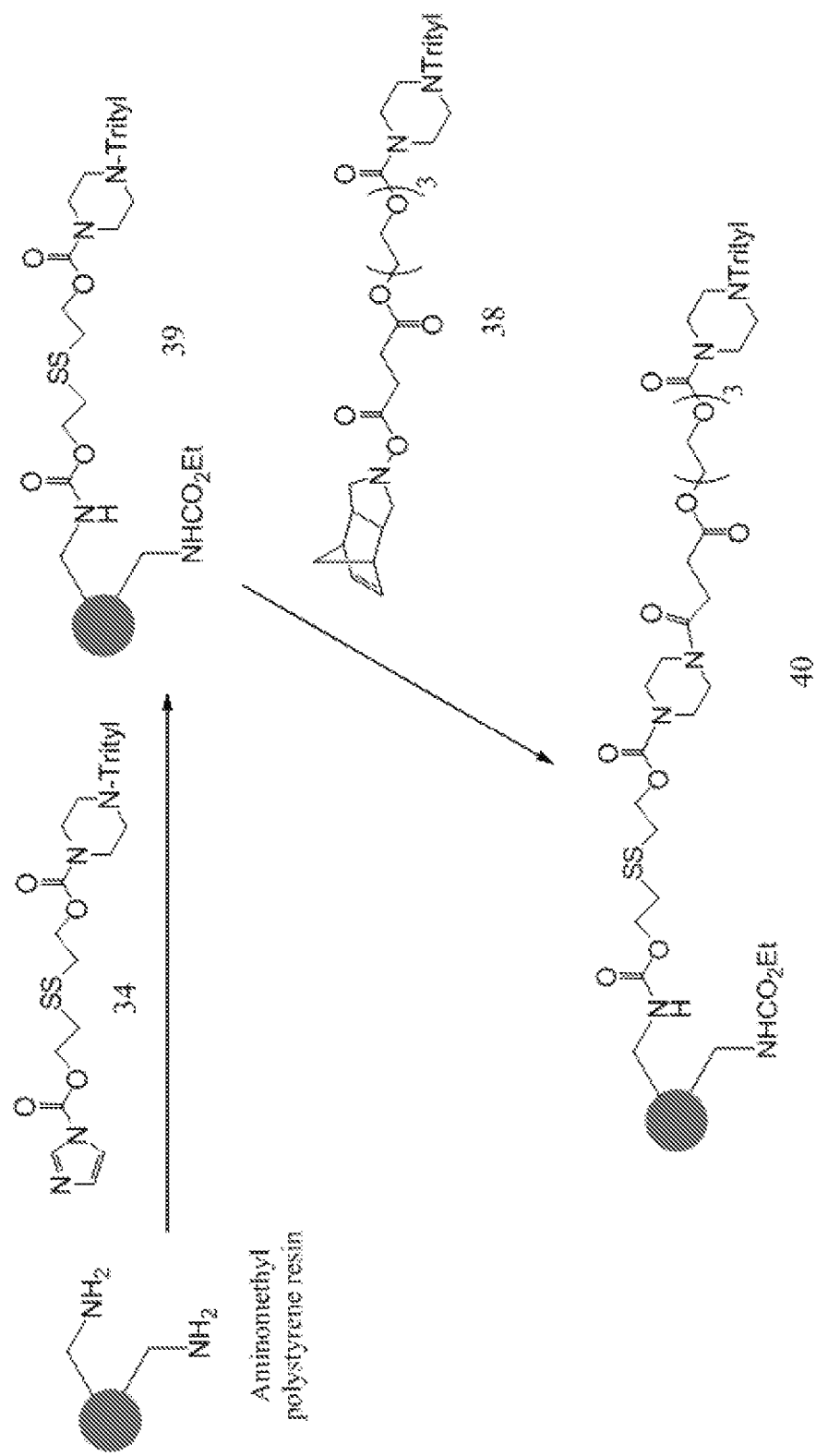
FIG. 2B illustrates preparation of a resin/reagent mixture.

To aminomethylpolystyrene resin (100-200 mesh; ~1.0 mmol/g load based on nitrogen substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was treated with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 (see FIG. 2B) was dried under a N2 stream for 1-3 hr and then under vacuum to constant weight (+2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 μL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (μmol/g) using the appropriate volumes, dilutions, extinction coefficient (c: 41 mol-1 cm-1) and resin weight. The assay is performed in triplicate and an average loading calculated.

The resin loading procedure in this example will provide resin with a loading of approximately 500 μmol/g. A loading of 300-400 in μmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into solid support. The anchor loaded resin was first deprotected under acidic condition and the resulting material neutralized before coupling. For the coupling step, a solution of 38 (0.2 M) in DMI containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Solid Phase Synthesis: morpholino-based oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 μmol/g of resin is preferred. For larger oligomers, aminomethylpolystyrene-disulfide resin with loading of 300-400 μmol/g of resin is preferred. If a molecule with 5'-Tail is desired, resin that has been loaded with Tail is chosen with the same loading guidelines.

The following reagent solutions were prepared:

Detritylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated morpholino subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

TABLE 4

| Step | Volume | Delivery | Hold time |
| --- | --- | --- | --- |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| DCM | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| DCM | 1.5 mL | Manifold | 30 sec. |
| Coupling | 350-500 uL | Syringe | 40 min. |
| DCM | 1.5 mL | Manifold | 30 sec. |
| Neutralization | 1.5 mL | Manifold | 30 sec. |
| Neutralization | 1.5 mL | Manifold | 30 sec. |

TABLE 4-continued

| Step | Volume | Delivery | Hold time |
|---|---|---|---|
| DCM | 1.5 mL | Manifold | 30 sec. |
| DCM | 1.5 mL | Manifold | 30 sec. |
| DCM | 1.5 mL | Manifold | 30 sec. |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and protecting groups: After methoxytritylation, the resin was washed 8 times with 2 mL 1-methyl-2-pyrrolidinone. One mL of a cleavage solution comprising 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 L of cleavage solution. To the solution was added 4.0 mL conc. Aqueous ammonia (stored at −20° C.), the vial capped tightly (with Teflon lined screw cap), and the mixture swirled to mix the solution. The vial was placed in a 45° C. oven for 16-24 hr to effect cleavage of base and protecting groups.

Crude product purification: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of morpholino-based oligomers: The pooled fractions from the Macroprep purification were treated with 1 M H3PO4 to lower the pH to 2.5. After initial mixing, the samples sat at room temperature for 4 min, at which time they were neutralized to pH 10-11 with 2.8% ammonia/water. The products were purified by solid phase extraction (SPE).

SPE column packing and conditioning: Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% NH4OH/80% acetonitrile; 0.5M NaOH/20% ethanol; water; 50 mM H3PO4/80% acetonitrile; water; 0.5 NaOH/20% ethanol; water; 0.28% NH$_4$OH.

SPE purification: The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia.

Product isolation: The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of morpholino-based oligomers by MALDI: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydoxycinnamic acid (HCCA) as matrices.

Example 2

In vitro Studies of Antisense Oligonucleotides

In vitro experiments were performed to investigate the ability of antisense oligonucleotides designed and prepared as described above to decrease the expression of exon 2 containing myostatin pre-mRNA. Both human rhabdomyosarcoma cells (RD cells; ATCC CCL-136) and primary human myoblasts were used in the experiments as noted. RD cells or primary human skeletal myoblasts were nucleofected with PMOs at 10, 3, 1 and 0.3 µM in SG or P3 nucleofector solution, respectively, and incubated overnight at 37° C. with 5% CO$_2$. Total RNA was isolated from the cells and RT-PCR was performed using primers Myostatin EX1 Fwd (5' ACAGTGAGCAAAAAGAAAATG SEQ ID NO: 48) and Myostatin EX3 Rev (5' TTGGAGACATCTTTGTGGGA SEQ ID NO: 49). Amplified samples were analyzed using the LabChip Caliper to determine percent exon 2 skipping. EC50 values were determined using non-linear regression analysis in GraphPad Prism. EC50 values represent the concentration at which the test PMO induces 50% exon skipping.

Figure 3:
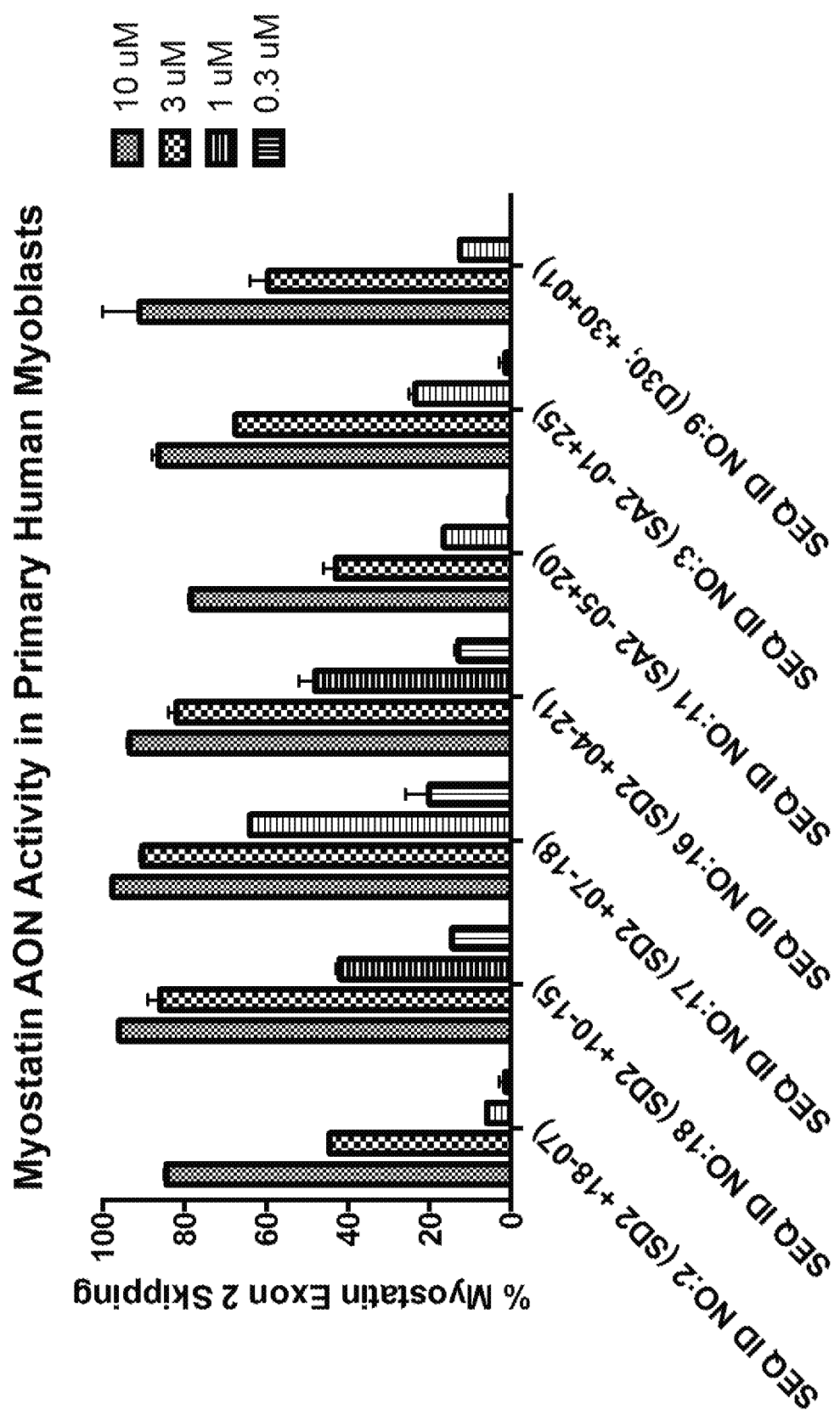
FIG. 3 illustrates a first series of myostatin antisense oligonucleotide (AON) activity in primary human myoblasts.

A first series of PMOs designed to target exon 2 of the human myostatin gene (huMSTN) including the exon 2 splice acceptor and splice donor sites was synthesized and used to treat primary human myoblasts as described above. The test PMOs compounds included SEQ ID NOS: 83, 84, 88, and 93-95. As shown in FIG. 3, PMOs targeted to the exon 2 splice sites were particularly effective at causing exon 2 skipping and showed improved activity compared to a sequence known in the prior art (D30; (+30+1); SEQ ID NO: 9; US Pub. No.: US 2013/0085139). EC50 values for this experiment are shown below:

TABLE 5

| Name | Targeting Sequence | SEQ ID NO: | 5' | 3' | EC50 (µM) |
|---|---|---|---|---|---|
| muhuMSTN-SD2(+07 − 18) | TTTTCAGTTATCACTTACCAGCCCA | 94 | TEG | H | 0.6618 |
| muhuMSTN-SD2(+04 − 21) | TTATTTTCAGTTATCACTTACCAGC | 93 | TEG | H | 1.051 |
| muhuMSTN-SD2(+10 − 15) | TCAGTTATCACTTACCAGCCCATCT | 95 | TEG | H | 1.068 |
| huMSTN-SA2(−01 + 25) | CCATCCACTTGCATTAGAAAATCAGC | 84 | TEG | H | 2.161 |
| huMSTN-SA2(−05 + 20) | CACTTGCATTAGAAAATCAGCTATA | 88 | TEG | H | 3.865 |
| muhuMSTN-SD2(+18 − 07) | CACTTACCAGCCCATCTTCTCCTGG | 83 | TEG | H | 3.883 |

TABLE 5-continued

| Name | Targeting Sequence | SEQ ID NO: | 5' | 3' | EC50 (μM) |
|---|---|---|---|---|---|
| muhuD30-SD2(+30 + 1) | CAGCCCATCTTCTCCT GGTCCTGGGAAGGT | 9 | TEG | H | 2.7 |

Figure 4:
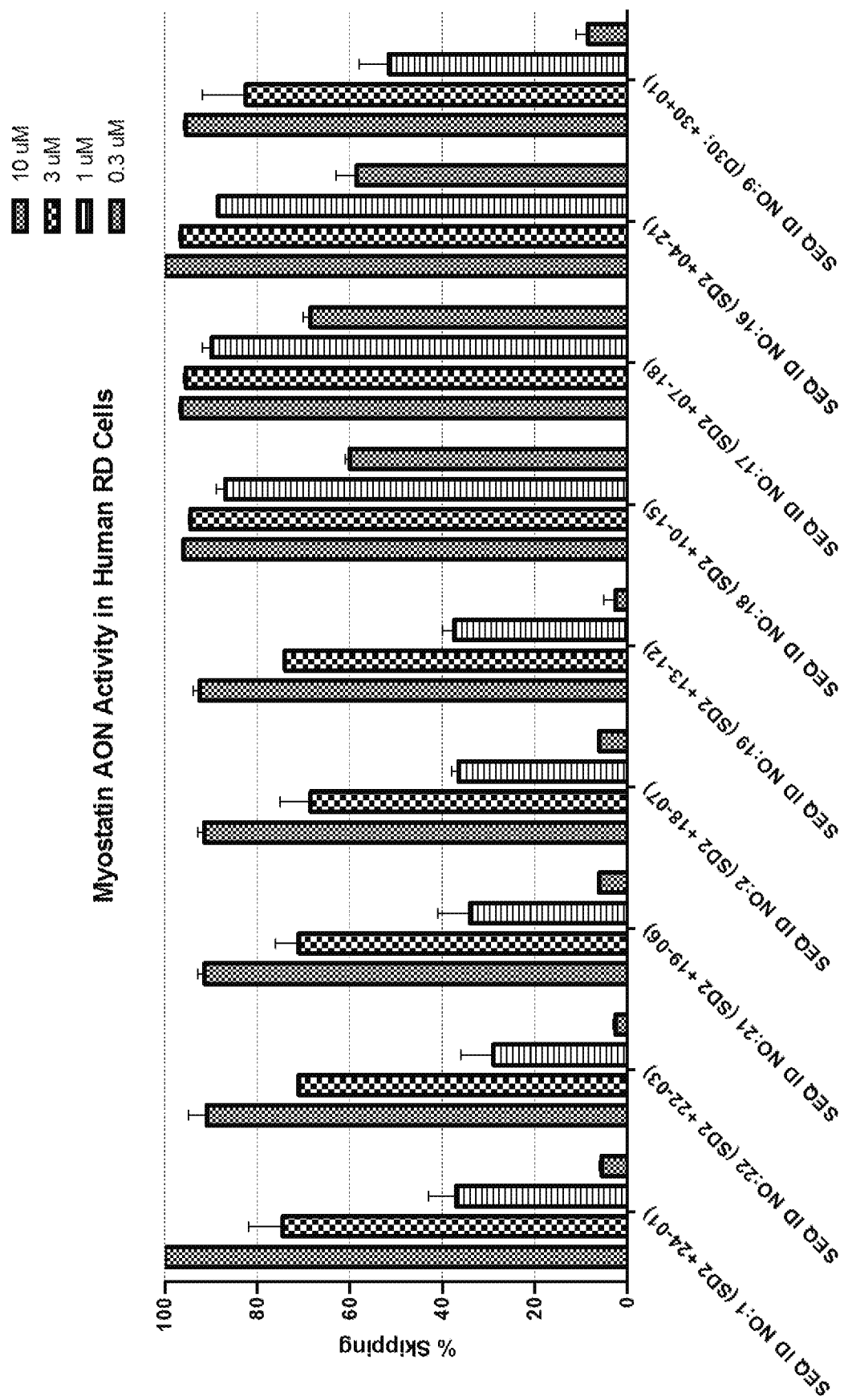
FIG. 4 illustrates a second series of myostatin antisense oligonucleotide (AON) activity in human rhabdomyosarcoma (RD) cells.

A second series of PMOs was designed and tested to identify PMOs that induced high levels of exon 2 skipping. In these experiments the PMOs were used to treat RD cells as described above. The tested PMOs included SEQ ID NOS: 82-83, 93-96, 98 and 99. As shown in FIG. 4, SEQ ID NOS: 93-95 were particularly effective PMOs at inducing exon 2 skipping and showed marked improvement over a AON sequence known in the prior art (D30; (+30+1); SEQ ID NO: 9; US Pub. No.: US 2013/0085139). The corresponding EC50 values for this experiment are shown below:

TABLE 6

| Name | Targeting Sequence | SEQ ID NO: | 5' | 3' | EC50 (μM) |
|---|---|---|---|---|---|
| muhuMSTN-SD2(+24 − 01) | CCAGCCCATCTTC TCCTGGTCCTGG | 82 | TEG | H | 1.412 |
| muhuMSTN-SD2(+22 − 03) | TACCAGCCCATCT TCTCCTGGTCCT | 99 | TEG | H | 1.408 |
| muhuMSTN-SD2(+19 − 06) | ACTTACCAGCCCA TCTTCTCCTGGT | 98 | TEG | H | 1.329 |
| muhuMSTN-SD2(+18 − 07) | CACTTACCAGCCC ATCTTCTCCTGG | 83 | TEG | H | 1.291 |
| muhuMSTN-SD2(+13 − 12) | GTTATCACTTACC AGCCCATCTTCT | 96 | TEG | H | 0.9699 |
| muhuMSTN-SD2(+10 − 15) | TCAGTTATCACTT ACCAGCCCATCT | 95 | TEG | H | *0.00002 |
| muhuMSTN-SD2(+07 − 18) | TTTTCAGTTATCA CTTACCAGCCCA | 94 | TEG | H | *0.00006 |
| muhuMSTN-SD2(+04 − 21) | TTATTTCAGTTA TCACTTACCAGC | 93 | TEG | H | *0.00092 |
| muhuD30-SD2(+30 − 1) | CAGCCCATCTTCTCC TGGTCCTGGGAAGGT | 9 | TEG | H | 0.5224 |

*Ambiguous fit on non-linear regression

Figure 5:
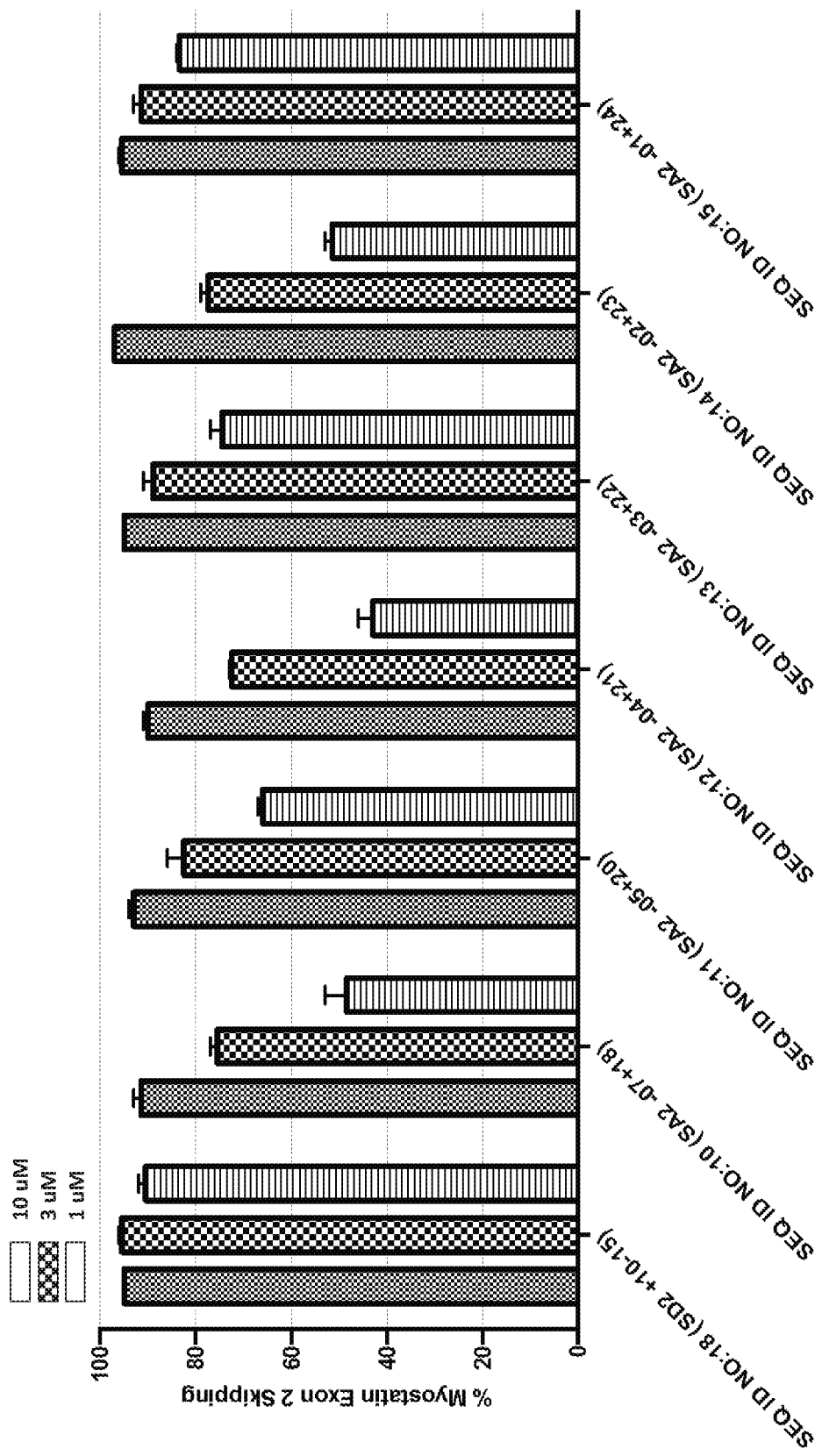
FIG. 5 illustrates a third series of myostatin antisense oligonucleotide (AON) activity in human rhabdomyosarcoma (RD) cells.

A third series of PMOs were designed and tested in RD cells using PMOs that targeted exon 2 splice sites. As shown in FIG. 5, some intra-exonic targets proved effective at inducing exon skipping. Based on the calculated EC50 values shown below, the most effective PMOs were those targeted to the splice donor and acceptor sites (e.g., see SEQ ID NOS: 95, 88, 89 and 92).

TABLE 7

| Name | Targeting Sequence | SEQ ID NO: | 5' | 3' | EC50 (μM) |
|---|---|---|---|---|---|
| muhuMSTN-SD2(+10 − 15) | TCAGTTATCACTT ACCAGCCCATCT | 95 | TEG | H | 0.1146 |
| huMSTN-SA2(−05 + 20) | CACTTGCATTAGA AAATCAGCTATA | 88 | TEG | H | 0.214 |
| huMSTN-SA2(−04 + 21) | CCACTTGCATTAG AAAATCAGCTAT | 89 | TEG | H | 0.3646 |
| huMSTN-SA2(−01 + 24) | CATCCACTTGCAT TAGAAAATCAGC | 92 | TEG | H | 0.5509 |
| huMSTN-SA2(−07 + 18) | CTTGCATTAGAAA ATCAGCTATAAA | 87 | TEG | H | 0.881 |
| huMSTN-SA2(02 + 23) | ATCCACTTGCATT AGAAAATCAGCT | 91 | TEG | H | 1.022 |
| huMSTN-SA2(−03 + 22) | TCCACTTGCATTA GAAAATCAGCTA | 90 | TEG | H | 11.93 |

Figure 6:
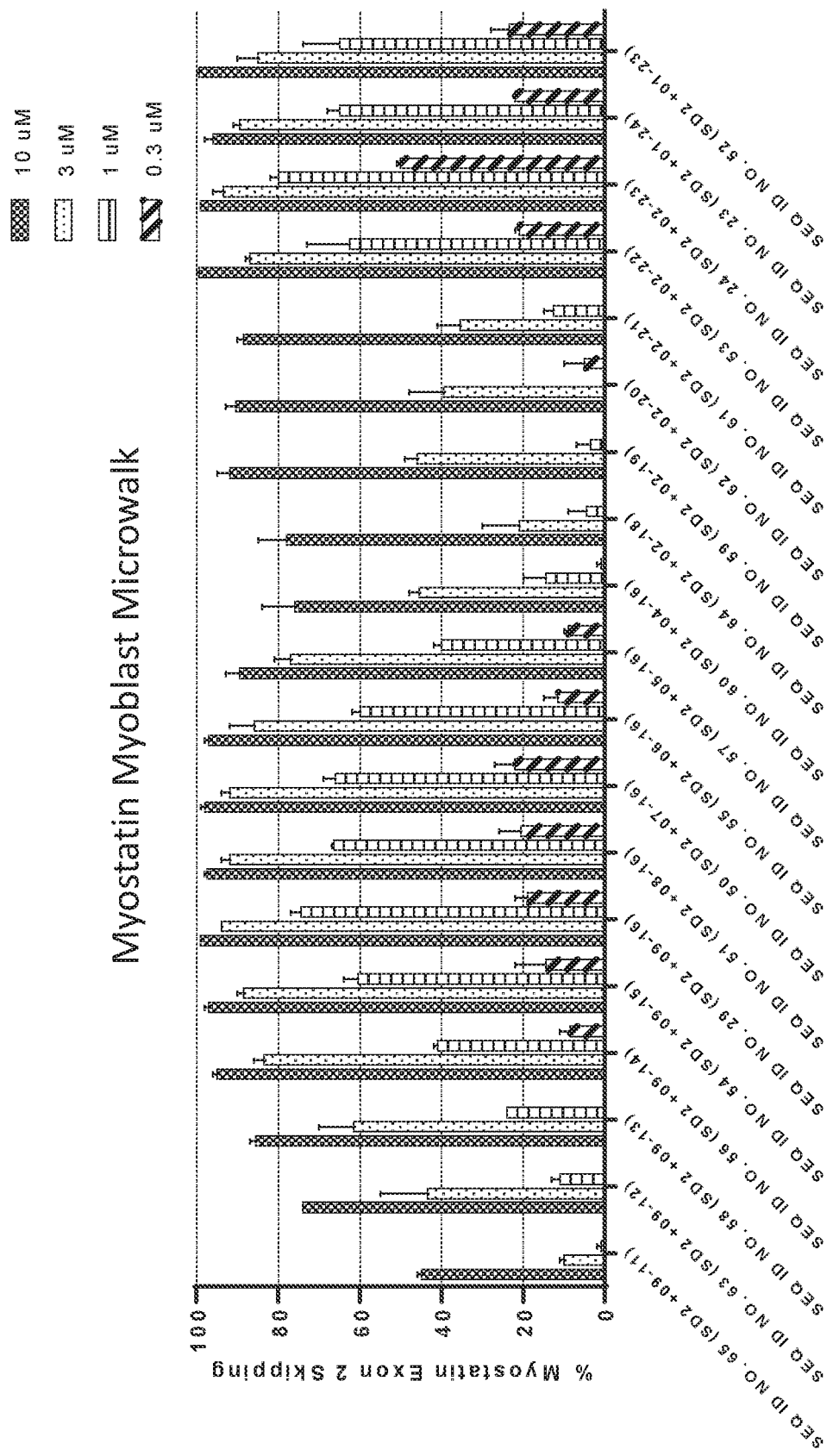
FIG. 6 illustrates a fourth series of myostatin antisense oligonucleotide (AON) activity in primary human myoblasts.

A fourth series of PMOs was designed and tested to identify PMOs that induced high levels of exon 2 skipping. In these experiments the PMOs were used to treat primary human myoblast cells as described above. The tested PMOs included SEQ ID NOS: 100, 101, 106 and 66-81. As shown in FIG. 6, PMOs targeted to the exon 2 splice sites were particularly effective at inducing exon 2 skipping. The corresponding EC50 values for this experiment are shown below:

TABLE 8

| Name | Targeting Sequence | SEQ ID NO: | 5' | 3' | EC50 (μM) |
|---|---|---|---|---|---|
| muhuMSTN-SD2(+01 − 24) | ATGTTATTTTCAG TTATCACTTACC | 100 | TEG | H | 0.6425 |
| muhuMSTN-SD2(+02 − 23) | TGTTATTTTCAGT TATCACTTACCA | 101 | TEG | H | 0.2774 |
| muhuMSTN-SD2(+09 − 16) | TTCAGTTATCACT TACCAGCCCATC | 106 | TEG | H | 0.5494 |
| muhuMSTN-SD2(+07 − 16) | TTCAGTTATCACT TACCAGCCCA | 66 | TEG | H | 0.6123 |
| muhuMSTN-SD2(+08 − 16) | TTCAGTTATCACT TACCAGCCCAT | 67 | TEG | H | 0.6223 |
| muhuMSTN-SD2(+01 − 23) | TGTTATTTTCAGT TATCACTTACC | 68 | TEG | H | 0.6484 |
| muhuMSTN-SD2(+02 − 22) | GTTATTTTCAGTT ATCACTTACCA | 69 | TEG | H | 0.687 |
| muhuMSTN-SD2(+09 − 15) | TCAGTTATCACTT ACCAGCCCATC | 70 | TEG | H | 0.7711 |
| muhuMSTN-SD2(+06 − 16) | TTCAGTTATCACT TACCAGCCC | 71 | TEG | H | 0.8287 |
| muhuMSTN-SD2(+09 − 14) | CAGTTATCACTTA CCAGCCCATC | 72 | TEG | H | 1.253 |
| muhuMSTN-SD2(+05 − 16) | TTCAGTTATCACT TACCAGCC | 73 | TEG | H | 1.333 |
| muhuMSTN-SD2(+09 − 13) | AGTTATCACTTAC CAGCCCATC | 74 | TEG | H | 2.399 |
| muhuMSTN-SD2(+02 − 19) | ATTTTCAGTTATC ACTTACCA | 75 | TEG | H | 3.583 |
| muhuMSTN-SD2(+04 − 16) | TTCAGTTATCACT TACCAGC | 76 | TEG | H | 3.914 |

TABLE 8-continued

| Name | Targeting Sequence | SEQ ID NO: | 5' | 3' | EC50 (μM) |
|---|---|---|---|---|---|
| muhuMSTN-SD2(+02 - 21) | TTATTTTCAGTTATCACTTACCA | 77 | TEG | H | 3.993 |
| muhuMSTN-SD2(+02 - 20) | TATTTTCAGTTATCACTTACCA | 78 | TEG | H | 4.061 |
| muhuMSTN-SD2(+09 - 12) | GTTATCACTTACCAGCCCATC | 79 | TEG | H | 4.35 |
| muhuMSTN-SD2(+02 - 18) | TTTTCAGTTATCACTTACCA | 80 | TEG | H | 6.214 |
| muhuMSTN-SD2(+09 - 11) | TTATCACTTACCAGCCCATC | 81 | TEG | H | >10 |

The sequences disclosed herein are further listed in Table 9 below:

TABLE 9

| | Sequence Listing | |
|---|---|---|
| muhuMSTN-SD2 (+24 - 01) | CCAGCCCAXCXXCXCCXGGXCCXGG | 1 |
| muhuMSTN-SD2 (+18 - 07) | CACXXACCAGCCCAXCXXCXCCXGG | 2 |
| huMSTN-SA2 (-01 + 25) | CCAXCCACXXGCAXXAGAAAAXCAGC | 3 |
| huMSTN-SA2 (-09 + 15) | GCAXXAGAAAAXCAGCXAXAAAXG | 4 |
| huMSTN-SA2 (-01 + 21) | CCACXXGCAXXAGAAAAXCAGC | 5 |
| SA2 | CTTTTCTTTTCTTATTCATTTATAGCTGATTTTCTAATGCAAGTGGATGG | 6 |
| SD2a | CCCAGGACCAGGAGAAGATGGGCTGGTAAGTGATAACTGAAAATAACATT | 7 |
| SD2b | ACCTTCCCAGGACCAGGAGAAGATGGGCTGGTAAGTGATAACTGAAAATAACATTATAAT | 8 |
| muhuD30-SD2 (+30 + 1) | CAGCCCATCTTCTCCTGGTCCTGGGAAGGT | 9 |
| huMSTN-SA2 (-07 + 18) | CXXGCAXXAGAAAAXCAGCXAXAAA | 10 |
| huMSTN-SA2 (-05 + 20) | CACXXGCAXXAGAAAAXCAGCXAXA | 11 |
| huMSTN-SA2 (-04 + 21) | CCACXXGCAXXAGAAAAXCAGCXAX | 12 |
| huMSTN-SA2 (-03 + 22) | XCCACXXGCAXXAGAAAAXCAGCXA | 13 |
| huMSTN-SA2 (-02 + 23) | AXCCACXXGCAXXAGAAAAXCAGCX | 14 |
| huMSTN-SA2 (-01 + 24) | CAXCCACXXGCAXXAGAAAAXCAGC | 15 |
| muhuMSTN-SD2 (+04 - 21) | XXAXXXXCAGXXAXCACXXACCAGC | 16 |
| muhuMSTN-SD2 (+07 - 18) | XXXXCAGXXAXCACXXACCAGCCCA | 17 |
| muhuMSTN-SD2 (+10 - 15) | XCAGXXAXCACXXACCAGCCCAXCX | 18 |
| muhuMSTN-SD2 (+13 - 12) | GXXAXCACXXACCAGCCCAXCXXCX | 19 |
| muhuMSTN-SD2 (+16 - 09) | AXCACXXACCAGCCCAXCXXCXCCX | 20 |
| muhuMSTN-SD2 (+19 - 06) | ACXXACCAGCCCAXCXXCXCCXGGX | 21 |

TABLE 9-continued

Sequence Listing

| | | |
|---|---|---|
| muhuMSTN-SD2 (+22 – 03) | XACCAGCCCAXCXXCXCCXGGXCCX | 22 |
| muhuMSTN-SD2 (+01 – 24) | AXGXXAXXXXCAGXXAXCACXXACC | 23 |
| muhuMSTN-SD2 (+02 – 23) | XGXXAXXXXCAGXXAXCACXXACCA | 24 |
| muhuMSTN-SD2 (+03 – 22) | GXXAXXXXCAGXXAXCACXXACCAG | 25 |
| muhuMSTN-SD2 (+05 – 20) | XAXXXXCAGXXAXCACXXACCAGCC | 26 |
| muhuMSTN-SD2 (+06 – 19) | AXXXXCAGXXAXCACXXACCAGCCC | 27 |
| muhuMSTN-SD2 (+08 – 17) | XXXCAGXXAXCACXXACCAGCCCAX | 28 |
| muhuMSTN-SD2 (+09 – 16) | XXCAGXXAXCACXXACCAGCCCAXC | 29 |
| muhuMSTN-SD2 (+11 – 14) | CAGXXAXCACXXACCAGCCCAXCXX | 30 |
| muhuMSTN-SD2 (+12 – 13) | AGXXAXCACXXACCAGCCCAXCXXC | 31 |
| rTAT | RRRQRRKKR | 32 |
| Tat | RKKRRQRRR | 33 |
| $R_9F_2$ | RRRRRRRRRFF | 34 |
| $R_5F_2R_4$ | RRRRRFFRRRR | 35 |
| $R_4$ | RRRR | 36 |
| $R_5$ | RRRRR | 37 |
| $R_6$ | RRRRRR | 38 |
| $R_7$ | RRRRRRR | 39 |
| $R_8$ | RRRRRRRR | 40 |
| $R_9$ | RRRRRRRRR | 41 |
| $(RX)_8$ | RAhxRAhxRAhxRAhxRAhxRAhxRAhxRAhx | 42 |
| $(RAhxR)_4$; (P007) | RAhxRRAhxRRAhxRRAhxR | 43 |
| $(RAhxR)_5$; (CP04057) | RAhxRRAhxRRAhxRRAhxRRAhxR | 44 |
| $(RAhxRRBR)_2$; (CP06062) | RAhxRRBRRAhxRRBR | 45 |
| $(RAR)_4F_2$ | RARRARRARRARFF | 46 |
| $(RGR)_4F_2$ | RGRRGRRGRRGRFF | 47 |
| Myostatin EX1 Fwd | ACAGTGAGCAAAAGAAAATG | 48 |
| Myostatin EX3 Rev | TTGGAGACATCTTTGTGGGA | 49 |
| muhuMSTN-SD2 (+07 – 16) | XXCAGXXAXCACXXACCAGCCCA | 50 |
| muhuMSTN-SD2 (+08 – 16) | XXCAGXXAXCACXXACCAGCCCAX | 51 |

TABLE 9-continued

Sequence Listing

| | | |
|---|---|---|
| muhuMSTN-SD2 (+01 - 23) | XGXXAXXXXCAGXXAXCACXXACC | 52 |
| muhuMSTN-SD2 (+02 - 22) | GXXAXXXXCAGXXAXCACXXACCA | 53 |
| muhuMSTN-SD2 (+09 - 15) | XCAGXXAXCACXXACCAGCCCAXC | 54 |
| muhuMSTN-SD2 (+06 - 16) | XXCAGXXAXCACXXACCAGCCC | 55 |
| muhuMSTN-SD2 (+09 - 14) | CAGXXAXCACXXACCAGCCCAXC | 56 |
| muhuMSTN-SD2 (+05 - 16) | XXCAGXXAXCACXXACCAGCC | 57 |
| muhuMSTN-SD2 (+09 - 13) | AGXXAXCACXXACCAGCCCAXC | 58 |
| muhuMSTN-SD2 (+02 - 19) | AXXXXCAGXXAXCACXXACCA | 59 |
| muhuMSTN-SD2 (+04 - 16) | XXCAGXXAXCACXXACCAGC | 60 |
| muhuMSTN-SD2 (+02 - 21) | XXAXXXXCAGXXAXCACXXACCA | 61 |
| muhuMSTN-SD2 (+02 - 20) | XAXXXXCAGXXAXCACXXACCA | 62 |
| muhuMSTN-SD2 (+09 - 12) | GXXAXCACXXACCAGCCCAXC | 63 |
| muhuMSTN-SD2 (+02 - 18) | XXXXCAGXXAXCACXXACCA | 64 |
| muhuMSTN-SD2 (+09 - 11) | XXAXCACXXACCAGCCCAXC | 65 |
| muhuMSTN-SD2 (+07 - 16) | TTCAGTTATCACTTACCAGCCCA | 66 |
| muhuMSTN-SD2 (+08 - 16) | TTCAGTTATCACTTACCAGCCCAT | 67 |
| muhuMSTN-SD2 (+01 - 23) | TGTTATTTTCAGTTATCACTTACC | 68 |
| muhuMSTN-SD2 (+02 - 22) | GTTATTTTCAGTTATCACTTACCA | 69 |
| muhuMSTN-SD2 (+09 - 15) | TCAGTTATCACTTACCAGCCCATC | 70 |
| muhuMSTN-SD2 (+06 - 16) | TTCAGTTATCACTTACCAGCCC | 71 |
| muhuMSTN-SD2 (+09 - 14) | CAGTTATCACTTACCAGCCCATC | 72 |
| muhuMSTN-SD2 (+05 - 16) | TTCAGTTATCACTTACCAGCC | 73 |
| muhuMSTN-SD2 (+09 - 13) | AGTTATCACTTACCAGCCCATC | 74 |
| muhuMSTN-SD2 (+02 - 19) | ATTTTCAGTTATCACTTACCA | 75 |
| muhuMSTN-SD2 (+04 - 16) | TTCAGTTATCACTTACCAGC | 76 |
| muhuMSTN-SD2 (+02 - 21) | TTATTTTCAGTTATCACTTACCA | 77 |

TABLE 9-continued

| Sequence Listing | | |
|---|---|---|
| muhuMSTN-SD2 (+02 − 20) | TATTTTCAGTTATCACTTACCA | 78 |
| muhuMSTN-SD2 (+09 − 12) | GTTATCACTTACCAGCCCATC | 79 |
| muhuMSTN-SD2 (+02 − 18) | TTTTCAGTTATCACTTACCA | 80 |
| muhuMSTN-SD2 (+09 − 11) | TTATCACTTACCAGCCCATC | 81 |
| muhuMSTN-SD2 (+24 − 01) | CCAGCCCATCTTCTCCTGGTCCTGG | 82 |
| muhuMSTN-SD2 (+18 − 07) | CACTTACCAGCCCATCTTCTCCTGG | 83 |
| huMSTN-SA2 (−01 + 25) | CCATCCACTTGCATTAGAAAATCAGC | 84 |
| huMSTN-SA2 (−09 + 15) | GCATTAGAAAATCAGCTATAAATG | 85 |
| huMSTN-SA2 (−01 + 21) | CCACTTGCATTAGAAAATCAGC | 86 |
| huMSTN-SA2 (−07 + 18) | CTTGCATTAGAAAATCAGCTATAAA | 87 |
| huMSTN-SA2 (−05 + 20) | CACTTGCATTAGAAAATCAGCTATA | 88 |
| huMSTN-SA2 (−04 + 21) | CCACTTGCATTAGAAAATCAGCTAT | 89 |
| huMSTN-SA2 (−03 + 22) | TCCACTTGCATTAGAAAATCAGCTA | 90 |
| huMSTN-SA2 (−02 + 23) | ATCCACTTGCATTAGAAAATCAGCT | 91 |
| huMSTN-SA2 (−01 + 24) | CATCCACTTGCATTAGAAAATCAGC | 92 |
| muhuMSTN-SD2 (+04 − 21) | TTATTTTCAGTTATCACTTACCAGC | 93 |
| muhuMSTN-SD2 (+07 − 18) | TTTTCAGTTATCACTTACCAGCCCA | 94 |
| muhuMSTN-SD2 (+10 − 15) | TCAGTTATCACTTACCAGCCCATCT | 95 |
| muhuMSTN-SD2 (+13 − 12) | GTTATCACTTACCAGCCCATCTTCT | 96 |
| muhuMSTN-SD2 (+16 − 09) | ATCACTTACCAGCCCATCTTCTCCT | 97 |
| muhuMSTN-SD2 (+19 − 06) | ACTTACCAGCCCATCTTCTCCTGGT | 98 |
| muhuMSTN-SD2 (+22 − 03) | TACCAGCCCATCTTCTCCTGGTCCT | 99 |
| muhuMSTN-SD2 (+01 − 24) | ATGTTATTTTCAGTTATCACTTACC | 100 |
| muhuMSTN-SD2 (+02 − 23) | TGTTATTTTCAGTTATCACTTACCA | 101 |
| muhuMSTN-SD2 (+03 − 22) | GTTATTTTCAGTTATCACTTACCAG | 102 |
| muhuMSTN-SD2 (+05 − 20) | TATTTTCAGTTATCACTTACCAGCC | 103 |

TABLE 9-continued

| Sequence Listing | | |
|---|---|---|
| muhuMSTN-SD2 (+06 - 19) | ATTTTCAGTTATCACTTACCAGCCC | 104 |
| muhuMSTN-SD2 (+08 - 17) | TTTCAGTTATCACTTACCAGCCCAT | 105 |
| muhuMSTN-SD2 (+09 - 16) | TTCAGTTATCACTTACCAGCCCATC | 106 |
| muhuMSTN-SD2 (+11 - 14) | CAGTTATCACTTACCAGCCCATCTT | 107 |
| muhuMSTN-SD2 (+12 - 13) | AGTTATCACTTACCAGCCCATCTTC | 108 |

What is claimed is:

1. An antisense oligomer compound of consisting of a sequence selected from SEQ ID NOS: 2-5, 10-15, and 17-30, wherein X is independently selected from uracil (U) or thymine (T), comprising:

at least one subunit that is a nucleotide analog having (i) a modified internucleoside linkage, (ii) a modified sugar moiety, or (iii) a combination of the foregoing.

2. The antisense oligomer compound of claim 1, wherein the modified internucleoside linkage is selected from a phosphorothioate internucleoside linkage, a phosphoramidate internucleoside linkage, a phosphorodiamidate internucleoside linkage, or a phosphorodiamidate wherein the phosphorous atom is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

3. The antisense oligomer compound of claim 1, further comprising an arginine-rich cell-penetrating peptide covalently bonded to the 3' or the 5' end of the antisense oligomer compound.

4. The antisense oligomer compound of claim 1, wherein a nucleobase of each of the subunits is independently adenine, guanine, thymine, uracil, cytosine, inosine, hypoxanthine, 2,6-diaminopurine, 5-methyl cytosine, C5-propynyl-modified pyrimidines, or 10-(9-(aminoethoxy)phenoxazinyl).

5. A compound of formula (I):

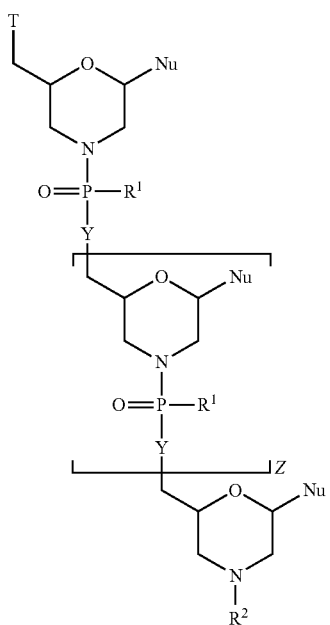

or a pharmaceutically acceptable salt thereof, wherein:
each Nu is a nucleobase which taken together form a targeting sequence;
Z is an integer from 15 to 25;
each Y is independently selected from O and —NR$^4$, wherein each R$^4$ is independently selected from H, C$_1$-C$_6$ alkyl, aralkyl, —C(=NH)NH$_2$, —C(O)(CH$_2$)$_n$NR$^5$C(=NH)NH$_2$,
—C(O)(CH$_2$)$_2$NH$^5$C(O)(CH$_2$)NR$^5$C(=NH)NH$_2$, and G, wherein R$^5$ is selected from H and C$_1$-C$_6$ alkyl and n is an integer from 1 to 5;
T is selected from OH and a moiety of the formula:

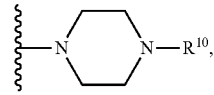

wherein:
A is selected from —OH, —N(R$^7$)$_2$, and R$^1$ wherein:
each R$^7$ is independently selected from H and C$_1$-C$_6$ alkyl, and
R$^6$ is selected from OH, —N(R$^9$)CH$_2$C(O)NH$_2$, and a moiety of the formula:

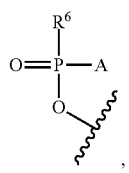

wherein:
R$^9$ is selected from H and C$_1$-C$_6$ alkyl; and
R$^{10}$ is selected from G, —C(O)—R$^{11}$OH, acyl, trityl, 4-methoxytrityl,
—C(=NH)NH$_2$, —C(O)(CH$_2$)$_m$NR$^{12}$C(=NH)NH$_2$, and
—C(O)(CH$_2$)$_2$NHC(O)(CH$_2$)$_5$NR$^{12}$C(=NH)NH$_2$,
wherein:
m is an integer from 1 to 5,
R$^{11}$ is of the formula —(O-alkyl)$_y$— wherein y is an integer from 3 to 10 and each of the y alkyl groups is independently selected from C$_2$-C$_6$ alkyl; and
R$^{12}$ is selected from H and C$_1$-C$_6$ alkyl;
each instance of R$^1$ is independently selected from:
—N(R$^{13}$)$_2$, wherein each R$^{13}$ is independently selected from H and C$_1$-C$_6$ alkyl;
a moiety of formula (II):

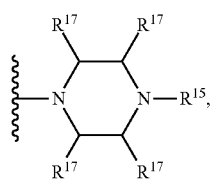

(II)

wherein:
R$^{15}$ is selected from H, G, C$_1$-C$_6$ alkyl, —C(=NH)NH$_2$,

—C(O)(CH$_2$)$_q$NR$^{18}$C(=NH)NH$_2$, and
—C(O)(CH$_2$)$_2$NHC(O)(CH$_2$)$_5$NR$^{18}$C(=NH)NH$_2$,
wherein:
R$^{18}$ is selected from H and C$_1$-C$_6$ alkyl; and
q is an integer from 1 to 5; and
each R$^{17}$ is independently selected from H and methyl; and
a moiety of formula(III):

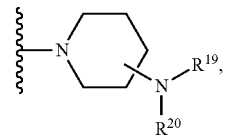

(III)

wherein:
R$^{19}$ is selected from H, C$_1$-C$_6$ alkyl, —C(=NH)NH$_2$,
—C(O)(CH$_2$)$_r$NR$^{22}$C(=NH)NH$_2$,
—C(O)CH(NH$_2$)(CH$_2$)$_3$NHC(=NH)NH$_2$,
—C(O)(CH$_2$)$_2$NHC(O)(CH$_2$)$_5$NR$^{22}$C(=NH)NH$_2$,
—C(O)CH(NH$_2$)(CH$_2$)$_4$NH$_2$ and G,
wherein:
R$^{22}$ is selected from H and C$_1$-C$_6$ alkyl; and
r is an integer from 1 to 5,
R$^{20}$ is selected from H and C$_1$-C$_6$ alkyl; and
R$^2$ is selected from H, G, acyl, trityl, 4-methoxytrityl, C$_1$-C$_6$ alkyl, —C(=NH)NH$_2$, —C(=NH)NH$_2$, —C(O)—R$^{23}$,
—C(O)(CH$_2$)$_s$NR$^{24}$C(=NH)NH$_2$,
—C(O)(CH$_2$)$_2$NHC(O)(CH$_2$)$_5$NR$^{24}$C(=NH)NH$_2$, —C(O)CH(NH$_2$)(CH$_2$)$_3$NHC(=NH)NH$_2$, and a moiety of the formula:

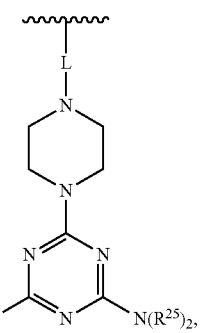

wherein,
R$^{23}$ is of the formula —(O-alkyl)$_v$—OH wherein v is an integer from 3 to 10 and each of the v alkyl groups is independently selected from C$_2$-C$_6$ alkyl; and
R$^{24}$ is selected from H and C$_1$-C$_6$ alkyl;
s is an integer from 1 to 5;
L is selected from —C(O)(CH$_2$)$_6$C(O)— and —C(O)(CH$_2$)$_2$S$_2$(CH$_2$)$_2$C(O)—; and
each R$^{25}$ is of the formula —(CH$_2$)$_2$OC(O)N(R$^{26}$)$_2$ wherein each R$^{26}$ is of the formula —(CH$_2$)$_6$NHC(=NH)NH$_2$, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

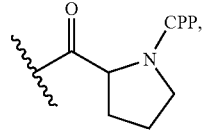

wherein the CPP is attached to the linker moiety by an amide bond at the CPP carboxy terminus, with the proviso that up to one instance of G is present, and wherein the targeting sequence consists of a sequence selected from SEQ ID NOS: 2-5, 10-15, and 17-30 and wherein X is independently selected from uracil (U) or thymine (T).

6. The compound of claim 5, wherein each Nu is independently adenine, guanine, thymine, uracil, cytosine, inosine, hypoxanthine, 2,6-diaminopurine, 5-methyl cytosine, C5-propynyl-modified pyrimidines, or 10-(9-(aminoethoxy)phenoxazinyl).

7. The compound of claim 5, wherein the targeting sequence is selected from SEQ ID NOS: 24 or 29.

8. The compound of claim 5, wherein Y is O, R$^2$ is selected from H or G, R$^3$ is selected from an electron pair or H.

9. The compound of claim 8, wherein R$^2$ is G, and wherein the CPP is of a sequence selected from SEQ ID NOS: 32-47.

10. The compound of claim 5, wherein each R$^1$ is —N(CH$_3$)$_2$.

11. The compound of claim 5, wherein T is of the formula:

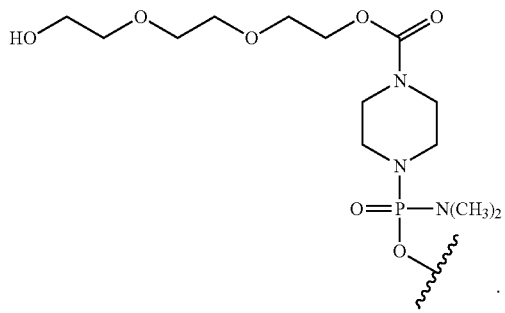 [SMILES: *OP(=O)(N(C)C)N1CCN(C(=O)OCCOCCOCCO)CC1]

12. The compound of claim 5, wherein T is of the formula:

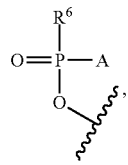

wherein A is —N(CH$_3$)$_2$, and R$^6$ is of the formula:

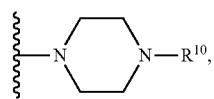

wherein R$^{10}$ is G, and
wherein G is —C(O)CH$_2$NH—CPP.

13. The compound of claim 12, wherein the CPP is of a sequence selected from SEQ ID NOS: 32-47.

14. The antisense oligomer compound of claim 1, wherein the targeting sequence is selected from SEQ ID NOS:17-29.

* * * * *

SEQUENCE LISTING

<160> NUMBER OF SEQ ID NOS: 108

<210> SEQ ID NO 1
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (9)..(23)
<223> OTHER INFORMATION: n is t or u

<400> SEQUENCE: 1
ccagcccanc nncnccnggn ccngg          25

<210> SEQ ID NO 2
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (4)..(23)
<223> OTHER INFORMATION: n is t or u

<400> SEQUENCE: 2
cacnnaccag cccancnncn ccngg          25

<210> SEQ ID NO 3
<211> LENGTH: 26
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (4)..(22)
<223> OTHER INFORMATION: n is t or u

<400> SEQUENCE: 3
ccanccacnn gcannagaaa ancagc         26

<210> SEQ ID NO 4
<211> LENGTH: 24
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (4)..(23)
<223> OTHER INFORMATION: n is t or u

<400> SEQUENCE: 4
gcannagaaa ancagcnana aang                                          24

<210> SEQ ID NO 5
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (5)..(18)
<223> OTHER INFORMATION: n is t or u

<400> SEQUENCE: 5
ccacnngcan nagaaaanca gc                                            22

<210> SEQ ID NO 6
<211> LENGTH: 50
<212> TYPE: DNA
<213> ORGANISM: Artificial Sequence
<220> FEATURE:
<223> OTHER INFORMATION: Target Sequence - SA2

<400> SEQUENCE: 6
cttttctttt cttattcatt tatagctgat tttctaatgc aagtggatgg              50

<210> SEQ ID NO 7
<211> LENGTH: 50
<212> TYPE: DNA
<213> ORGANISM: Artificial Sequence
<220> FEATURE:
<223> OTHER INFORMATION: Target Sequence - SD2a

<400> SEQUENCE: 7
cccaggacca ggagaagatg ggctggtaag tgataactga aaataacatt              50

<210> SEQ ID NO 8
<211> LENGTH: 60
<212> TYPE: DNA
<213> ORGANISM: Artificial Sequence
<220> FEATURE:
<223> OTHER INFORMATION: Target Sequence - SD2b

<400> SEQUENCE: 8
accttcccag gaccaggaga agatgggctg gtaagtgata actgaaaata acattataat  60

<210> SEQ ID NO 9
<211> LENGTH: 30
<212> TYPE: DNA
<213> ORGANISM: Artificial Sequence
<220> FEATURE:
<223> OTHER INFORMATION: Antisense Oligomer

<400> SEQUENCE: 9
cagcccatct tctcctggtc ctgggaaggt                                    30

<210> SEQ ID NO 10
<211> LENGTH: 25
<212> TYPE: DNA
<213> ORGANISM: Artificial Sequence
<220> FEATURE:

```
<223> OTHER INFORMATION: Antisense Oligomer
<220> FEATURE:
<221> NAME/KEY: misc_feature
<222> LOCATION: (2)..(22)
<223> OTHER INFORMATION: n is t or u

<400> SEQUENCE: 10
cnngcannag aaaancagcn anaaa                                              25

<210> SEQ ID NO 11
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (4)..(24)
<223> OTHER INFORMATION: n is t or u

<400> SEQUENCE: 11
cacnngcann agaaaancag cnana                                              25

<210> SEQ ID NO 12
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (5)..(25)
<223> OTHER INFORMATION: n is t or u

<400> SEQUENCE: 12
ccacnngcan nagaaaanca gcnan                                              25

<210> SEQ ID NO 13
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(24)
<223> OTHER INFORMATION: n is t or u

<400> SEQUENCE: 13
nccacnngca nnagaaaanc agcna                                              25

<210> SEQ ID NO 14
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(25)
<223> OTHER INFORMATION: n is t or u

<400> SEQUENCE: 14
anccacnngc annagaaaan cagcn                                              25

<210> SEQ ID NO 15
<211> LENGTH: 25
<212> TYPE: DNA
<213> ORGANISM: Artificial Sequence
```

```
<220> FEATURE:
<223> OTHER INFORMATION: Antisense Oligomer
<220> FEATURE:
<221> NAME/KEY: misc_feature
<222> LOCATION: (3)..(21)
<223> OTHER INFORMATION: n is t or u

<400> SEQUENCE: 15
canccacnng cannagaaaa ncagc                                              25

<210> SEQ ID NO 16
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(19)
<223> OTHER INFORMATION: n is t or u

<400> SEQUENCE: 16
nnannnncag nnancacnna ccagc                                              25

<210> SEQ ID NO 17
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(16)
<223> OTHER INFORMATION: n is t or u

<400> SEQUENCE: 17
nnnncagnna ncacnnacca gccca                                              25

<210> SEQ ID NO 18
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(25)
<223> OTHER INFORMATION: n is t or u

<400> SEQUENCE: 18
ncagnnanca cnnaccagcc cancn                                              25

<210> SEQ ID NO 19
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(25)
<223> OTHER INFORMATION: n is t or u

<400> SEQUENCE: 19
gnnancacnn accagcccan cnncn                                              25

<210> SEQ ID NO 20
<211> LENGTH: 25
<212> TYPE: DNA
```

<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(25)
<223> OTHER INFORMATION: n is t or u

<400> SEQUENCE: 20
ancacnnacc agcccancnn cnccn                                    25

<210> SEQ ID NO 21
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (3)..(25)
<223> OTHER INFORMATION: n is t or u

<400> SEQUENCE: 21
acnnaccagc ccancnncnc cnggn                                    25

<210> SEQ ID NO 22
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(25)
<223> OTHER INFORMATION: n is t or u

<400> SEQUENCE: 22
naccagccca ncnncnccng gnccn                                    25

<210> SEQ ID NO 23
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(22)
<223> OTHER INFORMATION: n is t or u

<400> SEQUENCE: 23
angnnannnn cagnnancac nnacc                                    25

<210> SEQ ID NO 24
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(21)
<223> OTHER INFORMATION: n is t or u

<400> SEQUENCE: 24
ngnnannnnc agnnancacn nacca                                    25

<210> SEQ ID NO 25
<211> LENGTH: 25

```
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(20)
<223> OTHER INFORMATION: n is t or u

<400> SEQUENCE: 25
gnnannnnca gnnancacnn accag                                              25

<210> SEQ ID NO 26
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(18)
<223> OTHER INFORMATION: n is t or u

<400> SEQUENCE: 26
nannnncagn nancacnnac cagcc                                              25

<210> SEQ ID NO 27
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(17)
<223> OTHER INFORMATION: n is t or u

<400> SEQUENCE: 27
annnncagnn ancacnnacc agccc                                              25

<210> SEQ ID NO 28
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(25)
<223> OTHER INFORMATION: n is t or u

<400> SEQUENCE: 28
nnncagnnan cacnnaccag cccan                                              25

<210> SEQ ID NO 29
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(24)
<223> OTHER INFORMATION: n is t or u

<400> SEQUENCE: 29
nncagnnanc acnnaccagc ccanc                                              25

<210> SEQ ID NO 30
```

```
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (4)..(25)
<223> OTHER INFORMATION: n is t or u

<400> SEQUENCE: 30
cagnnancac nnaccagccc ancnn                                              25

<210> SEQ ID NO 31
<211> LENGTH: 25
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (3)..(24)
<223> OTHER INFORMATION: n is t or u

<400> SEQUENCE: 31
agnnancacn naccagccca ncnnc                                              25

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide - rTAT

<400> SEQUENCE: 32

Arg Arg Arg Gln Arg Arg Lys Lys Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Peptide - Tat

<400> SEQUENCE: 33

Arg Lys Lys Arg Arg Gln Arg Arg Arg
1               5

<210> SEQ ID NO 34
<211> LENGTH: 11
<212> TYPE: PRT
<213> ORGANISM: Artificial Sequence
<220> FEATURE:
<223> OTHER INFORMATION: Synthetic Peptide - R9F2

<400> SEQUENCE: 34

Arg Arg Arg Arg Arg Arg Arg Arg Arg Phe Phe
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic Peptide - R5F2R4

<400> SEQUENCE: 35
```

Arg Arg Arg Arg Arg Phe Phe Arg Arg Arg
1               5                   10

<210> SEQ ID NO 36
<211> LENGTH: 4
<212> TYPE: PRT
<213> ORGANISM: Artificial Sequence
<220> FEATURE:
<223> OTHER INFORMATION: Synthetic Peptide - R4

<400> SEQUENCE: 36

Arg Arg Arg Arg
1

<210> SEQ ID NO 37
<211> LENGTH: 5
<212> TYPE: PRT
<213> ORGANISM: Artificial Sequence
<220> FEATURE:
<223> OTHER INFORMATION: Synthetic Peptide - R5

<400> SEQUENCE: 37

Arg Arg Arg Arg Arg
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Peptide - R6

<400> SEQUENCE: 38

Arg Arg Arg Arg Arg Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Peptide - R7

<400> SEQUENCE: 39

Arg Arg Arg Arg Arg Arg Arg
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Peptide - R8

<400> SEQUENCE: 40

Arg Arg Arg Arg Arg Arg Arg Arg
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Peptide - R9

<400> SEQUENCE: 41

Arg Arg Arg Arg Arg Arg Arg Arg Arg

```
1               5

<210> SEQ ID NO 42
<211> LENGTH: 16
<212> TYPE: PRT
<213> ORGANISM: Artificial Sequence
<220> FEATURE:
<223> OTHER INFORMATION: Synthetic Peptide - (RX)8
<220> FEATURE:
<221> NAME/KEY: misc_feature
<222> LOCATION: (2)..(16)
<223> OTHER INFORMATION: Xaa is 6-aminohexanoic acid

<400> SEQUENCE: 42

Arg Xaa Arg Xaa Arg Xaa Arg Xaa Arg Xaa Arg Xaa Arg Xaa Arg Xaa
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Synthetic Peptide - (RAhxR)4; (P007)
<220> FEATURE:
<221> NAME/KEY: misc_feature
<222> LOCATION: (2)..(11)
<223> OTHER INFORMATION: Xaa is 6-aminohexanoic acid

<400> SEQUENCE: 43

Arg Xaa Arg Arg Xaa Arg Arg Xaa Arg Arg Xaa Arg
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Synthetic Peptide - (RAhxR)5; (CP04057)
<220> FEATURE:
<221> NAME/KEY: misc_feature
<222> LOCATION: (2)..(14)
<223> OTHER INFORMATION: Xaa is 6-aminohexanoic acid

<400> SEQUENCE: 44

Arg Xaa Arg Arg Xaa Arg Arg Xaa Arg Arg Xaa Arg Arg Xaa Arg
1               5                   10                  15

<210> SEQ ID NO 45
<211> LENGTH: 12
<212> TYPE: PRT
<213> ORGANISM: Artificial Sequence
<220> FEATURE:
<223> OTHER INFORMATION: Synthetic Peptide - (RAhxRRBR)2; (CP06062)
<220> FEATURE:
<221> NAME/KEY: misc_feature
<222> LOCATION: (2)..(2)
<223> OTHER INFORMATION: Xaa is 6-aminohexanoic acid
<220> FEATURE:
<221> NAME/KEY: misc_feature
<222> LOCATION: (5)..(5)
<223> OTHER INFORMATION: Xaa is Beta-Alanine
<220> FEATURE:
<221> NAME/KEY: misc_feature
<222> LOCATION: (8)..(8)
<223> OTHER INFORMATION: Xaa is 6-aminohexanoic acid
<220> FEATURE:
<221> NAME/KEY: misc_feature
<222> LOCATION: (11)..(11)
<223> OTHER INFORMATION: Xaa is Beta-Alanine

<400> SEQUENCE: 45
```

```
Arg Xaa Arg Arg Xaa Arg Arg Xaa Arg Arg Xaa Arg
1               5                  10

<210> SEQ ID NO 46
<211> LENGTH: 14
<212> TYPE: PRT
<213> ORGANISM: Artificial Sequence
<220> FEATURE:
<223> OTHER INFORMATION: Synthetic Peptide - (RAR)4F2

<400> SEQUENCE: 46

Arg Ala Arg Arg Ala Arg Arg Ala Arg Arg Ala Arg Phe Phe
1               5                  10

<210> SEQ ID NO 47
<211> LENGTH: 14
<212> TYPE: PRT
<213> ORGANISM: Artificial Sequence
<220> FEATURE:
<223> OTHER INFORMATION: Synthetic Peptide - (RGR)4F2

<400> SEQUENCE: 47

Arg Gly Arg Arg Gly Arg Arg Gly Arg Arg Gly Arg Phe Phe
1               5                  10

<210> SEQ ID NO 48
<211> LENGTH: 21
<212> TYPE: DNA
<213> ORGANISM: Artificial Sequence
<220> FEATURE:
<223> OTHER INFORMATION: Forward Primer

<400> SEQUENCE: 48
acagtgagca aaagaaaat g                                              21

<210> SEQ ID NO 49
<211> LENGTH: 20
<212> TYPE: DNA
<213> ORGANISM: Artificial Sequence
<220> FEATURE:
<223> OTHER INFORMATION: Reverse Primer

<400> SEQUENCE: 49
ttggagacat ctttgtggga                                               20

<210> SEQ ID NO 50
<211> LENGTH: 23
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(14)
<223> OTHER INFORMATION: n is t or u

<400> SEQUENCE: 50
nncagnnanc acnnaccagc cca                                           23

<210> SEQ ID NO 51
<211> LENGTH: 24
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(24)
```

<223> OTHER INFORMATION: n is t or u

<400> SEQUENCE: 51
nncagnnanc acnnaccagc ccan                24

<210> SEQ ID NO 52
<211> LENGTH: 24
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(21)
<223> OTHER INFORMATION: n is t or u

<400> SEQUENCE: 52
ngnnannnnc agnnancacn nacc                24

<210> SEQ ID NO 53
<211> LENGTH: 24
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(20)
<223> OTHER INFORMATION: n is t or u

<400> SEQUENCE: 53
gnnannnnca gnnancacnn acca                24

<210> SEQ ID NO 54
<211> LENGTH: 24
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(23)
<223> OTHER INFORMATION: n is t or u

<400> SEQUENCE: 54
ncagnnanca cnnaccagcc canc                24

<210> SEQ ID NO 55
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(14)
<223> OTHER INFORMATION: n is t or u

<400> SEQUENCE: 55
nncagnnanc acnnaccagc cc                  22

<210> SEQ ID NO 56
<211> LENGTH: 23
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature

```
<222> LOCATION: (4)..(22)
<223> OTHER INFORMATION: n is t or u

<400> SEQUENCE: 56
cagnnancac nnaccagccc anc                                              23

<210> SEQ ID NO 57
<211> LENGTH: 21
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(14)
<223> OTHER INFORMATION: n is t or u

<400> SEQUENCE: 57
nncagnnanc acnnaccagc c                                                21

<210> SEQ ID NO 58
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (3)..(21)
<223> OTHER INFORMATION: n is t or u

<400> SEQUENCE: 58
agnnancacn naccagccca nc                                               22

<210> SEQ ID NO 59
<211> LENGTH: 21
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(17)
<223> OTHER INFORMATION: n is t or u

<400> SEQUENCE: 59
annnncagnn ancacnnacc a                                                21

<210> SEQ ID NO 60
<211> LENGTH: 20
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(14)
<223> OTHER INFORMATION: n is t or u

<400> SEQUENCE: 60
nncagnnanc acnnaccagc                                                  20

<210> SEQ ID NO 61
<211> LENGTH: 23
<212> TYPE: DNA
<213> ORGANISM: Artificial Sequence
<220> FEATURE:
<223> OTHER INFORMATION: Antisense Oligomer
<220> FEATURE:
```

```
<221> NAME/KEY: misc_feature
<222> LOCATION: (1)..(19)
<223> OTHER INFORMATION: n is t or u

<400> SEQUENCE: 61
nnannnncag nnancacnna cca                                              23

<210> SEQ ID NO 62
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(18)
<223> OTHER INFORMATION: n is t or u

<400> SEQUENCE: 62
nannnncagn nancacnnac ca                                               22

<210> SEQ ID NO 63
<211> LENGTH: 21
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (2)..(20)
<223> OTHER INFORMATION: n is t or u

<400> SEQUENCE: 63
gnnancacnn accagcccan c                                                21

<210> SEQ ID NO 64
<211> LENGTH: 20
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(16)
<223> OTHER INFORMATION: n is t or u

<400> SEQUENCE: 64
nnnncagnna ncacnnacca                                                  20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(19)
<223> OTHER INFORMATION: n is t or u

<400> SEQUENCE: 65
nnancacnna ccagcccanc                                                  20

<210> SEQ ID NO 66
<211> LENGTH: 23
<212> TYPE: DNA
<213> ORGANISM: Artificial Sequence
<220> FEATURE:
<223> OTHER INFORMATION: Antisense Oligomer
```

```
<400> SEQUENCE: 66
ttcagttatc acttaccagc cca                                          23

<210> SEQ ID NO 67
<211> LENGTH: 24
<212> TYPE: DNA
<213> ORGANISM: Artificial Sequence
<220> FEATURE:
<223> OTHER INFORMATION: Antisense Oligomer

<400> SEQUENCE: 67
ttcagttatc acttaccagc ccat                                         24

<210> SEQ ID NO 68
<211> LENGTH: 24
<212> TYPE: DNA
<213> ORGANISM: Artificial Sequence
<220> FEATURE:
<223> OTHER INFORMATION: Antisense Oligomer

<400> SEQUENCE: 68
tgttattttc agttatcact tacc                                         24

<210> SEQ ID NO 69
<211> LENGTH: 24
<212> TYPE: DNA
<213> ORGANISM: Artificial Sequence
<220> FEATURE:
<223> OTHER INFORMATION: Antisense Oligomer

<400> SEQUENCE: 69
gttattttca gttatcactt acca                                         24

<210> SEQ ID NO 70
<211> LENGTH: 24
<212> TYPE: DNA
<213> ORGANISM: Artificial Sequence
<220> FEATURE:
<223> OTHER INFORMATION: Antisense Oligomer

<400> SEQUENCE: 70
tcagttatca cttaccagcc catc                                         24

<210> SEQ ID NO 71
<211> LENGTH: 22
<212> TYPE: DNA
<213> ORGANISM: Artificial Sequence
<220> FEATURE:
<223> OTHER INFORMATION: Antisense Oligomer

<400> SEQUENCE: 71
ttcagttatc acttaccagc cc                                           22

<210> SEQ ID NO 72
<211> LENGTH: 23
<212> TYPE: DNA
<213> ORGANISM: Artificial Sequence
<220> FEATURE:
<223> OTHER INFORMATION: Antisense Oligomer

<400> SEQUENCE: 72
cagttatcac ttaccagccc atc                                          23

<210> SEQ ID NO 73
```

```
<211> LENGTH: 21
<212> TYPE: DNA
<213> ORGANISM: Artificial Sequence
<220> FEATURE:
<223> OTHER INFORMATION: Antisense Oligomer

<400> SEQUENCE: 73
ttcagttatc acttaccagc c                                              21

<210> SEQ ID NO 74
<211> LENGTH: 22
<212> TYPE: DNA
<213> ORGANISM: Artificial Sequence
<220> FEATURE:
<223> OTHER INFORMATION: Antisense Oligomer

<400> SEQUENCE: 74
agttatcact taccagccca tc                                             22

<210> SEQ ID NO 75
<211> LENGTH: 21
<212> TYPE: DNA
<213> ORGANISM: Artificial Sequence
<220> FEATURE:
<223> OTHER INFORMATION: Antisense Oligomer

<400> SEQUENCE: 75
attttcagtt atcacttacc a                                              21

<210> SEQ ID NO 76
<211> LENGTH: 20
<212> TYPE: DNA
<213> ORGANISM: Artificial Sequence
<220> FEATURE:
<223> OTHER INFORMATION: Antisense Oligomer

<400> SEQUENCE: 76
ttcagttatc acttaccagc                                                20

<210> SEQ ID NO 77
<211> LENGTH: 23
<212> TYPE: DNA
<213> ORGANISM: Artificial Sequence
<220> FEATURE:
<223> OTHER INFORMATION: Antisense Oligomer

<400> SEQUENCE: 77
ttattttcag ttatcactta cca                                            23

<210> SEQ ID NO 78
<211> LENGTH: 22
<212> TYPE: DNA
<213> ORGANISM: Artificial Sequence
<220> FEATURE:
<223> OTHER INFORMATION: Antisense Oligomer

<400> SEQUENCE: 78
tattttcagt tatcacttac ca                                             22

<210> SEQ ID NO 79
<211> LENGTH: 21
<212> TYPE: DNA
<213> ORGANISM: Artificial Sequence
<220> FEATURE:
<223> OTHER INFORMATION: Antisense Oligomer

<400> SEQUENCE: 79
```

```
gttatcactt accagcccat c                                            21

<210> SEQ ID NO 80
<211> LENGTH: 20
<212> TYPE: DNA
<213> ORGANISM: Artificial Sequence
<220> FEATURE:
<223> OTHER INFORMATION: Antisense Oligomer

<400> SEQUENCE: 80
ttttcagtta tcacttacca                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligomer

<400> SEQUENCE: 81
ttatcactta ccagcccatc                                              20

<210> SEQ ID NO 82
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 82
ccagcccatc ttctcctggt cctgg                                        25

<210> SEQ ID NO 83
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 83
cacttaccag cccatcttct cctgg                                        25

<210> SEQ ID NO 84
<211> LENGTH: 26
<212> TYPE: DNA
<213> ORGANISM: Artificial Sequence
<220> FEATURE:
<223> OTHER INFORMATION: Antisense Oligomer

<400> SEQUENCE: 84
ccatccactt gcattagaaa atcagc                                       26

<210> SEQ ID NO 85
<211> LENGTH: 24
<212> TYPE: DNA
<213> ORGANISM: Artificial Sequence
<220> FEATURE:
<223> OTHER INFORMATION: Antisense Oligomer

<400> SEQUENCE: 85
gcattagaaa atcagctata aatg                                         24

<210> SEQ ID NO 86
<211> LENGTH: 22
<212> TYPE: DNA
```

```
<213> ORGANISM: Artificial Sequence
<220> FEATURE:
<223> OTHER INFORMATION: Antisense Oligomer

<400> SEQUENCE: 86
ccacttgcat tagaaaatca gc                                              22

<210> SEQ ID NO 87
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 87
cttgcattag aaaatcagct ataaa                                           25

<210> SEQ ID NO 88
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 88
cacttgcatt agaaaatcag ctata                                           25

<210> SEQ ID NO 89
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 89
ccacttgcat tagaaaatca gctat                                           25

<210> SEQ ID NO 90
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 90
tccacttgca ttagaaaatc agcta                                           25

<210> SEQ ID NO 91
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 91
atccacttgc attagaaaat cagct                                           25

<210> SEQ ID NO 92
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 92
catccacttg cattagaaaa tcagc                                           25
```

<210> SEQ ID NO 93
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 93
ttattttcag ttatcactta ccagc                                       25

<210> SEQ ID NO 94
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 94
ttttcagtta tcacttacca gccca                                       25

<210> SEQ ID NO 95
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 95
tcagttatca cttaccagcc catct                                       25

<210> SEQ ID NO 96
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 96
gttatcactt accagcccat cttct                                       25

<210> SEQ ID NO 97
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 97
atcacttacc agcccatctt ctcct                                       25

<210> SEQ ID NO 98
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 98
acttaccagc ccatcttctc ctggt                                       25

<210> SEQ ID NO 99
<211> LENGTH: 25
<212> TYPE: DNA
<213> ORGANISM: Artificial Sequence
<220> FEATURE:

<223> OTHER INFORMATION: Antisense Oligomer

<400> SEQUENCE: 99
taccagccca tcttctcctg gtcct                                              25

<210> SEQ ID NO 100
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 100
atgttatttt cagttatcac ttacc                                              25

<210> SEQ ID NO 101
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 101
tgttattttc agttatcact tacca                                              25

<210> SEQ ID NO 102
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 102
gttattttca gttatcactt accag                                              25

<210> SEQ ID NO 103
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 103
tattttcagt tatcacttac cagcc                                              25

<210> SEQ ID NO 104
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 104
attttcagtt atcacttacc agccc                                              25

<210> SEQ ID NO 105
<211> LENGTH: 25
<212> TYPE: DNA
<213> ORGANISM: Artificial Sequence

```
<220> FEATURE:
<223> OTHER INFORMATION: Antisense Oligomer

<400> SEQUENCE: 105
tttcagttat cacttaccag cccat                                         25

<210> SEQ ID NO 106
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 106
ttcagttatc acttaccagc ccatc                                         25

<210> SEQ ID NO 107
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 107
cagttatcac ttaccagccc atctt                                         25

<210> SEQ ID NO 108
<211> LENGTH: 25
<212> TYPE: DNA
<213> ORGANISM: Artificial Sequence
<220> FEATURE:
<223> OTHER INFORMATION: Antisense Oligomer

<400> SEQUENCE: 108
agttatcact taccagccca tcttc                                         25
```